United States Patent
Vasquez et al.

(10) Patent No.: US 10,188,397 B2
(45) Date of Patent: Jan. 29, 2019

(54) TORQUE ALLEVIATING INTRA-AIRWAY LUNG VOLUME REDUCTION COMPRESSIVE IMPLANT STRUCTURES

(71) Applicant: PneumRx, Inc., Santa Clara, CA (US)

(72) Inventors: Jaime Vasquez, Fremont, CA (US); Mark L. Mathis, Fremont, CA (US); Timothy Machold, Moss Beach, CA (US); Andrew Stein, Boston, MA (US)

(73) Assignee: PneumRx, Inc., Santa Clara, CA (US)

( * ) Notice: Subject to any disclaimer, the term of this patent is extended or adjusted under 35 U.S.C. 154(b) by 240 days.

(21) Appl. No.: 15/192,085

(22) Filed: Jun. 24, 2016

(65) Prior Publication Data
US 2017/0027584 A1 Feb. 2, 2017

Related U.S. Application Data

(63) Continuation of application No. 14/209,194, filed on Mar. 13, 2014, now Pat. No. 9,402,633.
(Continued)

(51) Int. Cl.
*A61B 17/08* (2006.01)
*A61B 17/12* (2006.01)

(52) U.S. Cl.
CPC .. *A61B 17/12104* (2013.01); *A61B 17/12036* (2013.01); *A61B 17/12145* (2013.01); *A61B 17/1215* (2013.01); *A61B 2017/1205* (2013.01)

(58) Field of Classification Search
CPC ........ A61B 17/12022; A61B 17/12104; A61B 17/12131; A61B 17/1214;
(Continued)

(56) References Cited

U.S. PATENT DOCUMENTS 3,559,652 A 2/1971 Banitt et al.
4,013,080 A 3/1977 Froning et al.
(Continued)

FOREIGN PATENT DOCUMENTS

FR 2840796 12/2003
JP 04022908 2/1992
(Continued)

OTHER PUBLICATIONS

The United States Pharmacopeia. 29th Revision. The United States Pharmacopeia Convention. Rockville, 2006, 4 pages.
(Continued)

*Primary Examiner* — Gregory Anderson
(74) *Attorney, Agent, or Firm* — Kilpatrick Townsend & Stockton LLP

(57) ABSTRACT

A device for enhancing the breathing efficiency of a patient is provided. The implantable device may include a deployed configuration with one or more helical sections with proximal end in a stand-off proximal end configuration. The stand-off proximal end configuration may reduce migration of the deployed device and may preserve implant tissue compression. Alternative configurations may include two or more helical sections with a transition section disposed between the two or more helical sections. A device may include a right-handed helical section and a left-handed helical section and the transition section comprises a switchback transition section. The switchback section may provide greater control of the device during deployment by limiting recoiling forces of a device comprising a spring material. The deployed device may compress the lung to increase a gas filling resistance of the compressed portion of the lung, and/or increase tension and elastic recoil in other portions of the lung.

20 Claims, 36 Drawing Sheets

Related U.S. Application Data

(60) Provisional application No. 61/791,517, filed on Mar. 15, 2013.

(58) Field of Classification Search
CPC .......... A61B 17/12145; A61B 17/1215; A61B 17/12172; A61B 2017/00809; A61F 2002/043; A61F 2/04
See application file for complete search history.

(56) References Cited

U.S. PATENT DOCUMENTS

| | | |
|---|---|---|
| 4,153,058 A | 5/1979 | Nehme et al. |
| 4,233,984 A | 11/1980 | Walling et al. |
| 4,245,624 A | 1/1981 | Komiya et al. |
| 4,479,792 A | 10/1984 | Lazarus et al. |
| 4,494,531 A | 1/1985 | Gianturco |
| 4,532,935 A | 8/1985 | Wang et al. |
| 4,702,260 A | 10/1987 | Wang |
| 4,739,760 A | 4/1988 | Chin et al. |
| 4,766,906 A | 8/1988 | Wang et al. |
| 4,769,017 A | 9/1988 | Fath et al. |
| 4,821,722 A | 4/1989 | Miller et al. |
| 4,880,015 A | 11/1989 | Nierman |
| 5,056,529 A | 10/1991 | de Groot et al. |
| 5,084,012 A | 1/1992 | Kelman et al. |
| 5,108,368 A | 4/1992 | Hammerslag et al. |
| 5,165,420 A | 11/1992 | Strickland |
| 5,186,167 A | 2/1993 | Kolobow |
| 5,190,546 A | 3/1993 | Jervis |
| 5,219,895 A | 6/1993 | Kelman et al. |
| 5,240,011 A | 8/1993 | Assa |
| 5,261,889 A | 11/1993 | Laine et al. |
| 5,303,714 A | 4/1994 | Abele et al. |
| 5,312,329 A | 5/1994 | Beaty et al. |
| 5,312,331 A | 5/1994 | Knoepfler |
| 5,315,992 A | 5/1994 | Dalton |
| 5,334,183 A | 8/1994 | Wuchinich |
| 5,342,387 A | 8/1994 | Summers et al. |
| 5,354,287 A | 10/1994 | Wacks |
| 5,385,606 A | 1/1995 | Kowanko |
| 5,423,830 A | 6/1995 | Schneebaum et al. |
| 5,472,017 A | 12/1995 | Kovalcheck |
| 5,484,401 A | 1/1996 | Rodriguez et al. |
| 5,479,938 A | 2/1996 | Weier |
| 5,514,536 A | 5/1996 | Taylor |
| 5,522,819 A | 6/1996 | Graves et al. |
| 5,526,821 A | 6/1996 | Jamshidi |
| 5,549,551 A | 8/1996 | Peacock, III et al. |
| 5,549,904 A | 8/1996 | Juergensen et al. |
| 5,599,294 A | 2/1997 | Edwards et al. |
| 5,660,175 A | 8/1997 | Dayal |
| 5,660,185 A | 8/1997 | Shmulewitz et al. |
| 5,697,365 A | 12/1997 | Pell |
| 5,735,264 A | 4/1998 | Siczek et al. |
| 5,736,132 A | 4/1998 | Juergensen et al. |
| 5,750,657 A | 5/1998 | Edwardson et al. |
| 5,762,070 A | 6/1998 | Nagamatsu |
| 5,846,235 A | 12/1998 | Pasricha et al. |
| 5,875,692 A | 3/1999 | Lin et al. |
| 5,895,417 A | 4/1999 | Pomeranz et al. |
| 5,916,210 A | 6/1999 | Winston et al. |
| 5,916,212 A | 6/1999 | Baust et al. |
| 5,938,635 A | 8/1999 | Kuhle et al. |
| 5,941,249 A | 8/1999 | Maynard |
| 5,954,636 A | 9/1999 | Schwartz et al. |
| 5,957,919 A | 9/1999 | Laufer |
| 5,964,770 A | 10/1999 | Flomenblit et al. |
| 5,972,026 A | 10/1999 | Laufer et al. |
| 5,978,697 A | 11/1999 | Maytal et al. |
| 6,063,111 A | 5/2000 | Hieshima et al. |
| 6,066,090 A | 5/2000 | Yoon et al. |
| 6,080,113 A | 6/2000 | Heneveld et al. |
| 6,083,255 A | 7/2000 | Laufer et al. |
| 6,123,665 A | 9/2000 | Kawano |
| 6,174,323 B1 | 1/2001 | Biggs et al. |
| 6,183,498 B1 | 2/2001 | Devore et al. |
| 6,196,966 B1 | 3/2001 | Kerin et al. |
| 6,200,333 B1 | 3/2001 | Laufer |
| 6,245,090 B1 | 6/2001 | Gilson et al. |
| 6,258,100 B1 | 7/2001 | Alferness |
| 6,267,732 B1 | 7/2001 | Heneveld et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,287,304 B1 | 9/2001 | Eggers et al. |
| 6,293,951 B1 | 9/2001 | Alferness et al. |
| 6,299,633 B1 | 10/2001 | Laufer et al. |
| 6,306,141 B1 | 10/2001 | Jervis |
| 6,310,166 B1 | 10/2001 | Hickey et al. |
| 6,312,428 B1 | 11/2001 | Eggers et al. |
| 6,315,737 B1 | 11/2001 | Skinner et al. |
| 6,328,689 B1 | 12/2001 | Gonzalez et al. |
| 6,328,701 B1 | 12/2001 | Terwilliger et al. |
| 6,352,503 B1 | 3/2002 | Matsui et al. |
| 6,379,373 B1 | 4/2002 | Sawhney et al. |
| 6,387,044 B1 | 5/2002 | Tachibana et al. |
| 6,390,967 B1 | 5/2002 | Forman et al. |
| 6,398,775 B1 | 6/2002 | Perkins et al. |
| 6,402,701 B1 | 6/2002 | Kaplan et al. |
| 6,402,754 B1 | 6/2002 | Gonzalez |
| 6,402,781 B1 | 6/2002 | Langberg et al. |
| 6,411,852 B1 | 6/2002 | Danek et al. |
| 6,416,554 B1 | 7/2002 | Alferness et al. |
| 6,443,944 B1 | 9/2002 | Doshi et al. |
| 6,447,534 B2 | 9/2002 | Cragg et al. |
| 6,464,648 B1 | 10/2002 | Nakamura et al. |
| 6,474,340 B1 | 11/2002 | Vaska et al. |
| 6,478,730 B1 | 11/2002 | Bala et al. |
| 6,485,407 B2 | 11/2002 | Alferness et al. |
| 6,485,436 B1 | 11/2002 | Truckai et al. |
| 6,488,673 B1 | 12/2002 | Laufer et al. |
| 6,491,706 B1 | 12/2002 | Alferness et al. |
| 6,494,844 B1 | 12/2002 | Van Bladel et al. |
| 6,494,897 B2 | 12/2002 | Sterman et al. |
| 6,509,031 B1 | 1/2003 | Miller et al. |
| 6,514,290 B1 | 2/2003 | Loomas |
| 6,514,522 B2 | 2/2003 | Domb |
| 6,527,761 B1 | 3/2003 | Soltesz et al. |
| 6,537,195 B2 | 3/2003 | Forman et al. |
| 6,537,314 B2 | 3/2003 | Langberg et al. |
| 6,540,694 B1 | 4/2003 | Van Bladel et al. |
| 6,540,716 B1 | 4/2003 | Holm et al. |
| 6,549,800 B1 | 4/2003 | Atalar et al. |
| 6,551,255 B2 | 4/2003 | Van Bladel et al. |
| 6,551,302 B1 | 4/2003 | Rosinko et al. |
| 6,552,172 B2 | 4/2003 | Marx et al. |
| 6,558,337 B2 | 5/2003 | Dvorak et al. |
| 6,568,387 B2 | 5/2003 | Davenport et al. |
| 6,569,166 B2 | 5/2003 | Gonzalez |
| 6,577,893 B1 | 6/2003 | Besson et al. |
| 6,585,639 B1 | 7/2003 | Kotmel et al. |
| 6,589,161 B2 | 7/2003 | Corcoran et al. |
| 6,592,559 B1 | 7/2003 | Pakter et al. |
| 6,592,594 B2 | 7/2003 | Rimbaugh et al. |
| 6,599,311 B1 | 7/2003 | Biggs et al. |
| 6,610,043 B1 | 8/2003 | Ingenito et al. |
| 6,622,731 B2 | 9/2003 | Daniel et al. |
| 6,629,951 B2 | 10/2003 | Laufer et al. |
| 6,632,222 B1 | 10/2003 | Sharkey et al. |
| 6,632,239 B2 | 10/2003 | Snyder et al. |
| 6,632,243 B1 | 10/2003 | Zadno-azizi et al. |
| 6,634,363 B1 | 10/2003 | Danek et al. |
| 6,638,275 B1 | 10/2003 | McGaffigan et al. |
| 6,645,205 B2 | 11/2003 | Ginn et al. |
| 6,652,516 B1 | 11/2003 | Gough et al. |
| 6,652,520 B2 | 11/2003 | Moorman et al. |
| 6,653,525 B2 | 11/2003 | Ingenito et al. |
| 6,663,624 B2 | 12/2003 | Edwards et al. |
| 6,679,264 B1 | 1/2004 | Deem et al. |
| 6,682,520 B2 | 1/2004 | Ingenito |
| 6,685,626 B2 | 2/2004 | Wironen |
| 6,689,072 B2 | 2/2004 | Kaplan et al. |

(56) References Cited

U.S. PATENT DOCUMENTS

| | | |
|---|---|---|
| 6,690,976 B2 | 2/2004 | Fenn et al. |
| 6,692,494 B1 | 2/2004 | French et al. |
| 6,694,977 B1 | 2/2004 | Federowicz et al. |
| 6,694,979 B2 | 2/2004 | Deem et al. |
| 6,695,791 B2 | 2/2004 | Gonzalez et al. |
| 6,709,401 B2 | 3/2004 | Perkins et al. |
| 6,709,408 B2 | 3/2004 | Fisher et al. |
| 6,709,456 B2 | 3/2004 | Langberg et al. |
| 6,712,812 B2 | 3/2004 | Roschak et al. |
| 6,716,180 B2 | 4/2004 | Fontenot et al. |
| 6,723,095 B2 | 4/2004 | Hammerslag et al. |
| 6,730,044 B2 | 5/2004 | Stephens et al. |
| 6,736,822 B2 | 5/2004 | McClellan et al. |
| 6,749,606 B2 | 6/2004 | Keast et al. |
| 6,752,767 B2 | 6/2004 | Turovskiy et al. |
| 6,752,812 B1 | 6/2004 | Truwit et al. |
| 6,758,824 B1 | 7/2004 | Miller et al. |
| 6,768,425 B2 | 7/2004 | Flaherty et al. |
| 6,770,066 B1 | 8/2004 | Leighton et al. |
| 6,770,070 B1 | 8/2004 | Balbierz et al. |
| 6,789,545 B2 | 9/2004 | Littrup et al. |
| 6,790,172 B2 | 9/2004 | Alferness et al. |
| 6,790,185 B1 | 9/2004 | Fisher et al. |
| 6,797,001 B2 | 9/2004 | Mathis et al. |
| 6,802,858 B2 | 10/2004 | Gambale et al. |
| 6,807,446 B2 | 10/2004 | Fenn et al. |
| 6,808,525 B2 | 10/2004 | Latterell et al. |
| 6,814,778 B1 | 11/2004 | Farnworth et al. |
| 6,817,973 B2 | 11/2004 | Merril et al. |
| 6,825,091 B2 | 11/2004 | Bae et al. |
| 6,827,086 B2 | 12/2004 | Shuman et al. |
| 6,827,683 B2 | 12/2004 | Otawara et al. |
| 6,830,756 B2 | 12/2004 | Hnojewyj et al. |
| 6,840,243 B2 | 1/2005 | Deem et al. |
| 6,840,948 B2 | 1/2005 | Albrecht et al. |
| 6,840,952 B2 | 1/2005 | Saker et al. |
| 6,843,767 B2 | 1/2005 | Corcoran et al. |
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 | 4/2005 | Herrmann |
| 6,878,141 B1 | 4/2005 | Perkins et al. |
| 6,886,558 B2 | 5/2005 | Tanaka et al. |
| 6,901,927 B2 | 6/2005 | Deem et al. |
| 6,902,526 B2 | 6/2005 | Katzman et al. |
| 6,902,536 B2 | 6/2005 | Manna et al. |
| 6,904,909 B2 | 6/2005 | Andreas et al. |
| 6,907,881 B2 | 6/2005 | Suki et al. |
| 6,908,440 B2 | 6/2005 | Fisher et al. |
| 6,918,881 B2 | 7/2005 | Miller et al. |
| 6,929,637 B2 | 8/2005 | Gonzalez et al. |
| 6,936,014 B2 | 8/2005 | Vetter et al. |
| 6,941,950 B2 | 9/2005 | Wilson et al. |
| 6,942,627 B2 | 9/2005 | Huitema et al. |
| 6,945,942 B2 | 9/2005 | Van Bladel et al. |
| 6,962,587 B2 | 11/2005 | Johnson et al. |
| 6,964,662 B2 | 11/2005 | Kidooka et al. |
| 6,967,673 B2 | 11/2005 | Ozawa et al. |
| 6,979,344 B2 | 12/2005 | Jones et al. |
| 6,986,737 B2 | 1/2006 | Suzuki et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,022,088 B2 | 4/2006 | Haugaard et al. |
| 7,033,387 B2 | 4/2006 | Zadno-azizi et al. |
| 7,036,509 B2 | 5/2006 | Rapacki et al. |
| 7,063,682 B1 | 6/2006 | Whayne et al. |
| 7,100,616 B2 | 9/2006 | Springmeyer |
| 7,112,225 B2 | 9/2006 | Ginn et al. |
| 7,128,747 B2 | 10/2006 | Ginn et al. |
| 7,141,046 B2 | 11/2006 | Perkins et al. |
| 7,165,548 B2 | 1/2007 | Deem et al. |
| 7,175,619 B2 | 2/2007 | Koblish et al. |
| 7,195,017 B2 | 3/2007 | Tanaka |
| 7,198,635 B2 | 4/2007 | Danek et al. |
| 7,300,428 B2 | 11/2007 | Ingenito et al. |
| 7,351,202 B2 | 4/2008 | Long et al. |
| 7,393,330 B2 | 7/2008 | Haugaard et al. |
| 7,393,363 B2 | 7/2008 | Ginn et al. |
| 7,445,010 B2 | 11/2008 | Kugler et al. |
| 7,451,765 B2 | 11/2008 | Adler et al. |
| 7,503,931 B2 | 3/2009 | Kowalsky et al. |
| 7,517,320 B2 | 4/2009 | Wibowo et al. |
| 7,549,984 B2 | 6/2009 | Mathis |
| 7,608,579 B2 | 10/2009 | Gong et al. |
| 7,662,181 B2 | 2/2010 | Deem et al. |
| 7,670,282 B2 | 3/2010 | Mathis |
| 7,670,373 B1 | 3/2010 | Sabanathan et al. |
| 7,731,651 B2 | 6/2010 | Pearce et al. |
| 7,757,691 B2 | 7/2010 | Reynolds et al. |
| 7,766,891 B2 | 8/2010 | McGurk et al. |
| 7,766,895 B2 | 8/2010 | Soltesz et al. |
| 7,766,938 B2 | 8/2010 | McGurk et al. |
| 7,775,968 B2 | 8/2010 | Mathis |
| 7,811,316 B2 | 10/2010 | Kalmann et al. |
| 7,896,008 B2 | 3/2011 | Tanaka |
| 8,142,455 B2 | 3/2012 | Thompson et al. |
| 8,157,823 B2 | 4/2012 | Aronson et al. |
| 8,157,837 B2 | 4/2012 | Thompson et al. |
| 8,282,660 B2 | 10/2012 | Thompson et al. |
| 8,556,954 B2 | 10/2013 | Darvish et al. |
| 8,617,235 B2 | 12/2013 | Schmid et al. |
| 8,632,605 B2 | 1/2014 | Thompson et al. |
| 8,641,753 B2 | 2/2014 | Macatangay et al. |
| 8,668,707 B2 | 3/2014 | Thompson et al. |
| 8,672,996 B2 | 3/2014 | Nelson et al. |
| 8,721,734 B2 | 5/2014 | Mathis et al. |
| 8,740,921 B2 | 6/2014 | Mathis et al. |
| 8,888,800 B2 | 11/2014 | Mathis et al. |
| 8,932,310 B2 | 1/2015 | Thompson et al. |
| 9,402,633 B2 * | 8/2016 | Vasquez ............ A61B 17/12104 |
| 2001/0051799 A1 | 12/2001 | Ingenito |
| 2002/0007831 A1 | 1/2002 | Davenport et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0077593 A1 | 6/2002 | Perkins et al. |
| 2002/0091379 A1 | 7/2002 | Danek et al. |
| 2002/0111620 A1 | 8/2002 | Cooper et al. |
| 2002/0112729 A1 | 8/2002 | Devore et al. |
| 2002/0128647 A1 | 9/2002 | Roschak et al. |
| 2002/0138074 A1 | 9/2002 | Keast et al. |
| 2002/0161392 A1 | 10/2002 | Dubrul |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0018318 A1 | 1/2003 | Melsky et al. |
| 2003/0029452 A1 | 2/2003 | Suki et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0069488 A1 | 4/2003 | Alferness et al. |
| 2003/0070676 A1 | 4/2003 | Cooper et al. |
| 2003/0070682 A1 | 4/2003 | Wilson et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0083692 A1 | 5/2003 | Vrba et al. |
| 2003/0088195 A1 | 5/2003 | Vardi et al. |
| 2003/0100921 A1 | 5/2003 | Addis et al. |
| 2003/0109866 A1 | 6/2003 | Edwards et al. |
| 2003/0127090 A1 | 7/2003 | Gifford et al. |
| 2003/0130657 A1 | 7/2003 | Tom et al. |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito et al. |
| 2003/0181922 A1 | 9/2003 | Alferness |
| 2003/0183235 A1 | 10/2003 | Rimbaugh et al. |

(56) References Cited

U.S. PATENT DOCUMENTS

| | | |
|---|---|---|
| 2003/0191496 A1 | 10/2003 | Edwards et al. |
| 2003/0192551 A1 | 10/2003 | Deem et al. |
| 2003/0195385 A1 | 10/2003 | Devore |
| 2003/0195511 A1 | 10/2003 | Barry et al. |
| 2003/0212337 A1 | 11/2003 | Sirokman et al. |
| 2003/0212412 A1 | 11/2003 | Dillard et al. |
| 2003/0212450 A1 | 11/2003 | Schlick et al. |
| 2003/0233099 A1 | 12/2003 | Danaek et al. |
| 2004/0010209 A1 | 1/2004 | Sirokman et al. |
| 2004/0010289 A1 | 1/2004 | Biggs et al. |
| 2004/0024356 A1 | 2/2004 | Tanaka et al. |
| 2004/0030262 A1 | 2/2004 | Fisher et al. |
| 2004/0031494 A1 | 2/2004 | Danek et al. |
| 2004/0034357 A1 | 2/2004 | Beane et al. |
| 2004/0038868 A1 | 2/2004 | Ingenito et al. |
| 2004/0040555 A1 | 3/2004 | Tanaka et al. |
| 2004/0049187 A1 | 3/2004 | Burnett et al. |
| 2004/0049264 A1 | 3/2004 | Sowinski et al. |
| 2004/0052850 A1 | 3/2004 | Schankereli et al. |
| 2004/0055606 A1 | 3/2004 | Hendricksen et al. |
| 2004/0059263 A1 | 3/2004 | DeVore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073207 A1 | 4/2004 | Ginn |
| 2004/0073241 A1 | 4/2004 | Barry et al. |
| 2004/0078054 A1 | 4/2004 | Biggs et al. |
| 2004/0081676 A1 | 4/2004 | Schankereli et al. |
| 2004/0087886 A1 | 5/2004 | Gellman et al. |
| 2004/0120849 A1 | 6/2004 | Stewart et al. |
| 2004/0133168 A1 | 7/2004 | Salcudean et al. |
| 2004/0134487 A1 | 7/2004 | Deem et al. |
| 2004/0154621 A1 | 8/2004 | Deem et al. |
| 2004/0158228 A1 | 8/2004 | Perkins et al. |
| 2004/0172058 A1 | 9/2004 | Edwards et al. |
| 2004/0176801 A1 | 9/2004 | Edwards et al. |
| 2004/0176833 A1 | 9/2004 | Pavcnik et al. |
| 2004/0210248 A1 | 10/2004 | Gordon et al. |
| 2004/0211434 A1 | 10/2004 | Loomas et al. |
| 2004/0220556 A1 | 11/2004 | Cooper et al. |
| 2004/0225254 A1 | 11/2004 | Tanaka et al. |
| 2004/0231674 A1 | 11/2004 | Tanaka et al. |
| 2004/0234575 A1 | 11/2004 | Horres et al. |
| 2004/0237966 A1 | 12/2004 | Tanaka et al. |
| 2004/0244802 A1 | 12/2004 | Tanaka et al. |
| 2004/0244803 A1 | 12/2004 | Tanaka et al. |
| 2004/0267277 A1 | 12/2004 | Zannis et al. |
| 2005/0004599 A1 | 1/2005 | Mcnally-Heintzelman et al. |
| 2005/0015106 A1 | 1/2005 | Perkins et al. |
| 2005/0016530 A1 | 1/2005 | Mccutcheon et al. |
| 2005/0033310 A1 | 2/2005 | Alferness et al. |
| 2005/0033344 A1 | 2/2005 | Dillard et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0051163 A1 | 3/2005 | Deem et al. |
| 2005/0056292 A1 | 3/2005 | Cooper et al. |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag et al. |
| 2005/0085801 A1 | 4/2005 | Cooper et al. |
| 2005/0096529 A1 | 5/2005 | Cooper et al. |
| 2005/0101836 A1 | 5/2005 | Onuki et al. |
| 2005/0103340 A1 | 5/2005 | Wondka et al. |
| 2005/0107783 A1 | 5/2005 | Tom et al. |
| 2005/0119614 A1 | 6/2005 | Melsky et al. |
| 2005/0131339 A1 | 6/2005 | Makin et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0148902 A1 | 7/2005 | Minar et al. |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178389 A1 | 8/2005 | Shaw et al. |
| 2005/0192526 A1 | 9/2005 | Biggs et al. |
| 2005/0196344 A1 | 9/2005 | McCutcheon et al. |
| 2005/0240277 A1 | 10/2005 | Aliski et al. |
| 2005/0244401 A1 | 11/2005 | Ingenito et al. |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |
| 2005/0281800 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004305 A1 | 1/2006 | George et al. |
| 2006/0004388 A1 | 1/2006 | Whayne et al. |
| 2006/0004400 A1 | 1/2006 | Mcgurk et al. |
| 2006/0009748 A1 | 1/2006 | Mathis |
| 2006/0009801 A1 | 1/2006 | Mcgurk et al. |
| 2006/0020243 A1 | 1/2006 | Speck et al. |
| 2006/0025815 A1 | 2/2006 | McGurk et al. |
| 2006/0029548 A1 | 2/2006 | Pelleg et al. |
| 2006/0030863 A1 | 2/2006 | Fields et al. |
| 2006/0032497 A1 | 2/2006 | Doshi et al. |
| 2006/0076023 A1 | 4/2006 | Rapacki et al. |
| 2006/0095002 A1 | 5/2006 | Soltesz et al. |
| 2006/0100666 A1 | 5/2006 | Wilkinson et al. |
| 2006/0116749 A1 | 6/2006 | Willink et al. |
| 2006/0118126 A1 | 6/2006 | Tanaka et al. |
| 2006/0124126 A1 | 6/2006 | Tanaka et al. |
| 2006/0135947 A1 | 6/2006 | Soltesz et al. |
| 2006/0135984 A1 | 6/2006 | Kramer et al. |
| 2006/0162731 A1 | 7/2006 | Wondka et al. |
| 2006/0167416 A1 | 7/2006 | Mathis et al. |
| 2006/0184016 A1 | 8/2006 | Glossop et al. |
| 2006/0200076 A1 | 9/2006 | Gonzalez et al. |
| 2006/0206147 A1 | 9/2006 | DeVore et al. |
| 2006/0235432 A1 | 10/2006 | DeVore et al. |
| 2006/0235467 A1 | 10/2006 | DeVore et al. |
| 2006/0249164 A1 | 11/2006 | Springmeyer et al. |
| 2006/0264772 A1 | 11/2006 | Aljuri et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2006/0283462 A1 | 12/2006 | Fields et al. |
| 2007/0005083 A1 | 1/2007 | Sabanathan et al. |
| 2007/0096048 A1 | 5/2007 | Clerc et al. |
| 2007/0185572 A1 | 8/2007 | Solem et al. |
| 2008/0036763 A1 | 2/2008 | Chen et al. |
| 2008/0063693 A1 | 3/2008 | Cook et al. |
| 2008/0161865 A1 | 7/2008 | Hagen |
| 2008/0183204 A1 | 7/2008 | Greenhalgh et al. |
| 2008/0200797 A1 | 8/2008 | Kotmel et al. |
| 2008/0262473 A1 | 10/2008 | Kornblau et al. |
| 2009/0012626 A1 | 1/2009 | Thompson et al. |
| 2009/0076526 A1 | 3/2009 | Rousseau et al. |
| 2009/0104183 A1 | 4/2009 | Gong et al. |
| 2009/0221967 A1 | 9/2009 | Thommen et al. |
| 2009/0306644 A1 | 12/2009 | Mayse et al. |
| 2010/0070050 A1 | 3/2010 | Mathis et al. |
| 2010/0297218 A1 | 11/2010 | Gong et al. |
| 2012/0071719 A1 | 3/2012 | Shanley et al. |
| 2012/0123514 A1 | 5/2012 | Kunis et al. |
| 2012/0172909 A1 | 7/2012 | Mathis et al. |
| 2012/0192872 A1 | 8/2012 | Rudakov et al. |
| 2013/0103059 A1 | 4/2013 | Mathis et al. |
| 2013/0217956 A1 | 8/2013 | Thompson et al. |
| 2014/0188246 A1 | 7/2014 | Aronson et al. |
| 2014/0371705 A1 | 12/2014 | Thompson et al. |
| 2015/0051709 A1 | 2/2015 | Vasquez et al. |

(56) References Cited

U.S. PATENT DOCUMENTS

| | | | |
|---|---|---|---|
| 2015/0057695 A1 | 2/2015 | Mathis et al. | |
| 2015/0073563 A1 | 3/2015 | Mathis et al. | |
| 2015/0080934 A1 | 3/2015 | Aronson et al. | |

FOREIGN PATENT DOCUMENTS

| | | |
|---|---|---|
| JP | 10005343 | 1/1998 |
| JP | 2005287568 | 10/2005 |
| WO | 9401508 | 1/1994 |
| WO | 9801084 | 1/1998 |
| WO | 9823227 | 4/1998 |
| WO | 0013592 | 3/2000 |
| WO | 0113839 | 3/2001 |
| WO | 0154618 | 8/2001 |
| WO | 0200270 | 1/2002 |
| WO | 0200275 | 1/2002 |
| WO | 0202158 | 1/2002 |
| WO | 0249554 | 6/2002 |
| WO | 03005709 | 1/2003 |
| WO | 03028522 | 4/2003 |
| WO | 03057079 | 7/2003 |
| WO | 03077768 | 9/2003 |
| WO | 0249544 | 4/2004 |
| WO | 2004049970 | 6/2004 |
| WO | 2004062505 | 7/2004 |
| WO | 2004080347 | 9/2004 |
| WO | 2004086977 | 10/2004 |
| WO | 2005058206 | 6/2005 |
| WO | 2005122870 | 12/2005 |
| WO | 2007016409 | 2/2007 |
| WO | 2007106495 | 9/2007 |
| WO | 2008036763 | 3/2008 |
| WO | 2010022173 | 2/2010 |
| WO | 2014151557 | 9/2014 |

OTHER PUBLICATIONS

"Medical ventilator", Wikipedia. Downloaded from <http://en.wikipedia.org/wiki/Medical_ventilator> on Jan. 16, 2015, Jan. 16, 2015.

Hermanson, "Bioconjugation Techniques", Academic Press, New York, 1996, 3 pages.

Lam et al., "X-Ray Diagnosis: A Physician's Approach", Singapore: Springer, 1998, 6 pages.

O'Brien et al., "Improvements in Lung Function, Exercise, and Quality of Life in Hypercapnic COPD Patients After Lung Volume", Chest, vol. 115, 1999, pp. 75-84.

Quint et al., "Diaphragmetic Shape Change After Lung Volume Reduction Surgery", Journal of Thoracic Imaging 16, 2001, pp. 149-155.

Rowe et al., Handbook of Pharmaceutical Excipients. 4th Edition. London: Pharmaceutical Press, 2003, 6 pages.

Slone et al., "Body CT: A Practical Approach", New York: McGraw-Hill, 2000, 4 pages.

Stout et al., "X-Ray Structure Determination: A Practical Guide", John Wiley & Sons 2nd Edition, 1989, 9 pages.

Yusen et al., "A Prospective Evaluation of Lung Volume Reduction Surgery in 200 Consecutive Patients", Chest, vol. 123(4), Apr. 2003, pp. 1026-1037.

* cited by examiner

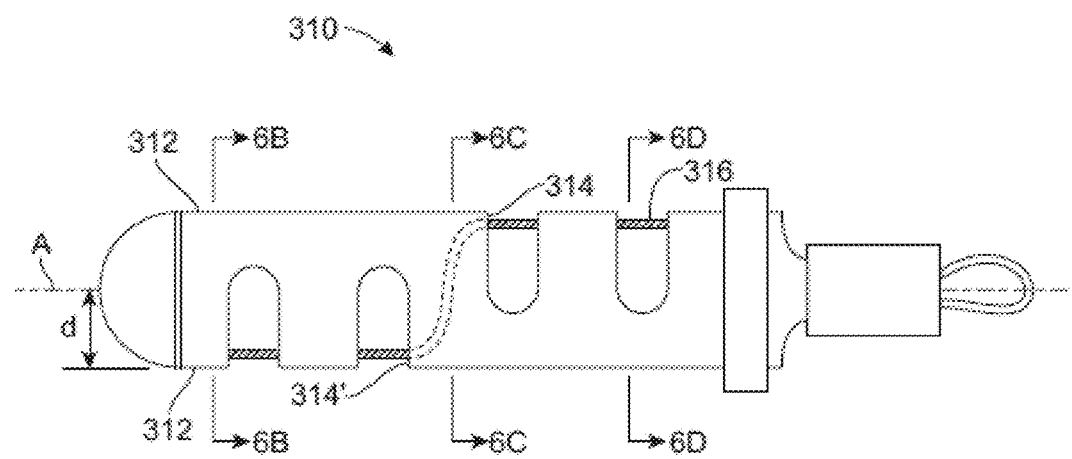
FIG. 5A
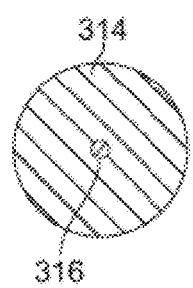 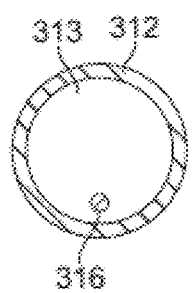 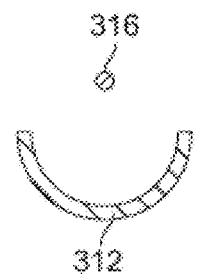
FIG. 5B  FIG. 5C  FIG. 5D

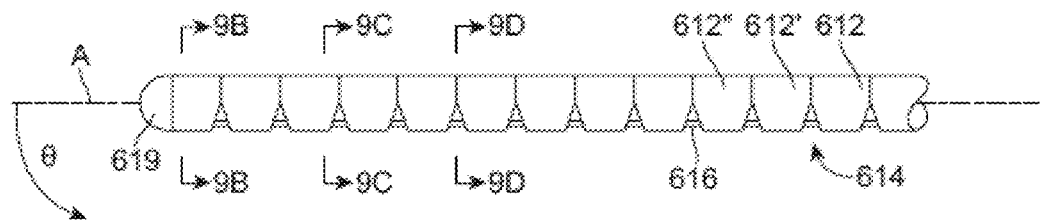
FIG. 8A
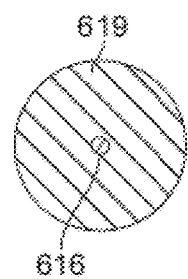
FIG. 8B
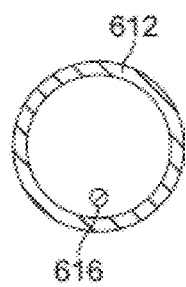
FIG. 8C
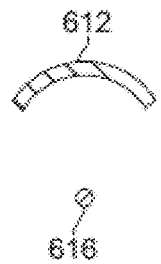
FIG. 8D
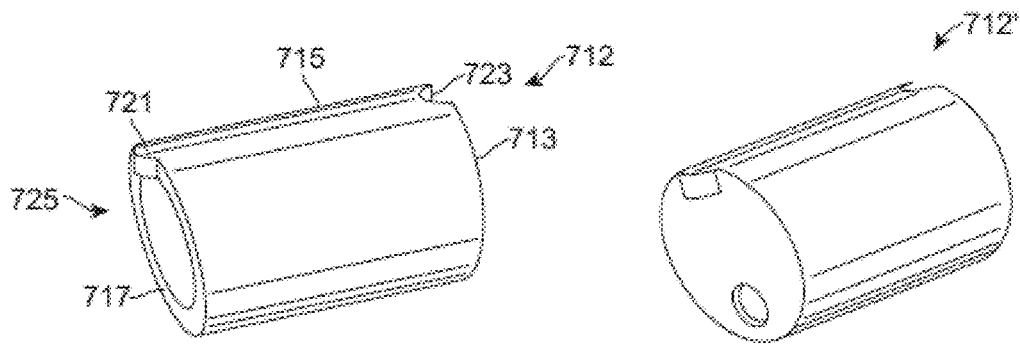
FIG. 9A
FIG. 9B

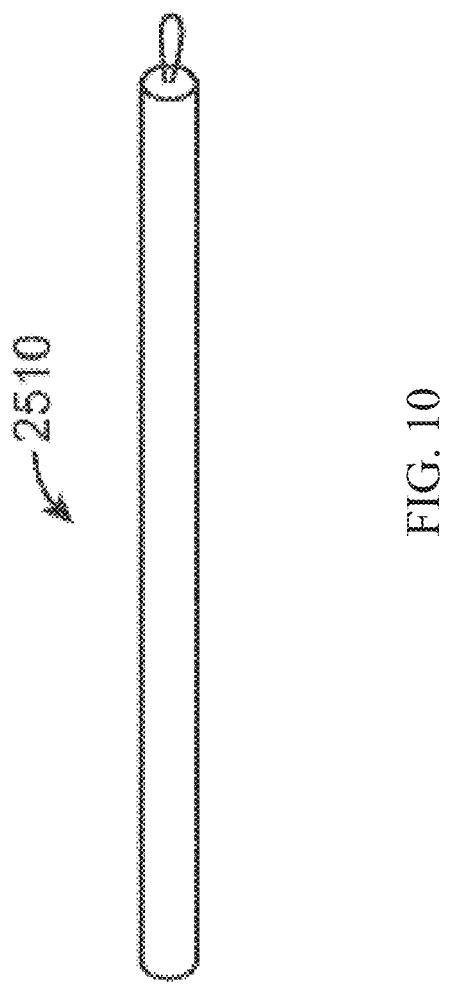

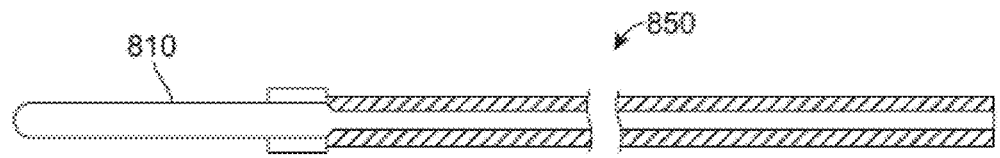
FIG. 13A
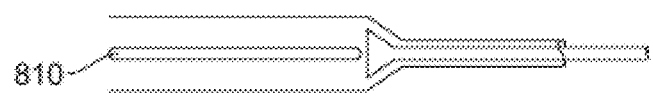
FIG. 13B
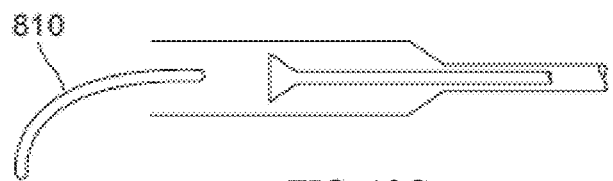
FIG. 13C
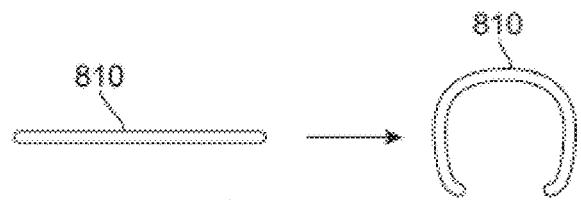
FIG. 13D
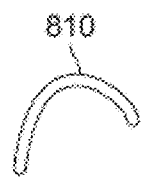
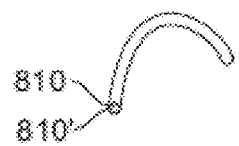
FIG. 13E              FIG. 13F

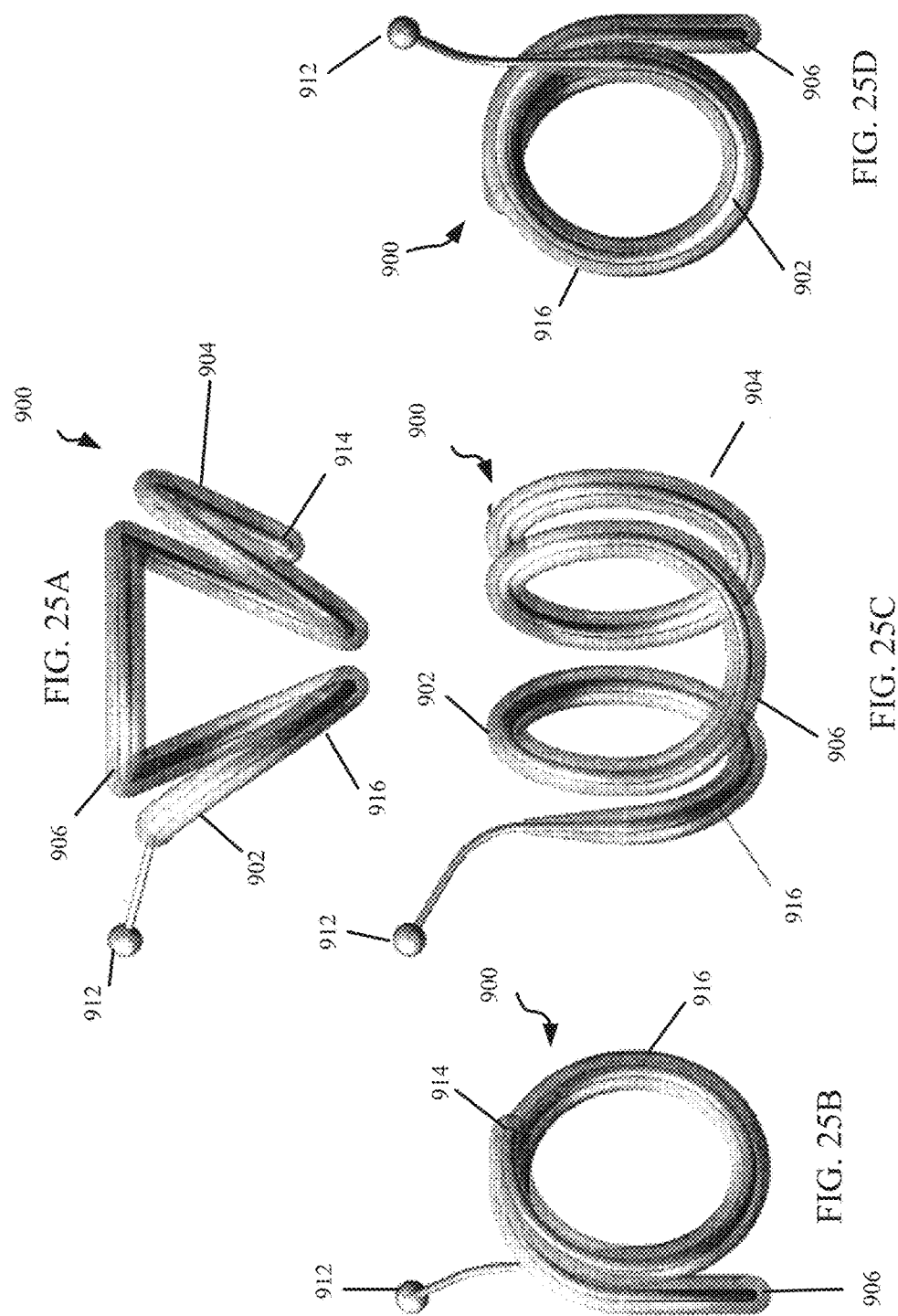

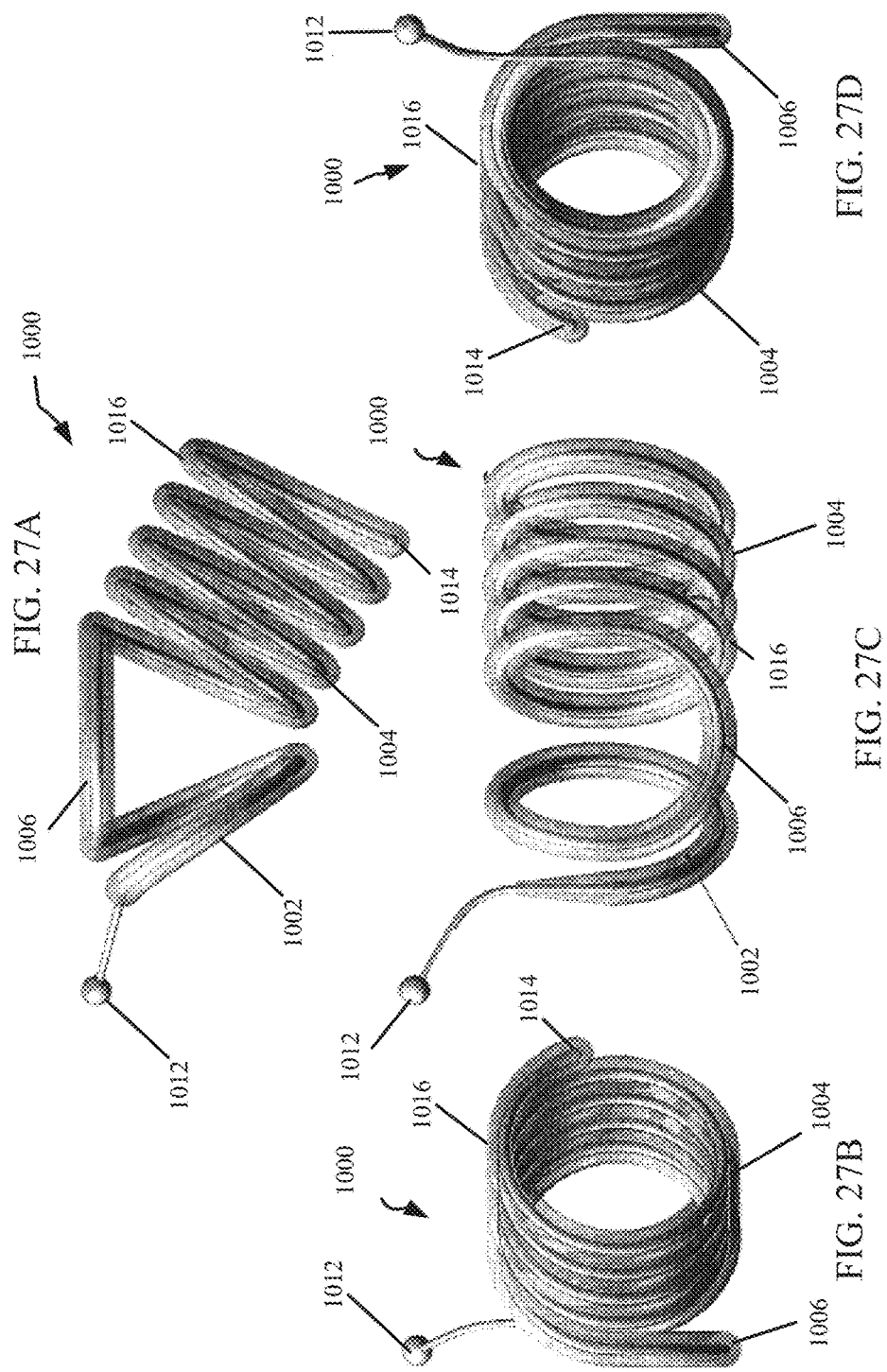

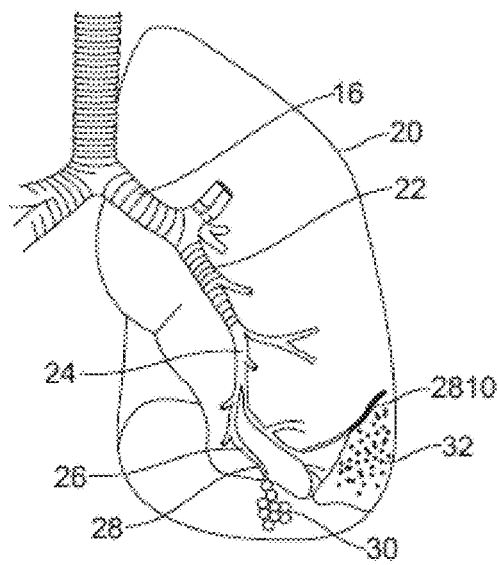
FIG. 32A
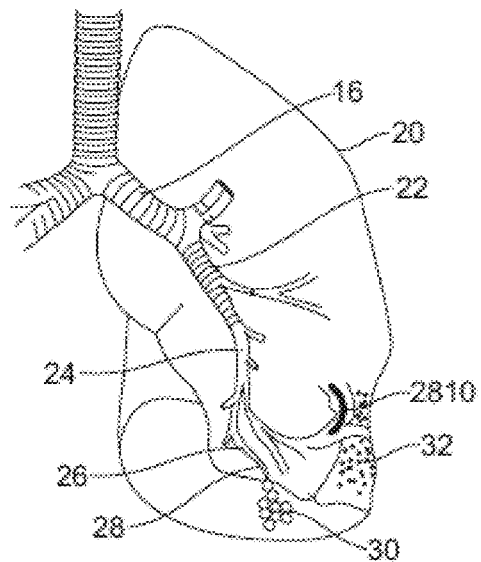 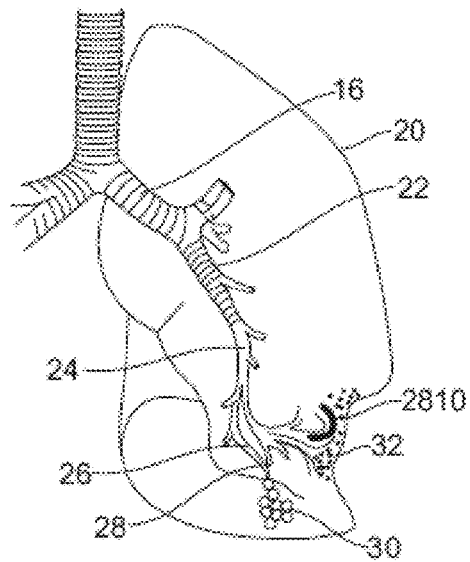
FIG. 32B    FIG. 32C

TORQUE ALLEVIATING INTRA-AIRWAY LUNG VOLUME REDUCTION COMPRESSIVE IMPLANT STRUCTURES

CROSS-REFERENCES TO RELATED APPLICATIONS

The present application is a Continuation of Ser. No. 14/209,194 filed Mar. 13, 2014 (Allowed); which claims the benefit of U.S. Provisional Appln No. 61/791,517 filed Mar. 15, 2013; the full disclosures which are incorporated herein by reference in their entirety for all purposes.

This application is generally related to U.S. Ser. No. 12/782,515 filed May 18, 2010 (now U.S. Pat. No. 8,721,734), entitled Cross-Sectional Modification During Deployment of an Elongate Lung Volume Reduction Device; which claims the benefit of U.S. Provisional Appln No. 61/179,306 filed May 18, 2009; each of which are incorporated herein by reference in their entirety.

This application is also generally related to U.S. Ser. No. 12/167,167 filed Jul. 2, 2008 (now U.S. Pat. No. 8,282,660), entitled Minimally Invasive Lung Volume Reduction Devices, Methods, and Systems; which is a Continuation of PCT Patent Application No. PCT/US07/06339 filed Mar. 13, 2007; which is a Continuation-in-Part of U.S. Ser. No. 11/422,047 filed Jun. 2, 2006 (now U.S. Pat. No. 8,157,837), entitled Minimally Invasive Lung Volume Reduction Device and Method; each of which are incorporated herein by reference in their entirety.

This application is also generally related to U.S. Provisional Patent Applns 60/743,471 filed Mar. 13, 2006, entitled Minimally Invasive Lung Volume Reduction Device and Method; 60/884,804 filed Jan. 12, 2007, entitled Minimally Invasive Lung Volume Reduction Devices, Methods and Systems; and 60/885,305 filed Jan. 17, 2007, entitled Minimally Invasive Lung Volume Reduction Devices, Methods and Systems, each of which are incorporated herein in their entirety.

This application is also generally related to U.S. Ser. No. 12/209,631 (now U.S. Pat. No. 8,142,455), entitled Delivery of Minimally Invasive Lung Volume Reduction Devices; Ser. No. 12/209,662 (now U.S. Pat. No. 8,157,823), entitled Improved Lung Volume Reduction Devices, Methods and Systems, both of which were filed Sep. 12, 2008; and to Ser. No. 12/558,206, entitled Improved and/or Longer Lung Volume Reduction Devices, Methods, and Systems; and Ser. No. 12/558,197 (now U.S. Pat. No. 8,632,605), entitled Elongated Lung Volume Reduction Devices, Methods, and Systems, each of which were filed Sep. 11, 2009; all of which are incorporated herein by reference in their entirety.

All publications and patent applications mentioned in this specification are herein incorporated by reference to the same extent as if each individual publication or patent application was specifically and individually indicated to be incorporated by reference.

BACKGROUND OF THE INVENTION

Field of the Invention

Devices, systems and methods are described for treating lungs. The exemplary devices, systems and methods may, for example, improve the quality of life and restore lung function for patients suffering from emphysema. Embodiments of the systems may include an implant and a delivery catheter. The implant may be advanced through tortuous anatomy and actuated to retain a pre-determined shape and rigidity. Additionally, the implant may comprise a shape-memory material or spring material, which may be constrained to a first configuration during delivery through tortuous anatomy and then allowed to return to a second configuration during deployment. The deployed implant modifies the shape of the airways and locally compresses lung parenchyma to cause volume reduction and thereby tensions the lung parenchyma to restore elastic recoil. Systems and devices are also included that deploy and actuate the implantable devices, as well as systems and devices designed for recapture of the implanted device.

Current medical literature describes emphysema as a chronic (long-term) lung disease that can get worse over time. It's usually caused by smoking. Having emphysema means some of the air sacs in your lungs are damaged, making it hard to breathe. Some reports indicate that emphysema is the fourth largest cause of mortality in the U.S., affecting an estimated 16-30 million U.S. citizens. Each year approximately 100,000 sufferers die of the disease. Smoking has been identified as a major cause, but with ever increasing air pollution and other environmental factors that negatively affect pulmonary patients; the number of people affected by emphysema is on the rise.

A currently available solution for patients suffering from emphysema is a surgical procedure called Lung Volume Reduction (LVR) surgery whereby diseased lung is resected and the volume of the lung is reduced. This allows healthier lung tissue to expand into the volume previously occupied by the diseased tissue and allows the diaphragm to recover. High mortality and morbidity may be associated with this invasive procedure. Several minimally invasive investigational therapies exist that aim at improving the quality of life and restoring lung function for patients suffering from emphysema. These potential therapies include mechanical devices and biological treatments. The Zephyr™ device by Emphasys (Redwood City Calif.) and the IBV™ device by Spiration (Redmond Wash.) are mechanical one way valve devices. The underlying theory behind these devices is to achieve absorptive atelectasis by preventing air from entering diseased portion of the lung, while allowing air and mucous to pass through the device out of the diseased regions. The Watanabe spigot is another mechanical device that can seek to completely occlude the airway, thereby preventing air from entering and exiting the lung. Collateral ventilation (interlobar and intralobar—porous flow paths that prevent complete occlusion) may prevent atelectasis for such devices. The lack of atelectasis or lung volume reduction can drastically reduce the effectiveness of such devices. Other mechanical devices include means of deploying anchors into airways and physically deforming airways by drawing the anchors together via cables.

Biological treatments utilize tissue engineering aimed at causing scarring at specific locations. Unfortunately, it can be difficult to control the scarring and to prevent uncontrolled proliferation of scarring.

SUMMARY OF THE INVENTION

The present invention generally provides improved medical devices, systems, and methods, particularly for treating one or both lungs of a patient. Embodiments of the invention often make use of elongate implant structures which can be introduced into an airway system to a target airway axial region. The target axial region may or may not include branches, and the implants can be deployed within the airway by bending or allowing the implant to bend so that the implant compresses adjacent lung tissue. Many embodiments may apply lateral bending and/or compression forces against the lung tissue from within the airways for an extended period of time. Exemplary embodiments may be placed in the lung to increase gas filling resistance in the portion of the lung. Optionally, embodiments may be deployed within the lung to uncollapse previously collapsed airways or blood vessels. Embodiments may comprise a spring or shape memory material which is delivered within a catheter in a delivery configuration to the target airway and then released from the catherter to return to a deployed configuration within the airway. Exemplary embodiments may have a configuration which provides a more controlled transition from the delivery configuration to the deployed configuration during the release of the device from the catheter. In some embodiments, a proximal end of the device may be configured to facilitate recapture of the device after the device is deployed within the lung. This may be beneficial when the device is deployed in a less than ideal position or orientation or when the implant is no longer deamed necessary.

Exemplary embodiments include structures or features which may inhibit tissue reactions that might otherwise allow portions of the device to eventually traverse through the wall of the airway. Many embodiments of the elongate devices may enhance the support area bearing laterally on the tissue of a surrounding airway lumen wall, particularly along a length of the device between a proximal end of the device and a distal end of the device. Embodiments may have features which increase the device friction with the airway to allow the device to grip the surrounding airway as the device is deployed. This may help prevent the device from longitudinally sliding within the airway and may increase gathering of the damaged lung tissue together in compression. Maintaining the device within the airway may facilitate recapture of the device (either in the delivery catheter or after full deployment and the device has been implanted, optionally using a separate device to capture the implant with a separate grasper) and successfully pull the device out of the lung. By infusing an appropriate adhesive around the device in the lung, ideally by infusing a Pneu-Seal™ albumin-glutaraldehyde adhesive, the device may be recaptured by pulling the device out of the sealant. To minimize or inhibit inflammation to the tissue, the device should comprise materials that are biocompatible and generally rounded such that micro motion between the device and airway don't cause an acceleration of tissue degradation. Contact with the device may advantageously induce beneficial tissue thickening. Features which induce some tissue ingrowth (stimulation of tissue growth) so the tissue foundation is thickened and the device is better supported can also be beneficial.

In embodiments of the present invention, a lung volume reduction system for enhancing a breathing efficiency of a patient with an airway is provided. The system may include an implantable device configured to impart a compression force on lung tissue. The implantable device may include a proximal end and a distal end and may further have a first configuration and a second configuration. The second configuration of the implantable device may correspond to a configuration of the implantable device pre-implantation or post-implantation. The second configuration may comprise at least two helical sections (sometimes referred to herein as coil sections) with a transition section disposed between the at least two helical sections. Optionally, the at least two helical sections comprise a right-handed helical section and a left-handed helical section. Further the transition section disposed between the at least two helical sections may comprises a switchback transition section when the implantable device is in the second configuration. In some embodiments, at least one of the at least two helical sections comprise a circular helical section when the implantable device is in the second configuration. Optionally, both of the at least two helical sections comprise circular helical sections when the implantable device is in the second configuration.

In some embodiments, the implantable device may further comprise a jacket which covers a portion of the implantable device. The jacket may be configured to reduce erosion into the airway by a deployed implantable device. The jacket may cover the at least two helical sections and the transition section disposed between the at least two helical sections. The jacket may also cover the distal end of the implantable device. Optionally, the jacket may comprise a polycarbonate urethane material. The polycarbonate material may have at least 55D hardness.

In some embodiments, the distal end of the implantable device may include an anchor for coupling with the airway. Optionally, the proximal end of the implantable device may be atraumatic. Preferably, the proximal end of the implantable device comprises a stand-off proximal tail which extends away from each axis of the at least two helical sections when the implant is in the second configuration. In some embodiments, the at least two helical sections have a first and second axis, respectively, and the first and second axes are different when the implantable device is in the second configuration. The first and second axes may form an angle ranging between 190° and 230° when the implantable device is in the second configuration. Optionally, the implantable device comprises a spring element. The implantable device may comprise a metal including nickel and titanium. In some embodiments, the distal helical section may comprise more loops (i.e., complete helix turns) than the proximal helical section when the implantable device is in the second configuration. In some embodiments the proximal helical section may comprise less than two loops when the implantable device is in the second configuration. Optionally, the distal helical section comprises at least one loop when the implantable device is in the second configuration. In some embodiments, the distal helical section may comprise at least four loops when the implantable device is in the second configuration.

Some embodiments of the present invention provide a lung volume reduction device for enhancing a breathing efficiency of a patient with an airway. The device may include a proximal end and a distal end; and the device may include a first configuration and a second configuration where the first configuration corresponds to a delivery configuration and the second configuration corresponds to a pre-implantation configuration or a post-implantation configuration. The second configuration of the device may comprise a first helical section with an axis and the first helical section may be disposed between the proximal end and the distal end of the device. The proximal end may extend away from the axis of the first helical section when the device is in the second configuration. The second configuration may further comprise a second helical section coupled with the first helical section. The first helical section and second helical section may comprise a right-handed helical section and a left-handed helical section when the device is in the second configuration. The proximal end may extend away from the axis of the second helical section when the device is in the second configuration.

In some embodiments of the lung volume reduction device, the more distal helical section may comprise more loops than the more proximal helical section when the device is in the second configuration. Optionally, the axis of the second helical section may be different than the axis of the first helical section when the device is in the second configuration. The device may further comprise a jacket covering at least the distal end and the first helical section. The jacket may comprise polycarbonate urethane material having a hardness of at least 55D.

In yet another embodiment of the present invention, a method of enhancing a breathing efficiency of a patient with a lung having an airway is provided. The method may comprise advancing an implant distally through the airway to a portion of the lung of the patient while the implant is in a delivery configuration; the implant having a proximal end and a distal end. Thereafter, the device may be deployed in the portion of the lung by transitioning the implant from the delivery configuration to a deployed configuration; the deployed configuration of the implant comprising at least two helical sections with a transition section disposed between the at least two helical sections. The at least two helical sections may comprise a right-handed helical section and a left-handed helical section and the transition section disposed between the at least two helical sections may comprise a switchback transition section when the implant is in the deployed configuration. At least one of the at least two helical sections may comprise a circular helical section when the implantable device is in the deployed configuration. Optionally, both of the at least two helical sections comprise circular helical sections when the implant is in the deployed configuration. In some embodiments, the implant may further comprise a jacket which covers a portion of the implant. The jacket may be configured to reduce implant erosion into the airway after the implant is deployed within the lung. The jacket may cover the at least two helical sections and the transition section disposed between the at least two helical sections. The jacket may also cover the distal end of the implant. Preferably, the jacket comprises a polycarbonate urethane material having at least 55D hardness.

The distal end of the implant may include an anchor for coupling with the airway. The implant may be deployed in the portion of the lung by coupling the distal end of the implant to the lung tissue with the anchor before or during the transition of the implant from the delivery configuration to the deployed configuration. The proximal end of the implant may be atraumatic. The proximal end of the implant may also comprise a stand-off proximal tail. The stand-off proximal tail may extend away from each axis of the at least two helical sections when the implant is in the deployed configuration. The at least two helical sections may have a first and second axis, respectively, and the first and second axes may be different when the implant is in the deployed configuration. For example, the first and second axes may form an angle ranging between 190° and 230° when the implant is in the deployed configuration. The implant may comprise a spring element and the implant may be constrained to the delivery configuration during delivery. Optionally, the implant may be configured to naturally recover from the constrained delivery configuration to the deployed configuration during deployment. The implant may comprise a metal including nickel and titanium. The distal helical section may comprise more loops than the proximal helical section when the implant is in the deployed configuration. In some embodiments, the proximal helical section comprises less than two loops when the implant is in the deployed configuration. The distal helical section may comprise at least one loop when the implant is in the deployed configuration. In some embodiments, the distal helical section may comprise at least four loops when the implant is in the deployed configuration.

In yet another embodiment of the present invention, another method of enhancing a breathing efficiency of a patient with a lung having an airway is provided. The method may comprise advancing an implant distally through the airway to a portion of the lung of the patient while the implant is in a delivery configuration; the implant having a proximal end and a distal end. Thereafter, the method may include deploying the implant in the portion of the lung by transitioning the implant from the delivery configuration to a deployed configuration, the deployed configuration of the implant comprising a first helical section with an axis, the first helical section disposed between the proximal end and the distal end of the device, and wherein the proximal end extends away from the axis of the first helical section when the device is in the deployed configuration.

The deployed configuration may further comprise a second helical section with an axis and the second helical section may be coupled with the first helical section. The first helical section and second helical section may comprise a right-handed helical section and a left-handed helical section when the implant is in the deployed configuration. The proximal end may extend away from the axis of the second helical section when the implant is in the deployed configuration.

The more distal helical section may comprise more loops than the more proximal helical section when the implant is in the deployed configuration. Optionally, the axis of the second helical section is different than the axis of the first helical section when the device is in the deployed configuration. The implant may further comprise a jacket covering at least the distal end and the first helical section. The jacket may comprise a polycarbonate urethane material having a hardness of at least 55D.

BRIEF DESCRIPTION OF THE DRAWINGS

A better understanding of the features and advantages of the present invention will be obtained by reference to the attached documents that set forth illustrative embodiments, in which the principles of the invention are utilized, and the accompanying drawings of which:

FIGS. 5A-5D illustrate a lung volume reduction device according to another aspect of the invention;

FIGS. 8A-8D illustrate a lung volume reduction device according to another aspect of the invention;

FIGS. 9A-9B illustrate segments suitable for use in configuring a lung volume reduction device according to an aspect of the invention;

FIG. 10 illustrates an exemplary device in a pre-deployed condition according to aspects of the invention;

FIGS. 13A-13F illustrate a plurality of individual wires formed of shape memory material that can be deployed to form a lung volume reduction device and a delivery device;

FIGS. 25A-25D illustrate the device of FIGS. 24A-E further comprising a jacket;

FIGS. 27A-27D illustrate the device of FIGS. 26A-E further comprising a jacket;

FIGS. 32A-32C illustrate a device implanted within the lungs;

DETAILED DESCRIPTION OF THE INVENTION

Figure 1A:
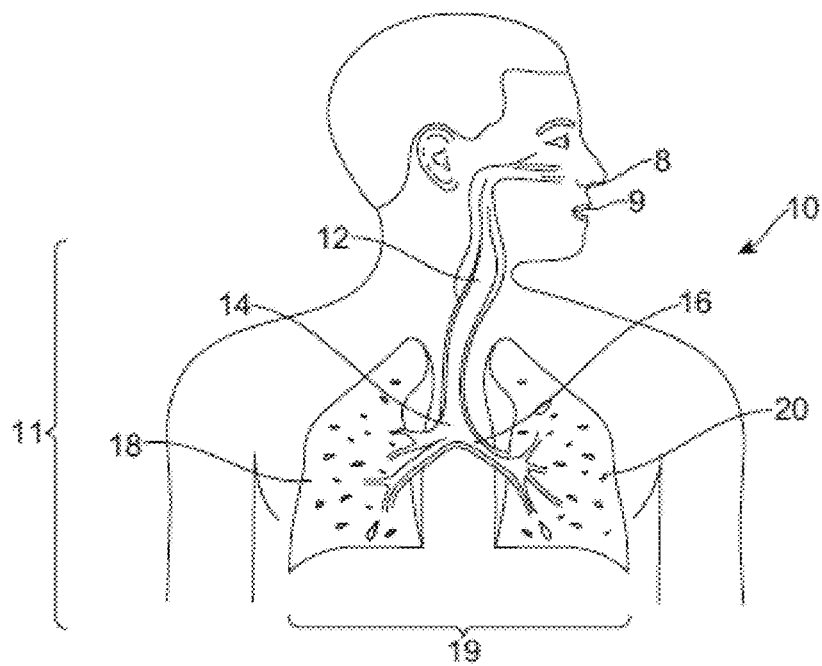
FIGS. 1A-1C illustrates the anatomy of the respiratory system.

By way of background and to provide context for the invention, FIG. 1A illustrates the respiratory system 10 located primarily within a thoracic cavity 11. This description of anatomy and physiology is provided in order to facilitate an understanding of the invention. Persons of skill in the art will appreciate that the scope and nature of the invention is not limited by the anatomy discussion provided. Further, it will be appreciated there can be variations in anatomical characteristics of an individual, as a result of a variety of factors, which are not described herein. The respiratory system 10 includes the trachea 12, which brings air from the nose 8 or mouth 9 into the right primary bronchus 14 and the left primary bronchus 16. From the right primary bronchus 14 the air enters the right lung 18; from the left primary bronchus 16 the air enters the left lung 20. The right lung 18 and the left lung 20 together comprise the lungs 19. The left lung 20 is comprised of only two lobes while the right lung 18 is comprised of three lobes, in part to provide space for the heart typically located in the left side of the thoracic cavity 11, also referred to as the chest cavity.

Figure 1B:
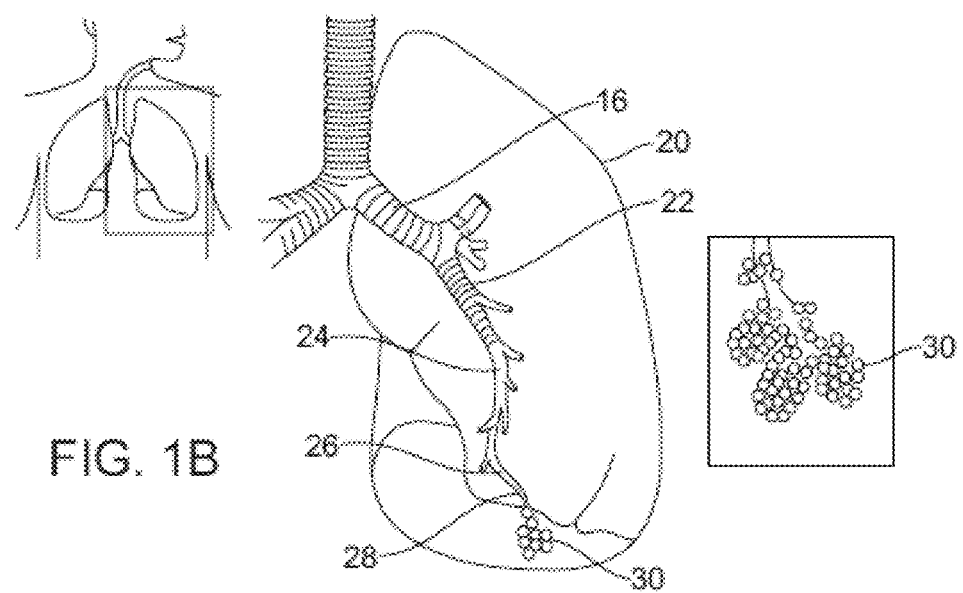
Figure 1C:
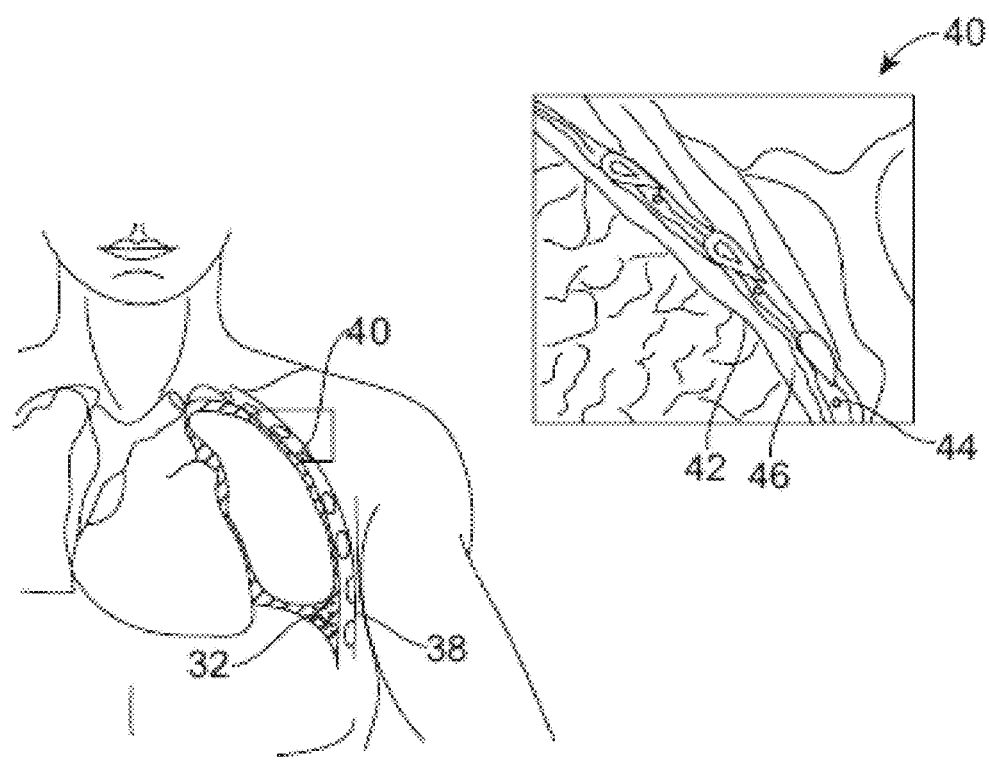
Figure 2A:
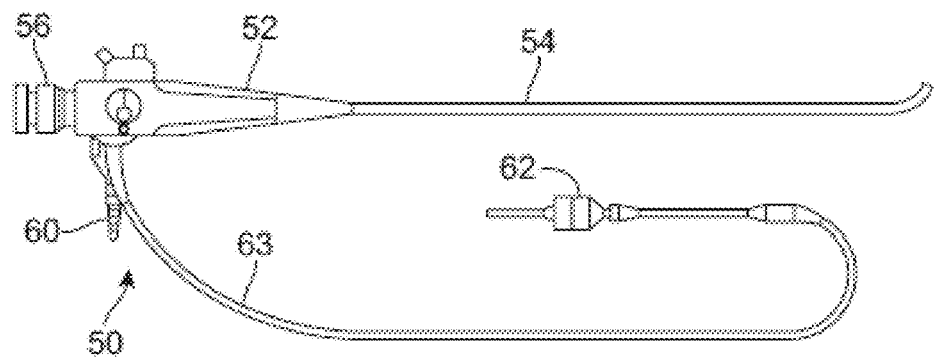
FIGS. 2A-2D illustrate a bronchoscope.
Figure 2B:
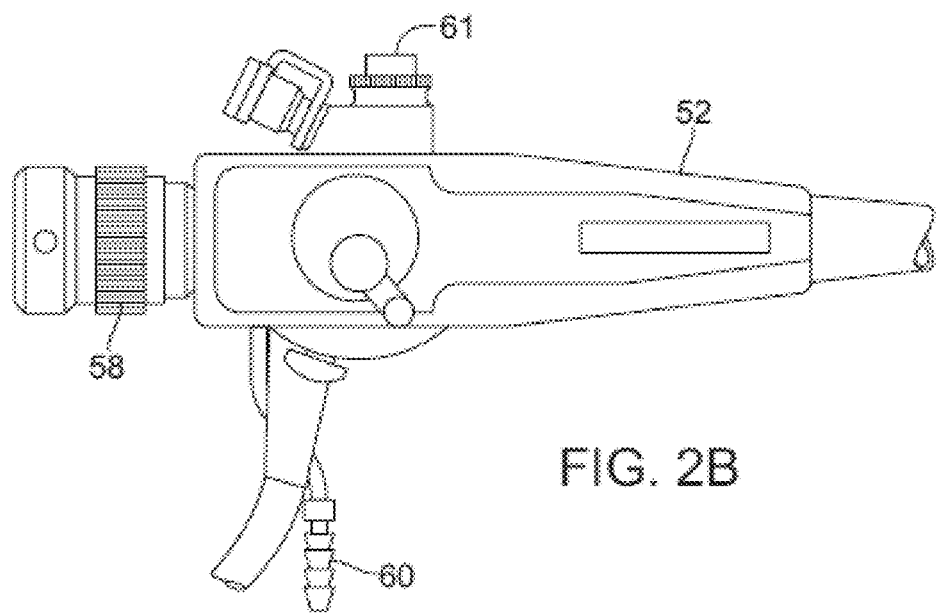
Figure 2C:
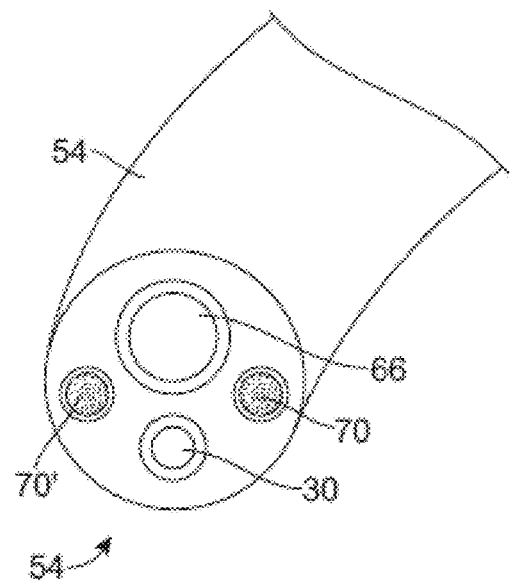
Figure 2D:
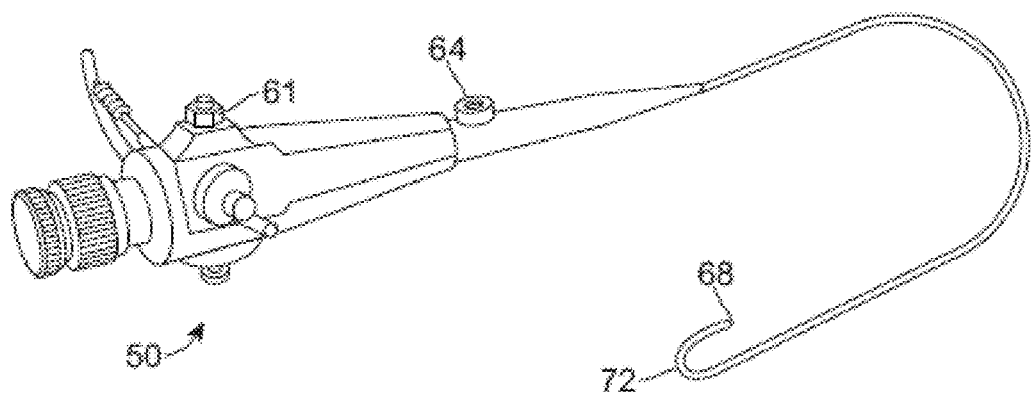

As shown in more detail in FIG. 1B, the primary bronchus, e.g. left primary bronchus 16, that leads into the lung, e.g. left lung 20, branches into secondary bronchus 22, and then further into tertiary bronchus 24, and still further into bronchioles 26, the terminal bronchiole 28 and finally the alveoli 30. The pleural cavity 38 is the space between the lungs and the chest wall. The pleural cavity 38, shown in FIG. 1C, protects the lungs 19 and allows the lungs to move during breathing. Also shown in FIG. 1C, the pleura 40 defines the pleural cavity 38 and consists of two layers, the visceral pleurae 42 and the parietal pleurae 44, with a thin layer of pleural fluid therebetween. The space occupied by the pleural fluid is referred to as the pleural space 46. Each of the two pleurae layers 42, 44, are comprised of very porous mesenchymal serous membranes through which small amounts of interstitial fluid transude continually into the pleural space 46. The total amount of fluid in the pleural space 46 is typically slight. Under normal conditions, excess fluid is typically pumped out of the pleural space 46 by the lymphatic vessels.

The lungs 19 are described in current literature as an elastic structure that floats within the thoracic cavity 11. The thin layer of pleural fluid that surrounds the lungs 19 lubricates the movement of the lungs within the thoracic cavity 11. Suction of excess fluid from the pleural space 46 into the lymphatic channels maintains a slight suction between the visceral pleural surface of the lung pleura 42 and the parietal pleural surface of the thoracic cavity 44. This slight suction creates a negative pressure that keeps the lungs 19 inflated and floating within the thoracic cavity 11. Without the negative pressure, the lungs 19 collapse like a balloon and expel air through the trachea 12. Thus, the natural process of breathing out is almost entirely passive because of the elastic recoil of the lungs 19 and chest cage structures. As a result of this physiological arrangement, when the pleura 42, 44 is breached, the negative pressure that keeps the lungs 19 in a suspended condition disappears and the lungs 19 collapse from the elastic recoil effect.

When fully expanded, the lungs 19 completely fill the pleural cavity 38 and the parietal pleurae 44 and visceral pleurae 42 come into contact. During the process of expansion and contraction with the inhaling and exhaling of air, the lungs 19 slide back and forth within the pleural cavity 38. The movement within the pleural cavity 38 is facilitated by the thin layer of mucoid fluid that lies in the pleural space 46 between the parietal pleurae 44 and visceral pleurae 42. As discussed above, when the air sacs in the lungs are damaged 32, such as is the case with emphysema, it is hard to breathe. Thus, isolating the damaged air sacs to improve the elastic structure of the lung improves breathing. Similarly, locally compressing regions of the lung tissue while maintaining an overall volume of the lung increases tension in other portions of the lung tissue, which can increase the overall lung function.

A conventional flexible bronchoscope is described in U.S. Pat. No. 4,880,015 to Nierman for Biopsy Forceps. As shown in FIGS. 2A-D, bronchoscope 50 can be configured to be of any suitable length, for example, measuring 790 mm in length. The bronchoscope 50 can further be configured from two main parts, a working head 52 and an insertion tube 54. The working head 52 contains an eyepiece 56; an ocular lens with a diopter adjusting ring 58; attachments for the suction tubing 60 and a suction valve 61 and for the cold halogen light source 62 and 63; and an access port or biopsy inlet 64, through which various devices and fluids can be passed into the working channel 66 and out the distal end of the bronchoscope. The working head is attached to the insertion tube, which typically measures 580 mm in length and 6.3 mm in diameter. The insertion tube can be configured to contain fiberoptic bundles (which terminate in the objective lens 30 at the distal tip 68), two light guides 70, 70' and the working channel 66. The distal end of the bronchoscope has the ability to bend 72 anterior and posterior, with the exact angle of deflection depending on the instrument used. A common range of bending is from 160 degrees forward to 90 degrees backward, for a total of 250 degrees. Bending may be controlled by the operator by adjusting an angle lock lever and angulation lever on the working head. See also, U.S. Patent Pub. US 2005/0288550 A1 to Mathis for Lung Access Device and US 2005/0288549 A1 to Mathis for Guided Access to Lung Tissue, the entirety of which is incorporated herein by reference.

Figure 3:
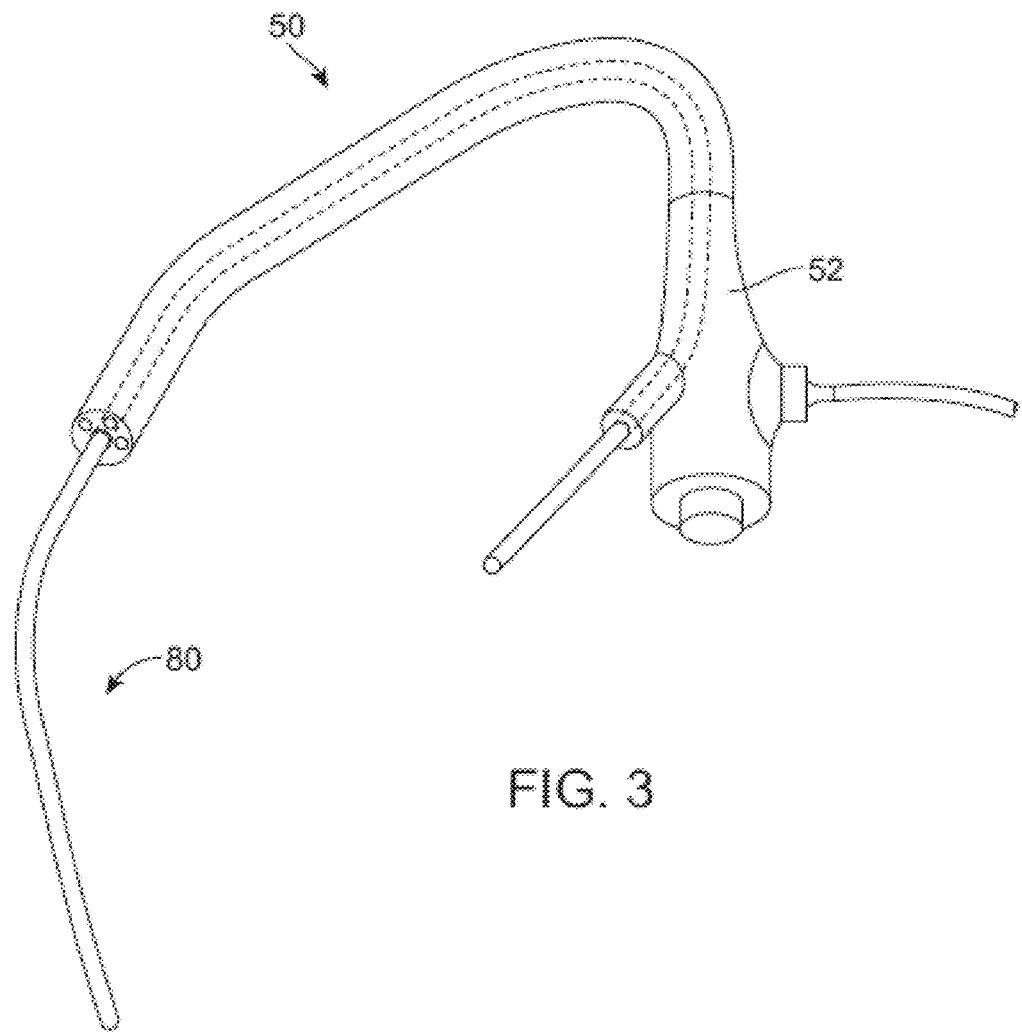
FIG. 3 illustrates a bronchoscope in combination with a delivery device for a lung volume reduction device according to the invention.

FIG. 3 illustrates the use of a lung volume reduction delivery device 80 for delivering a lung volume reduction device comprising an implantable device with the bronchoscope 50. The lung volume reduction system, as described in further detail below, is adapted and configured to be delivered to a lung airway of a patient in a delivery configuration and then transitioned to a deployed configuration. By deploying the device, tension can be applied to the surrounding tissue which can facilitate restoration of the elastic recoil of the lung. The device is designed to be used by an interventionalist or surgeon.

Figure 4A:
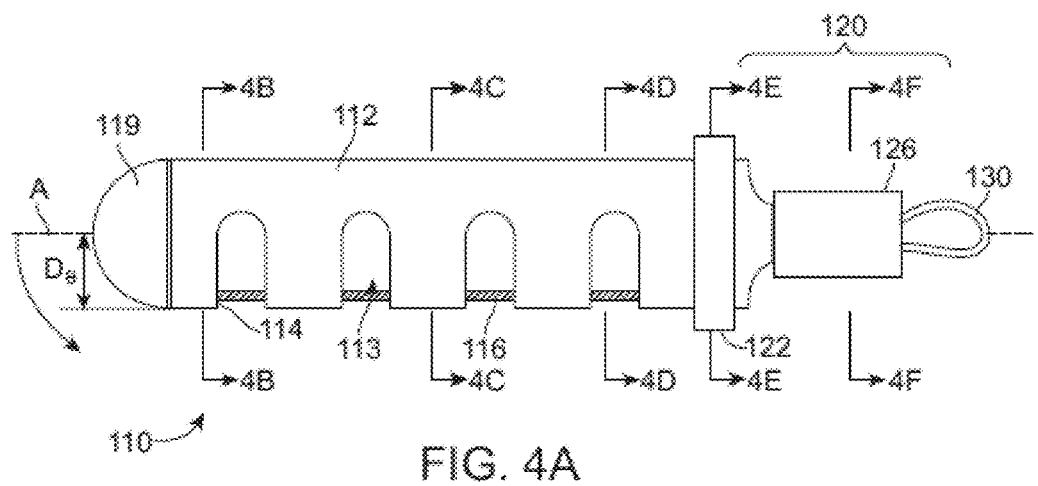
FIGS. 4A-4F illustrate a lung volume reduction device according to an aspect of the invention.
Figure 4B:
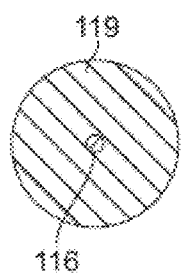
Figure 4C:
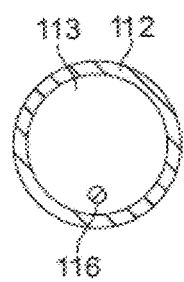
Figure 4D:
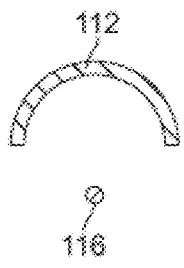
Figure 4E:
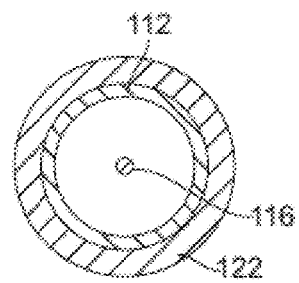
Figure 4F:
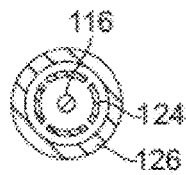

FIGS. 4A-F illustrate a shaft or tubular member of a lung volume reduction device 110 which may be included in an implant according to an aspect of the invention, with FIGS. 4B-F being cross-sections taken along the lines B-B, C-C, D-D, E-E, and F-F of FIG. 4A, respectively. The lung volume reduction device 110 includes a member, such as tubular member 112, which has c-cuts 114, or notches, along its length to provide flexibility such that the device can be deflected off a longitudinal axis A when deployed. In other words, the longitudinal axis of the implant shaft or body may be changed from a generally straight configuration suitable for distal insertion along axis A to a bent or deployed configuration. The bent or deployed implant may bend or reconfigure a surrounding airway so as to locally compress lung tissue. For example, where the cuts are oriented parallel to one another along the length of the tubular member and are of the same or similar depth D, the device will tend to uniformly curve around an axis point when deployed. As a result, the device preferentially curls or bends in a direction as determined by the shape of the slots. Different types (width, depth, orientation, etc.) of notches or slots can be used to achieve different operational effects and configurations of the deployed device without departing from the scope of the invention.

Positioned within a lumen 113 of the tubular member 112, is an actuation element 116 or pull-wire. The actuation element can have a circular circumference in cross-section, as depicted, or can have any other suitable cross-section. The actuation element 116 may be anchored at one end of the device 110, e.g. the distal end, by a cap 119. The cap 119 can be bonded to the device and a distal crimp can be provided to crimp the cap 119 into the pull-wire 116. The cap 119 may be rounded as depicted to make the dip of the device atraumatic. Alternatively, cap 119 may be configured to include an anchor configured to grasp the adjacent airway during the device deployment within the airway. The anchor may increase the amount of tissue compression by a deployed device and thereby increase the amount of beneficial tension in the lung. Such optional anchors are discussed further below. The opposing end, e.g. proximal end, may be adapted and configured to engage a mechanism 120. The mechanism 120 may be adapted deploy the device. Further mechanism 120 may be configured to lock the device into a deployed configuration once the device 110 is deployed or to unlock the device to facilitate retrieval of the device from an airway. The device 110 may be configured to be detachable from a delivery catheter adapted to deliver the lung volume reduction device. The delivery catheter and delivery of the device are discussed further below.

Mechanism 120, at the proximal end of the device may be adapted to include a retainer ring 122 that engages a ratchet 124 that can be used to lock the device in place. The coupler 126 retains the ratchet 124 such that the ratchet locks the device in place once deployed. At the proximal end, a retrieval adapter 130 is provided, such as a pull-wire eyelid. The retrieval adapter 130 may be adapted and configured to enable the device to be retrieved at a later point during the procedure or during a subsequent procedure. The ratchet device may include flanges that extend away from a central axis when deployed to lock the device in place.

FIGS. 5A-C illustrate yet another lung volume reduction device according to another aspect of the invention, with FIGS. 5B-C being cross-sections taken along the lines B-B, and C-C of FIG. 5A, respectively. As depicted in this embodiment, the lung volume reduction device 310 includes a member, such as tubular member 312, which has c-cuts 314, 314', or notches, along its length to provide flexibility such that the device can be deflected in more than one direction off a longitudinal axis A when deployed. In this embodiment, the notches are positioned on the member 312 on opposing sides of the member when the member is lying within a plane. For example, where the cuts are oriented parallel each other along the length of the tubular member and are of the same or similar depth D, the device will tend to uniformly curve around an axis point when deployed. In this embodiment, when deployed, the configuration of the notches would result in a deployed configuration that is "s-shaped" when the actuator element 316 is pulled proximally (i.e., toward the user).

Figure 6:
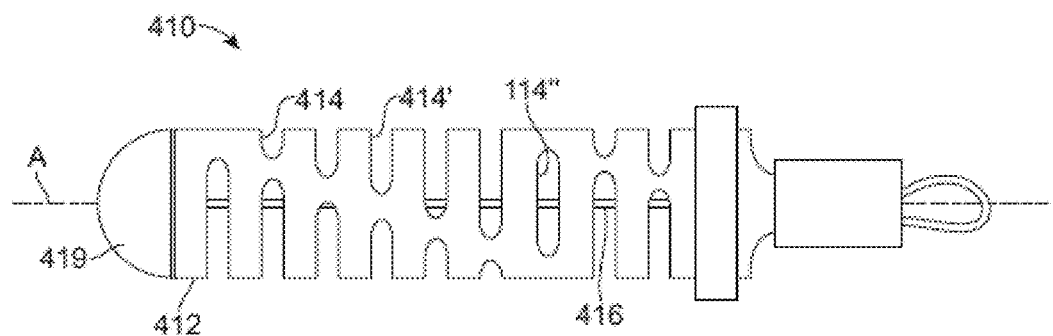
FIG. 6 illustrates a lung volume reduction device according to another aspect of the invention.

FIG. 6 illustrates yet another lung volume reduction device 410 according to another aspect of the invention. In this embodiment, the tubular member 412 has notches 414, 414', 414" configured in a spiral pattern along its length. As a result, when the actuation element 416 is pulled proximally toward the user, the device bends to form a spiral as illustrated below.

Figure 7:
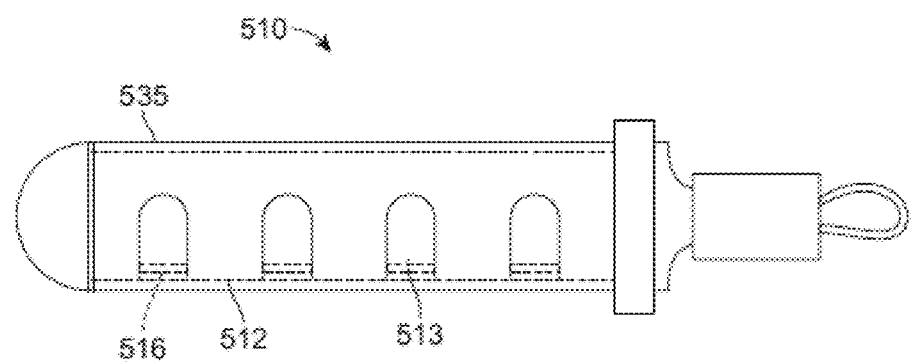
FIG. 7 illustrates a lung volume reduction device encased in a sheath.

FIG. 7 illustrates a lung volume reduction device 510 encased in a sheath 535. The sheath can be a polymeric elastic membrane, such as silicone. The sheath can prevent material from a body cavity from entering the lumen 513 of the tubular member 512. An actuation member 516 is provided within the lumen 513 of the tubular member 512.

FIGS. 8A-D illustrate yet another lung volume reduction device 610 according to another aspect of the invention, with FIGS. 8B-D being cross-sections taken along the lines B-B, C-C, and D-D of FIG. 8A, respectively. The lung volume reduction device 610 in this embodiment is comprised of individual segments 612, 612', 612". The segments can be configured, for example, to have identical asymmetrical configurations such that a compressible space 614 is between each segment before the device is actuated by activating the actuator element 616. Each of the segments can further comprise a detent on a first surface which opposes a mating indentation on a surface of an opposing segment. As will be appreciated, a variety of components of devices disclosed herein can be configured to provide locking or mating mechanisms to facilitate actuation and operation. When the actuation element 616 is activated, the compressible space is reduced and the opposing surfaces of two adjacent segments come together to reduce or eliminate the space between them, depending upon the desired outcome. Where the segments have identical or nearly identical configurations, the device will evenly arc around an axis point. Where the segments do not have identical configurations, a variety of configurations can be achieved upon deployment depending on the configurations of the segments selected and the organization of the segments in the device. As with previous embodiments, the actuator element 616 is secured at one end, e.g., the distal end, by a cap 619. The segments can be formed as hypotubes or can be formed as injection molded or solid pieces. Use of segments can avoid fatigue on the device because the surfaces come in contact with one another during compression. Material selection can also prevent biometallic corrosion. Further, the segment design is conducive for mass production and maintenance of consistence for final shape and operation.

FIGS. 9A-B illustrate segments 712, 712' suitable for use in configuring a lung volume reduction device according to an aspect of the invention. The segments, as depicted, can be generally cylindrical with a pair of surfaces that are either parallel or non-parallel each other at either end. To achieve the operation described above, a first surface 713 could be perpendicular to the elongated tubular sides 715 of the element, while the opposing surface 717 is not perpendicular to the sides of the element (or parallel to the opposing first surface). A detent 721 can be provided on one surface that is configured to mate with an indentation 723 the second surface of another. Other configurations, such as a key: keyway combination, can be used without departing from the scope of the invention. A central lumen 725 is provided through which an actuator element (described above) passes through.

FIG. 10 illustrates devices 2510 according to the invention in a pre-deployed configuration. FIG. 10 illustrates the device 2510 having a longitudinal configuration, such as the configuration assumed prior to deployment. When the device is implanted and placed in compression or tension axially, the device will preferentially bend. The actual preferential bending will vary depending upon the configuration of the device. For example, the location, depth, and orientation of the slots depicted in FIGS. 4-7; or the orientation of the walls of the segments of FIG. 8. As will be appreciated by those skilled in the art upon reviewing this disclosure, other configurations can be achieved by, for example, altering the size and location of the c-cuts on the tubular member, or by altering the configuration of the segments illustrated in FIGS. 8-9. Once the device preferentially bends, the device imparts a bending force on the lung tissue which results in a reduction of lung volume. As is appreciated, the implant, once re-shaped, is shorter in length than the deliverable implant configuration. The shortening occurs when for example, the distance between the proximal end and the distal end is reduced. Typically, the deliverable shape of the device is such that it fits within a cylindrical space that is 18 mm in diameter or smaller. Thus, the implant can come into contact with tissue that is larger than $10^{-6}$ square inches per linear inch of the implant length. The re-shaped or deployed implant can be configured in a variety of shapes to lie within a single plane, or to adopt any other suitable configuration, such that it does not lie within a single plane. Additionally, the device can have varying rates of curvature along its length.

Figure 11A:
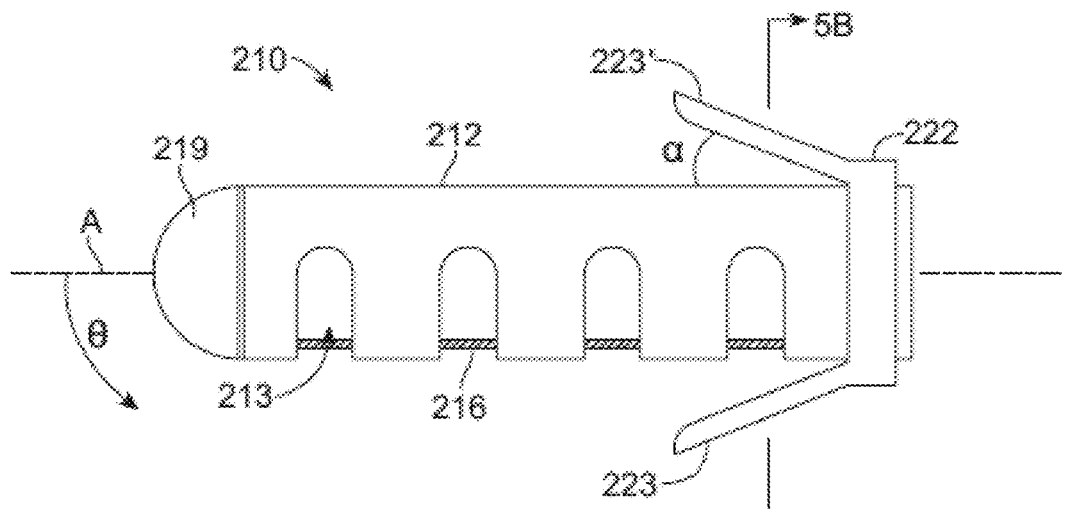
FIGS. 11A-11B illustrate a lung volume reduction device according to another aspect of the invention.
Figure 11B:

Turning to FIGS. 11A-B, a lung volume reduction device 210 according to another aspect of the invention is depicted, with FIG. 11B being a cross section taken along the lines B-B of FIG. 11A. Positioned within a lumen 213 of the tubular member 212 is an actuation element 216 or a pull wire. As described above, the actuation element can have a circular circumference in cross-section, as depicted, or can have any other suitable cross-section. The actuation element 216 may be anchored at one end of the device 210, e.g. the distal end, by a cap 219. In this embodiment, the retainer ring 222 is configured to provide anchors 223, 223' or teeth that are adapted to deploy by retracting the retaining sheath of a delivery catheter. When deployed, the anchors 223 contact the airway and affix the device in place. The anchor 223 can be configured to be self-expanding such that the anchors approach or extend through (e.g., hook) the airway. The amount of expansion of the anchors will be controlled by the design and the materials used. For example, where a shape memory material is used, the anchors can be configured to extend away from the longitudinal wall of the tubular member by a predetermined angle α, as depicted ~10 degrees. The design of the anchor can further be driven by the length of the device. The anchors can be configured to catch on the airway when deployed in a manner similar to the way a stent catches within the vasculature, or the anchor can be designed to cause friction. Prior to deployment, the anchors may be retained by a retaining sheath (illustrated below).

Figure 12A:
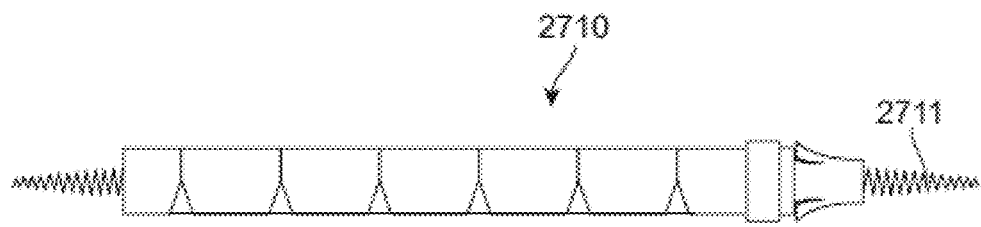
FIGS. 12A-12C illustrate a variety of device configurations with atraumatic tips.
Figure 12B:
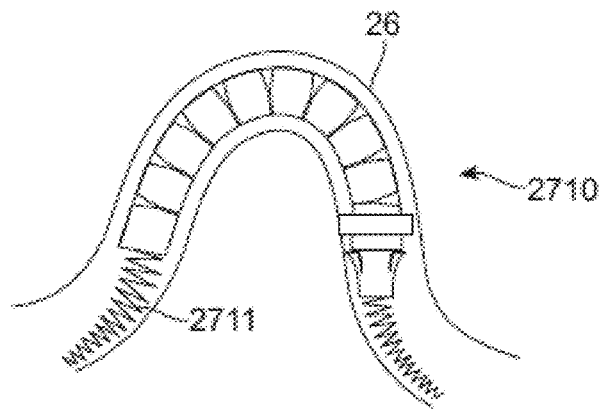
Figure 12C:
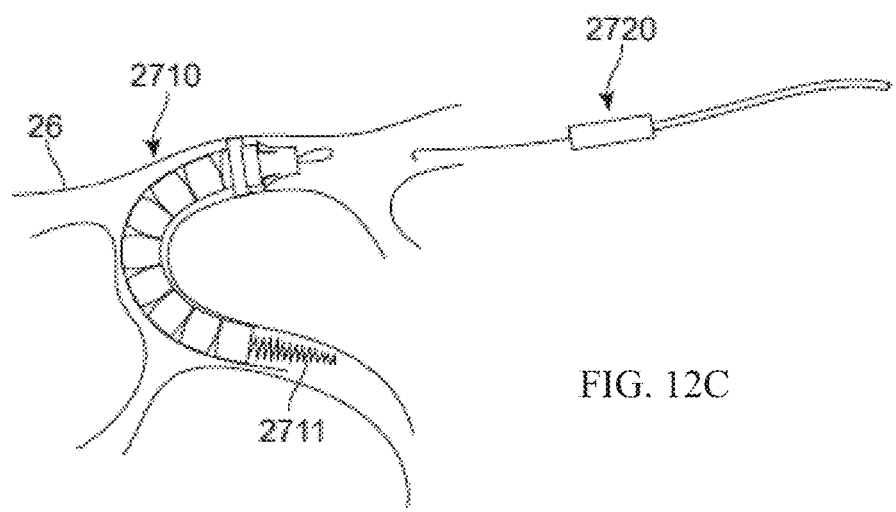

FIGS. 12A-C illustrates devices 2710 according to the invention implanted within, for example, a bronchiole 26. The device 2710 depicted in FIG. 12A is configured to provide an atraumatic tip 2711 on either end of the device. When the device 2710 is activated within the bronchiole 26 the device curves and imparts a bending force on the lung tissue. As a result of the bending pressure, the tissue curves and compresses upon its self to reduce lung volume. Additionally, deployment of the device can result in the airway becoming bent. As illustrated in FIG. 33C the device can also be configured with a single atraumatic tip so that the deployment mechanism 2720 can easily interface with the proximal end of the device. Alternatively, atraumatic tip 2711 may be comprise a rounded tip similar to the tip illustrated in FIG. 4A.

In another embodiment of the invention, as illustrated in FIGS. 13A-F, the device 810 is comprised of a plurality of individual wires formed of shape memory material that resume their shape when implanted. The wires can be heat treated to assume a specific shape, such as a C shape as described above. The wires are then individually implanted through a delivery system 850 such that when the first wire is implanted the diameter of the wire may be small enough that the wire cannot overcome the force applied by the surrounding tissue to assume its pre-configured shape. However, upon implantation of additional wires, the amount of strength available cumulatively among the wires does overcome the force applied by the tissue and the wires, together, achieve the desired shape (see. FIG. 13F). As will be apparent to those of skill in the art, the strength of a shaped wire can vary depending on how much material is used. For example, a shaped wire with a larger cross-section will have higher strength than a shaped wire with a smaller cross-section. However, a larger diameter wire may be harder to implant because it would be harder to straighten into a shape suitable for deployment. Where many small wires are used, each wire individually is more flexible and can be deployed easier, but as a larger number of wires are implanted the combined strength increases. In some embodiments, it may be useful to configure the devices 810 such that the use of, for example, 50-100 wires will have the strength to overcome pressure applied by the tissue. The wires 810 can be deployed within a flexible polymer tube to keep the wires in proximity to each other.

Figure 14:
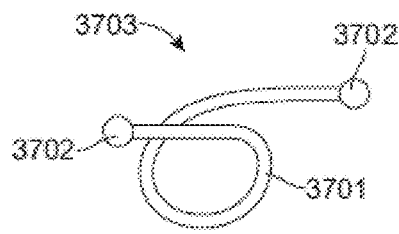
FIG. 14 illustrates a device configuration.

FIG. 14 shows an example of an implantable device 3703 made from Nitinol metal wire 3701. Nickel-Titanium, Titanium, stainless steel or other biocompatible metals with memory shape properties or materials with capabilities to recover after being strained 1% or more may be used to make such an implant. Additionally, plastics, carbon based composites or a combination of these materials would be suitable. The device is shaped like a French horn and can generally lie in a single plane. The ends are formed into a shape that maximizes surface area shown in the form of balls 3702 to minimize scraping or gouging lung tissue. The balls may be made by melting back a portion of the wire, however, they may be additional components that are welded, pressed or glued onto the ends of wire 3701.

A Nitinol metallic implant, such as the one illustrated in FIG. 14, may be configured to be elastic to recover to a desired shape in the body as any other type of spring would or it can be made in a configuration that may be thermally actuated to recover to a desired shape. Nitinol can be cooled to a martensite phase or warmed to an austenite phase. In the austenite phase, the metal recovers to its programmed shape. The temperature at which the metal has fully converted to an austenite phase is known as the Af temperature (austenite final). If the metal is tuned so that the Af temperature is at body temperature or lower than body temperature, the material is considered to be elastic in the body and it will perform as a simple spring. The device can be cooled to induce a martensite phase in the metal that will make the device flexible and very easy to deliver. As the device is allowed to heat, typically due to body heat, the device will naturally recover its shape because the metal is making a transition back to an austenite phase. If the device is strained to fit through a delivery system, it may be strained enough to induce a martensite phase also. This transformation can take place with as little as 0.1% strain. A device that is strain induced into a martensite phase will still recover to its original shape and convert back to austenite after the constraints are removed. If the device is configured with an Ar temperature that is above body temperature, the device may be heated to convert it to austenite and thermally activate its shape recovery inside the body. All of these configurations will work well to actuate the device in the patient's lung tissue. The human body temperature is considered to be 37 degrees C. in the typical human body.

Figure 15:
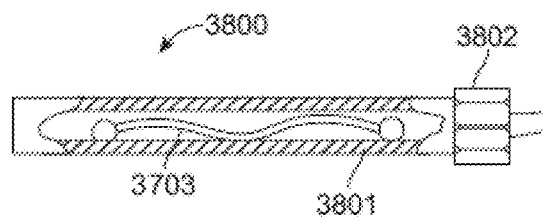
FIG. 15 illustrates a device in a loading cartridge.

FIG. 15 illustrates a cutaway view of a delivery cartridge system 3800 that constrains the implant device 3703 in a deliverable shape. The device 3801 may be shipped to the intended user in such a system or it may be used as a tool to more easily load the implant into a desired shape before being installed into the patient, bronchoscope or a catheter delivery device. The cartridge may be sealed or terminated with open ends or one or more hubs such as the Luer lock hub 3802 that is shown. The implant should be constrained to a diameter that is the same or less than 18 mm diameter because anything larger than that will be difficult to advance past the vocal cord opening.

Figure 16:
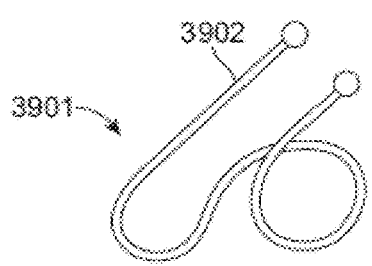
FIG. 16 illustrates a long device configuration.

FIG. 16 illustrates another implant device 3901 that is shaped in a three dimensional shape similar to the seam of a baseball. The wire is shaped so that proximal end 3902 extends somewhat straight and slightly longer than the other end. This proximal end will be the end closest to the user and the straight section will make recapture easier. If it were bent, it may be driven into the tissue making it hard to access.

Figure 17:
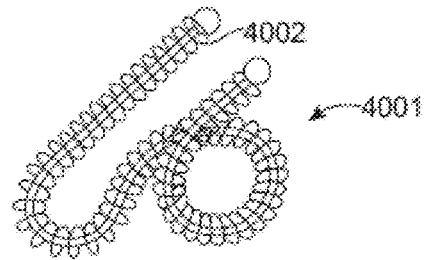
FIG. 17 illustrates a device configuration with a wire support frame.

FIG. 17 is an illustration of another implant system 4001. It is similar to that shown in FIG. 16 with the addition of a wire frame 4002 surrounding the device. The wire frame may be used, for example, to increase the bearing area that is applied to the lung tissue. By increasing the bearing area, the pressure born by the tissue is reduced along with a reduction in the propensity for the device to grow through lung structures or cause inflammatory issues. Small wires that apply loads in the body tend to migrate so we believe that the device should be configured to possess more than 0.000001 ($1^{-6}$ in$^2$) square inches of surface area per linear inch of the length of the device. The frame is one of many ways to provide a larger surface area to bear on the tissue.

Figure 18:
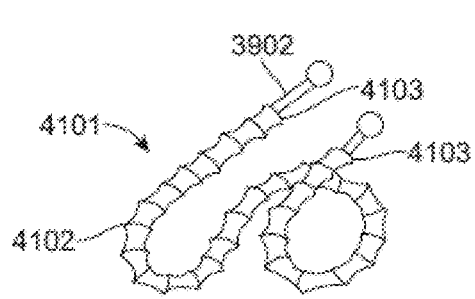
FIG. 18 illustrates a device configuration with a covering.

FIG. 18 shows yet another example of a device 4101 according to the invention. The device 4101 features a covering to increase bearing area 4102. In this example, the main wire 3902 is covered by a wire frame and a polymeric covering 4102. The covering may be made of any biocompatible plastic, thermoplastic, fluoropolymer, Teflon®, urethane, metal mesh, coating, silicone or other resilient material that will reduce the bearing pressure on the lung tissue. The ends of the covering 4103 may remain sealed or open as shown to allow the user to flush antibiotics into and out of the covering.

Figure 19:
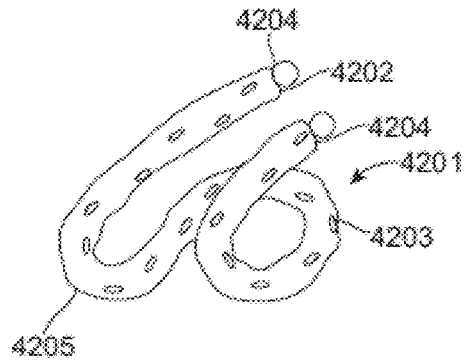
FIG. 19 illustrates a device configuration with a perforated covering.

FIG. 19 illustrates another configuration of the implant device 4201 showing a covering 4205 with perforations 4203 adapted and configured to allow the device to be flushed. The ends 4202 of the covering are sealed to the ends of the device to keep the two components fixed and prevent sliding of one or the other during deployment. The covering may be thermally bonded, glued or shrunk to a tight fit.

Figure 20:
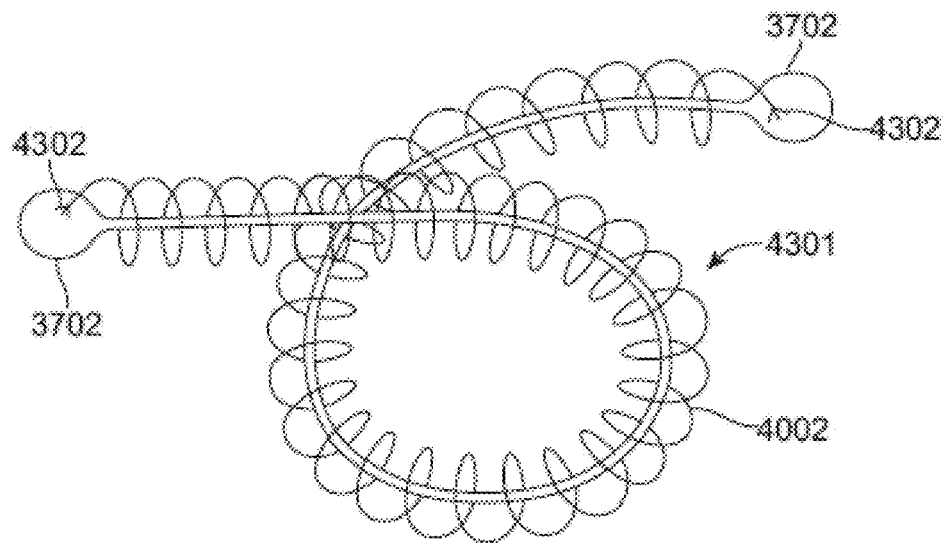
FIG. 20 illustrates a device configuration with an attached wire support frame.

FIG. 20 illustrates a device 4301 that has the wire frame 4002 joined to the ball ends 3702 at a junction 4302. The balls may be melted from the wire stock and the wire frame may be incorporated into the ball at that time. It may also be glued, pressed together, welded or mechanically locked together.

Figure 21:
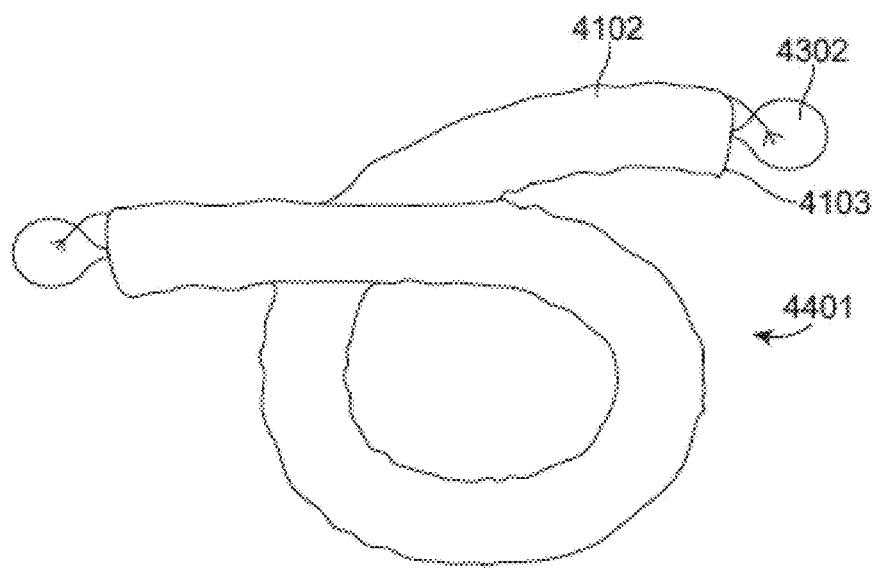
FIG. 21 illustrates a device configuration with an attached frame and covering.

FIG. 21 illustrates another implant device 4401 with an attached wire frame 4302, main wire 4103 and a covering 4102. The complete implant may include additional structures or materials which enhance the ability of the implant to provide therapeutic benefits during long-term implantation, with many of these additional structures or materials providing a bearing surface or interface between the compression-inducing shaft of the device and the surrounding tissue lumen wall of an airway. These additional structures or materials may be any of the structures or materials which are disclosed in related U.S. patent application Ser. No. 12/782,515 filed on May 18, 2010, entitled Cross-Sectional Modification During Deployment of an Elongate Lung Volume Reduction Device, the application of which is incorporated herein by reference.

Figure 22:
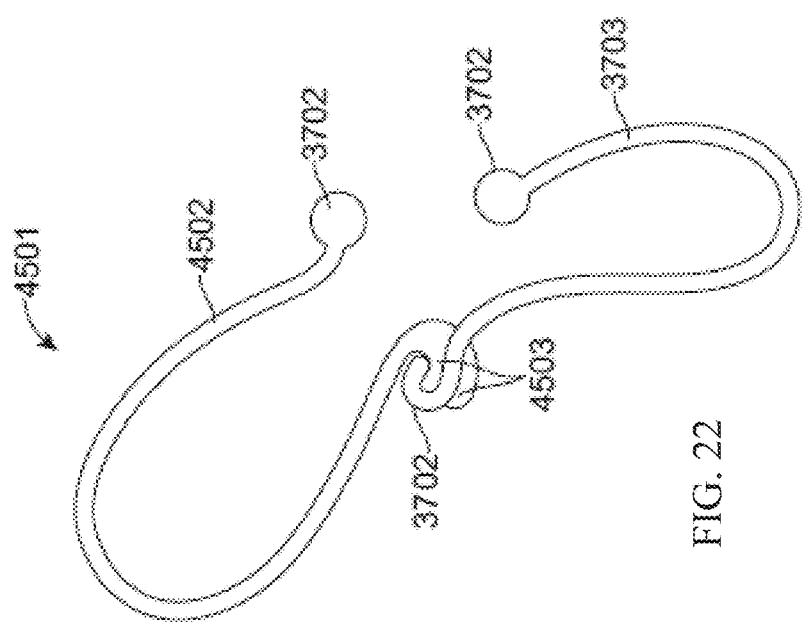
FIG. 22 illustrates a device configuration that is coupled to a second device.

FIG. 22 illustrates a system of one or more devices that can be hooked together 4501. The device 3703 is configured such that it terminates on both ends, for example, with blunt ball shaped ends 3702. The device 4502 is terminated on one end with an open cup and slot shape 4503 that allows the devices to be coupled together. These devices may be delivered together or coupled in-situ. Devices may be installed into a single duct in the lung or in different locations that may be linked together.

Figure 23:
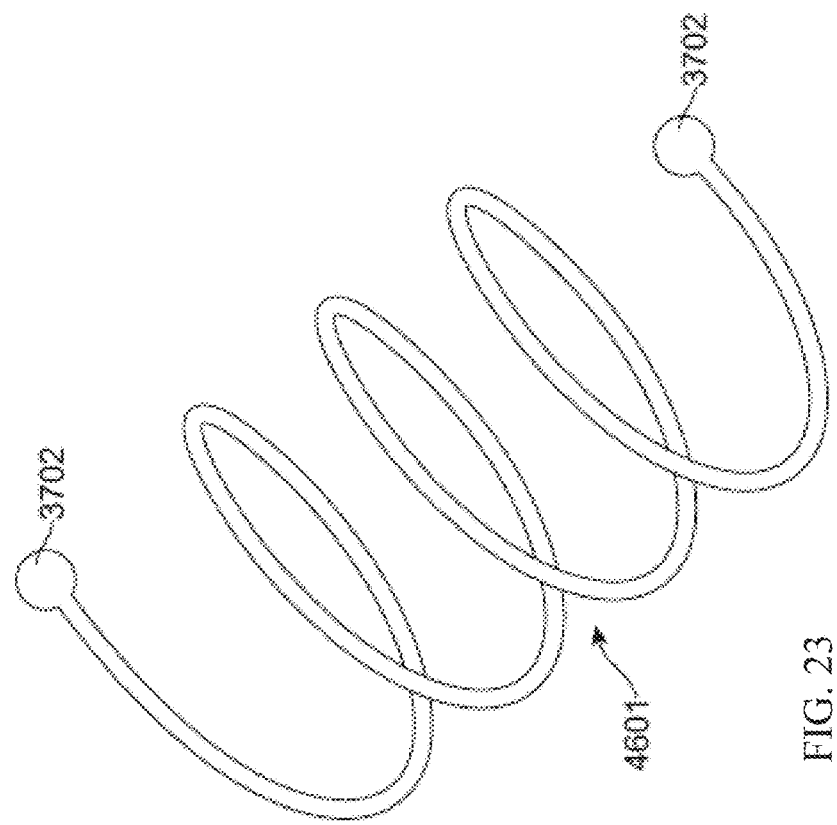
FIG. 23 illustrates a device configuration in a coil shape.

FIG. 23 illustrates another three dimensional device 4601 made in the form of a coil with atraumatic ball terminations 3702.

FIGS. 24A-24E illustrate another 100 mm long device 900 in a pre-implantation or a post-implantation configuration. In this configuration, device 900 includes two helical sections 902, 904 with a transition/intermediate section 906 disposed between the two helical sections 902, 904. Similar to the devices described above, device 900 may have another configuration which corresponds to a delivery configuration in which the device assumes during delivery to a treatment region within an airway. Each helical section 902, 904 includes a respective helical axis 906, 908. In the embodiment shown in FIGS. 24A-24E, helical axis 906 is at an angle with helical axis 908. The angle between the helical axis 906 and helical axis 908 may be between 190° and 230° in some embodiments. In alternative embodiments, helical section 902, 904 may share a helical axis.

In this particular embodiment, device 900 comprises a shape-memory material, however a person of ordinary skill would recognize that many of the methods described above may be used to configure a device such that it may be mechanically actuated and locked into a similar configuration. Device 900 as shown in the figures includes a right-handed helical section and a left-handed helical section and the transition section 910 between the two helical sections comprises a switchback transition section when the device is in the pre-implantation or post-implantation configuration. The switchback transition section may be defined as the intermediate section where the elongate body of the implant transitions between oppositely handed helical configurations. In some embodiments, the switchback transition section may reduce the recoil forces during device 900 deployment thereby providing greater control of device 900 during deployment. Additionally, the switchback transition may reduce migration of the implant after deployment and thus maintain the device's tissue compression advantages. As shown in FIGS. 24A-24E, the helical sections do not have to include the same number of loops or complete helix turns. In this embodiment the distal helix 904 comprises more loops than the proximal helix 902. Alternatively, device 900 may be configured such that the proximal helix 902 includes more loops than distal helix 906. The helical sections may be configured to include a pitch gap of 0.078±0.025 in. In this particular embodiment, the two helical sections are circular helical sections. Other embodiments of the present invention may be configured to include spherical or conical helical sections when in a pre-implantation or post-implantation configuration.

FIGS. 25A-25D illustrate device 900 further comprising a jacket 916. Jacket 916 may increase the diameter of device 900 so as to provide more area per unit force when deployed in the airway. For example, the jacket may increase the device diameter by 3.25× to provide more area per unit force. Accordingly, the increase in diameter may reduce erosion into an airway wall once device 900 is deployed. Jacket 916 may comprise 55D polycarbonate urethane (PCU). PCU may reduce biofilms that promote bacterial growth thereby limiting incidents of infection. The jacket may cover the proximal helix, the distal helix, and the transition section disposed between the helices. Additionally, the jacket may cover the distal portion of the device as shown in FIGS. 25A-25D. In some embodiments, the proximal end is also covered by the jacket. Alternatively, the jacket may cover only certain portions of the device. The jacket may be fastened to device 900 by an adhesive such as Loctite 3311.

The proximal end 912 and distal end 914 of device 900 may be configured to be atraumatic. In the depicted embodiment, proximal end 912 and distal end 914 comprises a ball with a diameter of about 0.055±0.005 in which may be made by melting back a portion of the wire or may be additional components that are welded, pressed or glued onto the ends of the wire. The atraumatic ball may have a smaller surface area to allow a low catheter friendly profile or a larger ball which reduces the tissue stress with the larger surface area. In other embodiments, a tissue penetrating anchor may be used to couple the proximal end or distal end of device 900 to an airway wall during the deployment of the device.

Figure 24A:
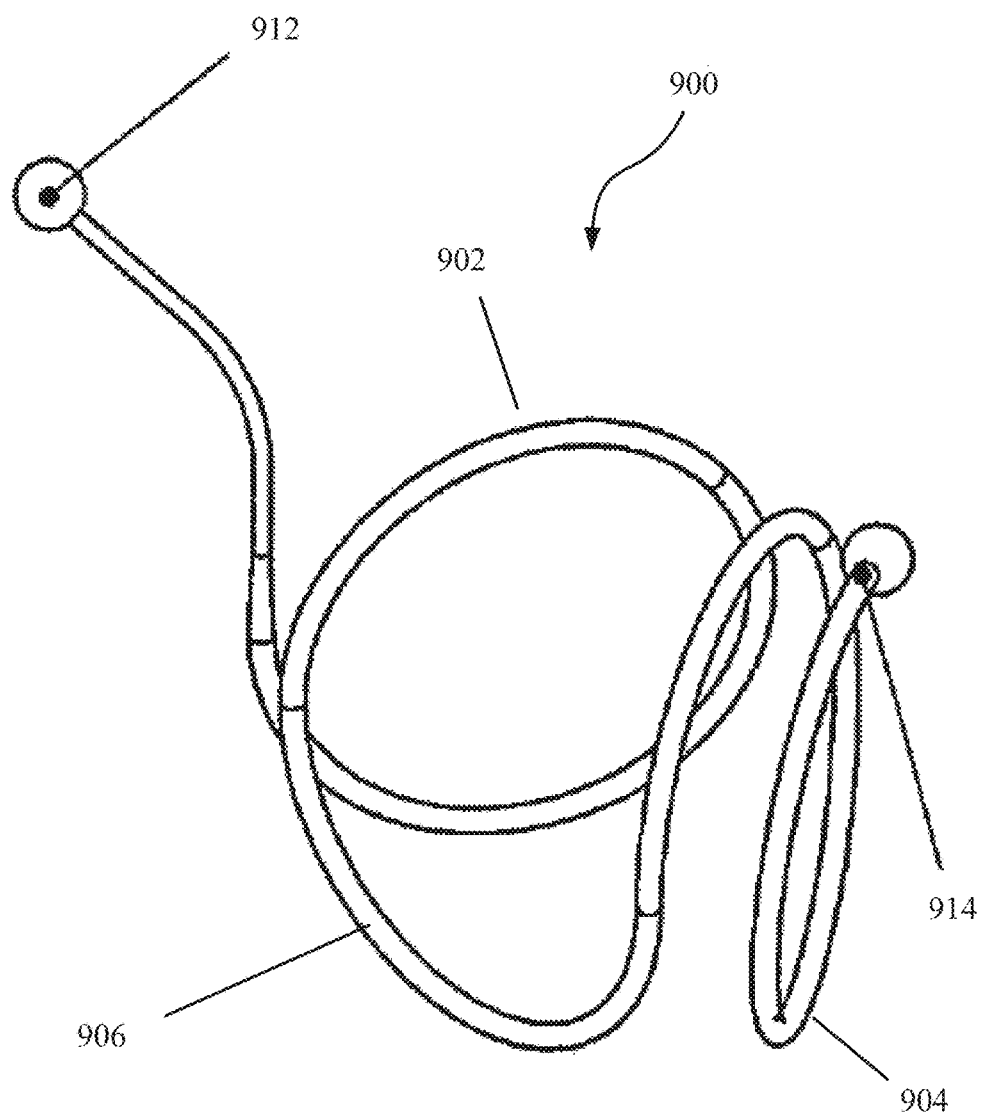
FIGS. 24A-24E illustrate a device with two helical sections and a transition section.
Figure 24B:
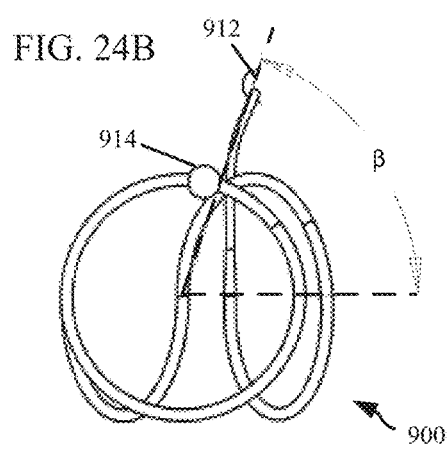
Figure 24C:
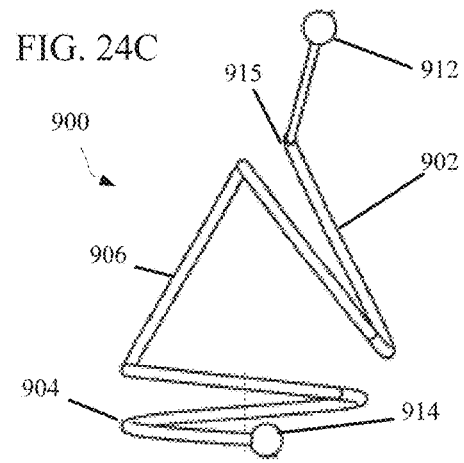
Figure 24D:
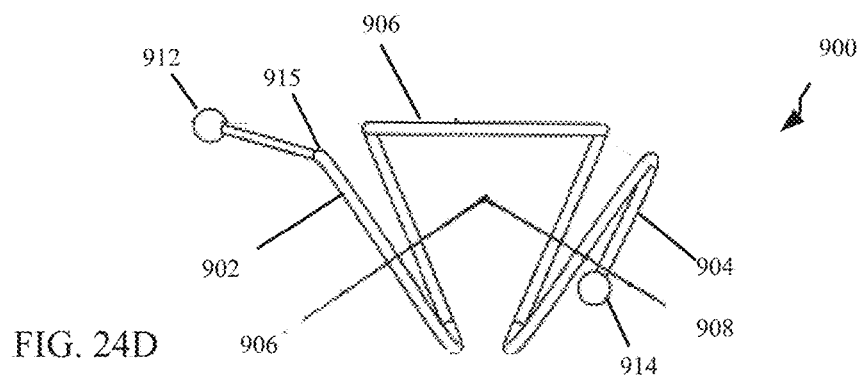
Figure 24E:
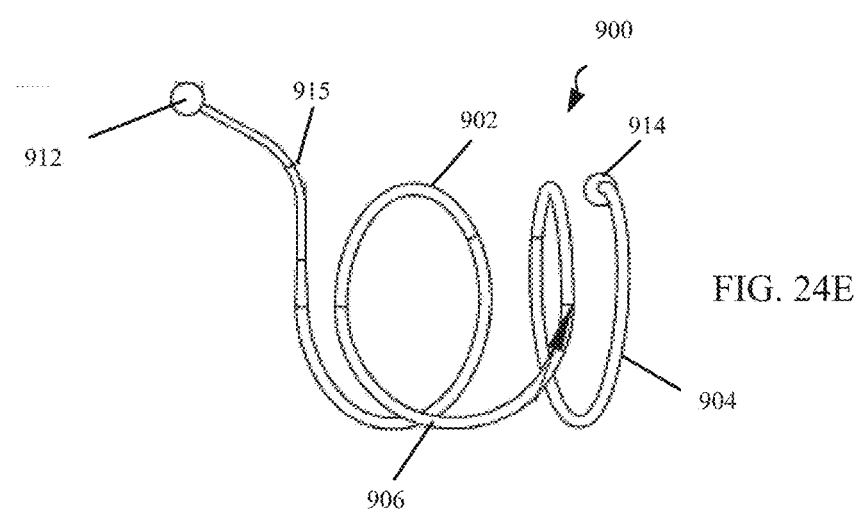
Figure 26A:
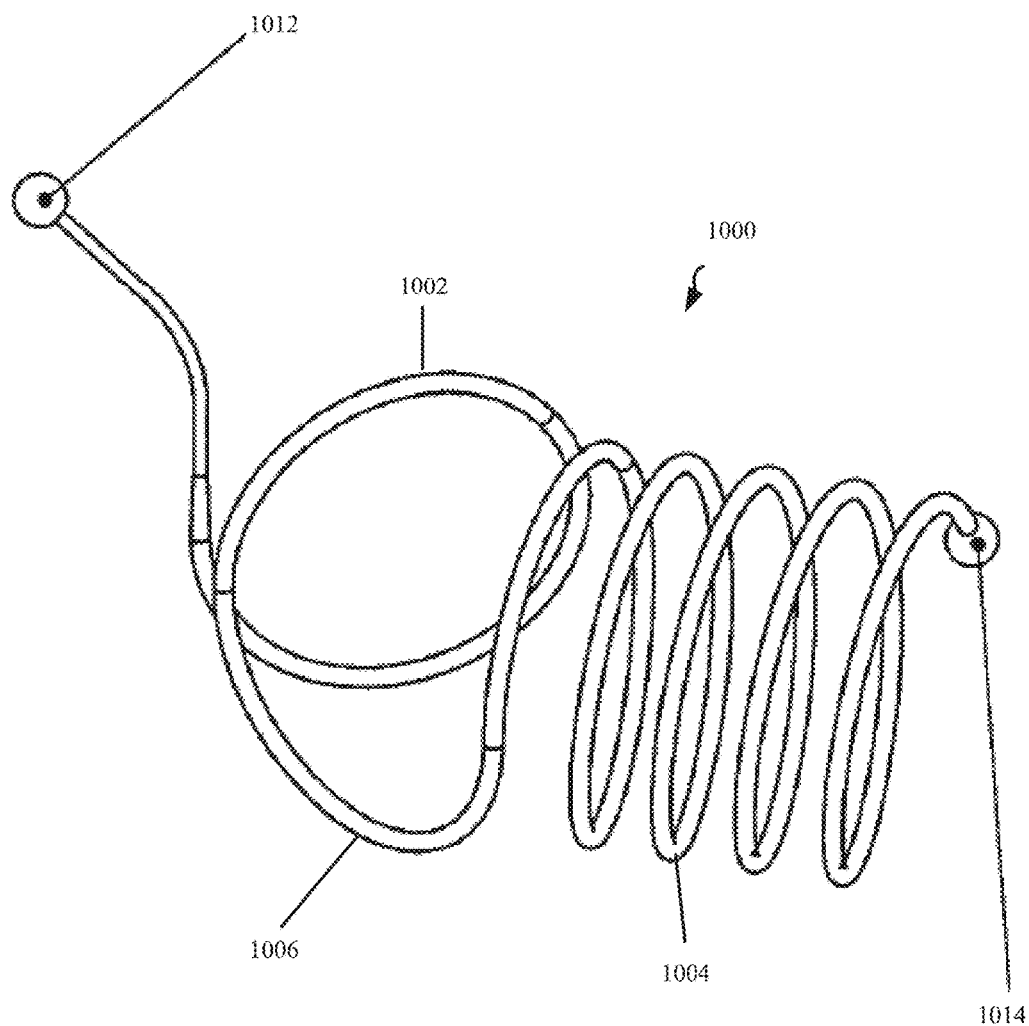
FIGS. 26A-26E illustrate another embodiment of the device with two helical sections and a transition section.
Figure 26B:
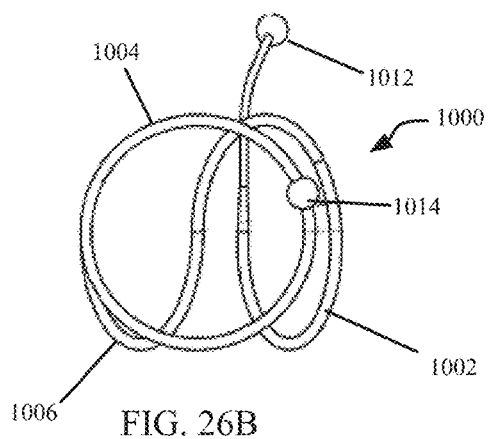
Figure 26C:
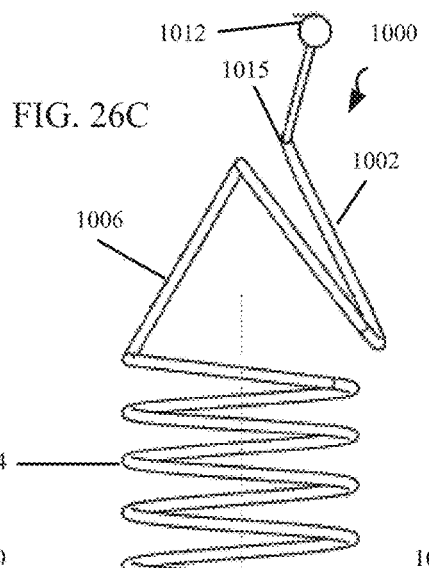
Figure 26D:
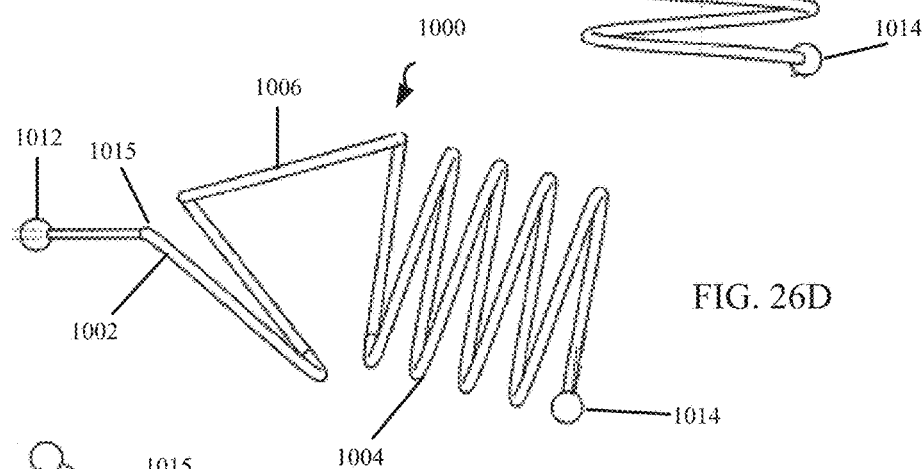
Figure 26E:
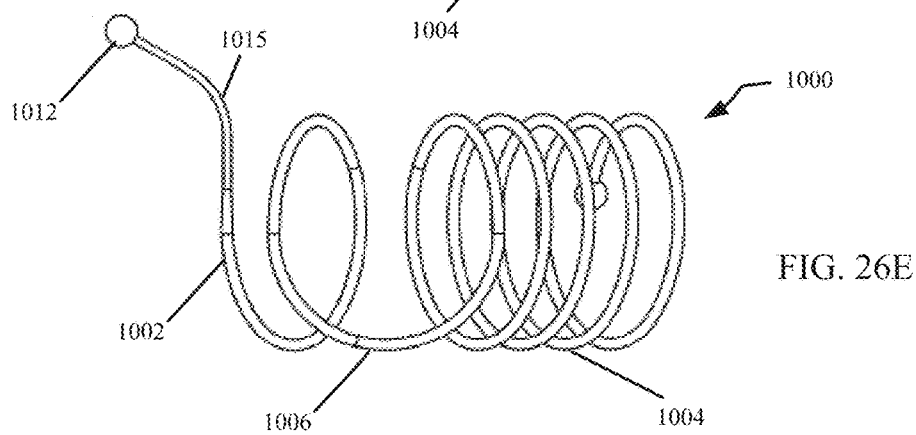

Proximal end 912 is also configured as a stand-off proximal tail which may extend past an outer boundary defined by the proximal coil. For example, as shown in FIG. 24B, angle β may be 76°±20°. In some embodiments the stand-off proximal tail may extend away from the axis of a helical section when the device is in the pre-implantation or post-implantation configuration as shown in FIG. 24D. The stand-off proximal tail may include a steeper bend 915 at the proximal end which may allow more length to be used in compression. Additionally, the standoff proximal tail provides for better device retrievability once deployed by reducing the chances that the proximal tail will impinge against or penetrate through the airway wall once the device is deployed. Accordingly, device repositioning and/or removal may be facilitated by a device with a standoff proximal tail configuration. The stand-off proximal tail may be used with other device configurations. In one embodiment, the stand-off proximal tail may be utilized with a device configuration comprising a single helical section.

FIGS. 26A-26E illustrate device 1000 which is similar to device 900. Device 1000 includes a proximal helical section 1002 and a distal helical section 1004. A transition 1006 is disposed between the two helical sections 1002, 1004. The proximal end 1012 and distal end 1014 comprise atraumatic balls. Distal helical section 1004 includes 4.25 loops but may comprise more. FIGS. 27A-27D illustrate device 1000 further comprising jacket 1016. The distal helical sections may further compress portions of the lungs when device 1000 is deployed within an airway. Similar to device 900, other configurations of device 1000 are possible. For example, device 1000 may be configured to include two right handed helical sections or two left handed helical sections. Optionally, the helical sections may share the same helical axis.

Figure 28:
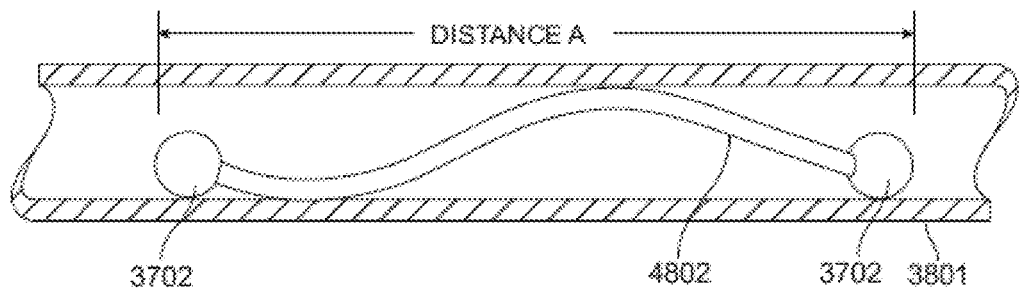
FIG. 28 illustrates a device in a delivery configuration during delivery within an airway.
Figure 29:
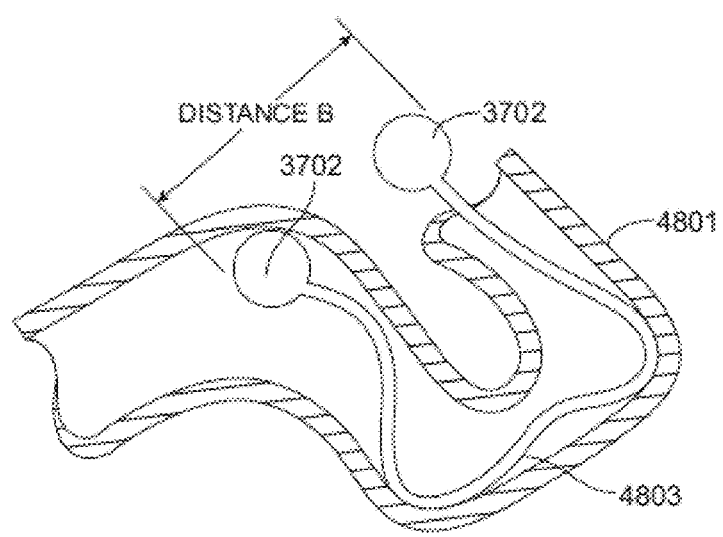
FIG. 29 illustrates the device of FIG. 28 deployed to the deployed configuration within the airway.
Figure 30:
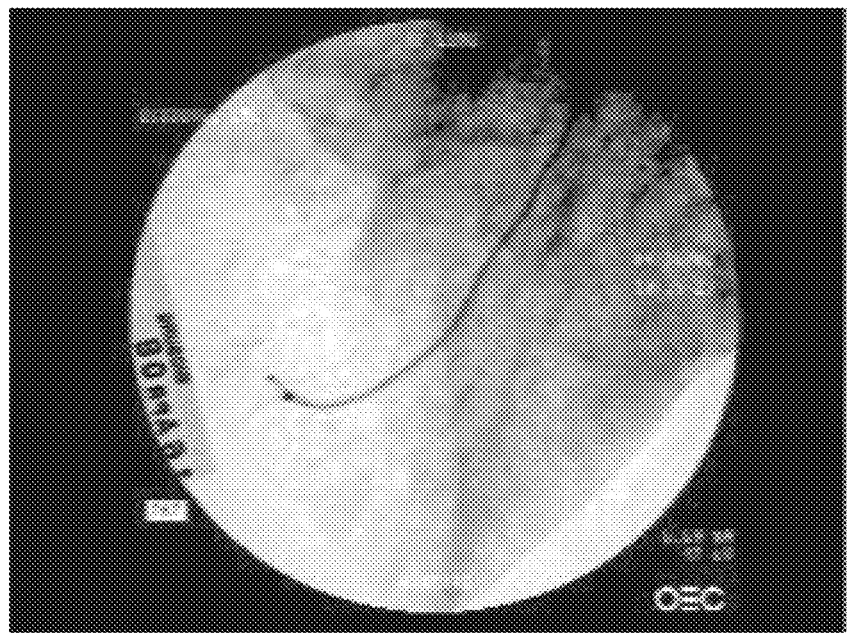
FIGS. 30 and 31 are images of human lung tissue before and after a portion of the lung tissue is compressed from within an airway by an embodiment of an implant.

FIGS. 28 and 29 illustrate how the device length is reduced when the device is deployed in-situ. The device shown in the delivery configuration 4802 in FIG. 28 is also shown in the deployed configuration 4803 in FIG. 29. The distance A between the device ends 3702 is large while the device is constrained by the constraining cartridge device 3801. Distance A is similar when the device is constrained by a loading cartridge, catheter or bronchoscope. FIG. 29 shows the same device in a deployed configuration 4803 in an airway 4801 that has been deformed by the shape recovery of the implant device. FIG. 29 shows that the distance B between the device ends 3702 is substantially shorter after the device is deployed. Similarly, FIG. 30 illustrates the device of FIGS. 26A-E deployed within an airway. As can be seen, the airway lining may be pinched between adjacent helix loops thereby providing beneficial tissue compression. In some embodiments, a 70% improvement in volume reduction over current LVRC can be obtained.

Figure 31:
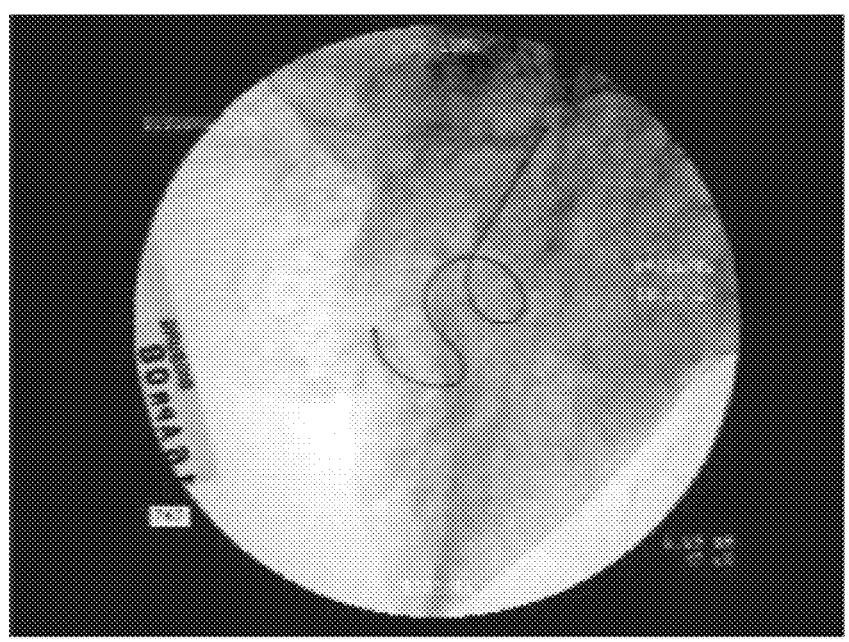

FIGS. 30 and 31 show two photos of a human lung in a chest cavity simulator. The lungs were explanted from a person who expired due to chronic obstructive pulmonary disease (COPD). The cavity is sealed with the lung's main stem bronchi protruding through a hole in the cavity wall. The bronchi has been sealed to the hole so a vacuum can be applied to aspirate the air from the space between the cavity interior and the lung. This allows the lung to be drawn to a larger expanded condition with vacuum levels that are physiologic (such as 0.1 to 0.3 psi, similar to that of the typical human chest cavity). FIG. 30 illustrates a 175 mm long implant that has been delivered to a distal end of a delivery catheter as described above. The catheter is substantially constraining the implant in a straightened delivery configuration.

FIG. 31 shows the implant after the catheter has been retracted from the implant to allow the implant to return toward its relaxed configuration. The implant has recovered to its original shape by means of elastic recoil and possibly a Nitinol metal compositional phase change substantially back to austenite. The delivery grasper has been unlocked to release the implant in the airway. By comparing the lung tissue in FIGS. 30 and 31, the regions of the lung that are compressed by the implant during the process of shape recovery (changing from a delivered shape to a deployed shape) can be identified. The compressed regions are visualized in the fluoroscopic images by distinct increases in darkness or darker grey shades of the images. Darker regions identify more dense regions and lighter identify less dense regions. The implant can be seen to compress regions as it recovers to cause areas of the lung to become darker. Other regions can be seen to be strained or stretched and this can also be seen as regions that are converted to a lighter region.

The implant can be placed in pathologic regions in the lung that provide limited or no exchange of gas to and from the blood stream because the alveolar walls used to do so have been degraded and destroyed by disease. These are typically the most degraded regions that have lost mechanical strength and elasticity. In an inhaling COPD patient these degraded areas fill with air first, at the expense of gas filling in regions that could better help the patient, because the weakened tissue presents little to no resistance to gas filling. By implanting the devices in these areas, resistance is provided so the gas is filled in regions that still can effectively exchange elements to and from the blood stream. Viable regions have structure remaining so resistance to gas filling is present as this is a normal physiologic property. The implant advantageously provides more gas filling resistance in the destroyed regions than the normal physiologic resistance in the viable regions so gas flows to viable tissue. This eliminates or reduces the counterproductive "preferential filling" phenomenon of the most diseased lung tissue prior to treatment. The implantable device may also delay collapse of airways during a breathing cycle thereby limiting the amount of air trapping in a lung. Accordingly, patients with small airway disease or with alpha 1-antitrypsin deficiency may also be treated with such a device. Additionally, the implantable device may be configured to provide enhanced breathing efficacy immediately after implantation while still allowing gas exchange distal to the deployed implant thereby reducing the chance of atelectasis of lung tissue distal to the implant.

As with previous embodiments, the embodiments depicted in FIGS. 14-31 are adapted and configured to be delivered to a lung airway of a patient in a delivery configuration and to change to a deployed configuration to bend the lung airway. The devices are characterized in that the devices have a delivery configuration that is resiliently bendable into a plurality of shapes, such as the ones depicted in the Figures. The design of the devices can be such that strain relief is facilitated on both ends of the device. Further the ends of the device in either the delivery or deployed state are more resilient.

The devices can have any suitable length for treating target tissue. However, the length typically range from, for example, 2 cm to 20 cm, usually 5 cm. The diameter of the device can range from 1.00 mm to 3.0 mm, preferably 2.4 mm. The device is used with a catheter which has a working length of 60 cm to 200 cm, preferably 90 cm.

In operation the devices shown in FIGS. 14-31 are adapted and configured to be minimally invasive which facilitates easy use with a bronchoscope procedure. Typically, there is no incision and no violation of the pleural space of the lung during deployment. Furthermore, collateral ventilation in the lung does not affect the effectiveness of the implanted device. As a result, the devices are suitable for use with both homogeneous and heterogeneous emphysema.

Each of the devices depicted in FIGS. 14-31 are adapted and configured to impart bending force on lung tissue. For example, a spring element can be provided, as illustrated in FIG. 14 that imparts bending force on lung tissue. The implantable spring element that can be constrained into a shape that can be delivered to a lung airway and unconstrained to allow the element to impart bending force on the airway to cause the airway to be bent.

Embodiments of the lung volume reduction system can be adapted to provide an implant that is constrained in a first configuration to a relatively straighter delivery configuration and allowed to recover in situ to a second configuration that is less straight configuration. Devices and implants can be made, at least partially, of spring material that will fully recover after having been strained at least 1%, suitable material includes a metal, such as metals comprising Nickel and Titanium. In some embodiments, the implant of the lung volume reduction system is cooled below body temperature in the delivered configuration. In such an embodiment, the cooling system can be controlled by a temperature sensing feedback loop and a feedback signal can be provided by a temperature transducer in the system. The device can be configured to have an Af temperature adjusted to 37 degrees Celsius or colder. Additionally, at least a portion of the metal of the device can be transformed to the martensite phase in the delivery configuration and/or can be in an austenite phase condition in the deployed configuration.

Lung volume reduction systems, such as those depicted in FIGS. 14-31, comprise an implantable device that is configured to be deliverable into a patient's lung and which is also configured to be reshaped to make the lung tissue that is in contact with the device more curved. Increasing the curvature of the tissue assists in reducing the lung volume of diseased tissue, which in turn increases the lung volume of healthier tissue. In some instances, the devices are configured to be reshaped to a permanent second configuration. However, as will be appreciated by those skilled in the art, the devices can also be adapted and configured to have a first shape and is configured to be strained elastically to a deliverable shape.

As will be appreciated by those skilled in the art, the devices illustrated in FIGS. 14-31 are can be configured to be deliverable into a patient's lung and configured to reshape lung tissue while allowing fluid to flow both directions past the implant. A number of additional features described in related U.S. patent application Ser. No. 12/558,206 entitled Enhanced Efficacy Lung Volume Reduction Devices, Methods, and Systems, such as lock features, decoupler systems, activation systems, and retrieval systems may be used with aspects of the present invention. The full disclosure of U.S. patent application Ser. No. 12/558,206 is incorporated herein by reference.

FIGS. 32A-C illustrates the process of implanting the device within a lung. As is evidence, the device 2810 is advanced is a configuration where the device adapts to the anatomy of the lungs through the airways and into, for example, the bronchioles until it reaches a desired location relative to the damaged tissue 32. The device is then activated by engaging the actuation device, causing the device to curve and pull the lung tissue toward the activated device (see, FIG. 32B). The device continues to be activated until the lung tissue is withdrawn a desired amount, such as depicted in FIG. 32C. As will be appreciated by those skilled in the art, withdrawing the tissue can be achieved by, for example, curving and compressing a target section of lung tissue upon deployment of one of the configurable devices disclosed herein. Once activated sufficiently, the deployment device is withdrawn from the lung cavity.

Figure 33A:
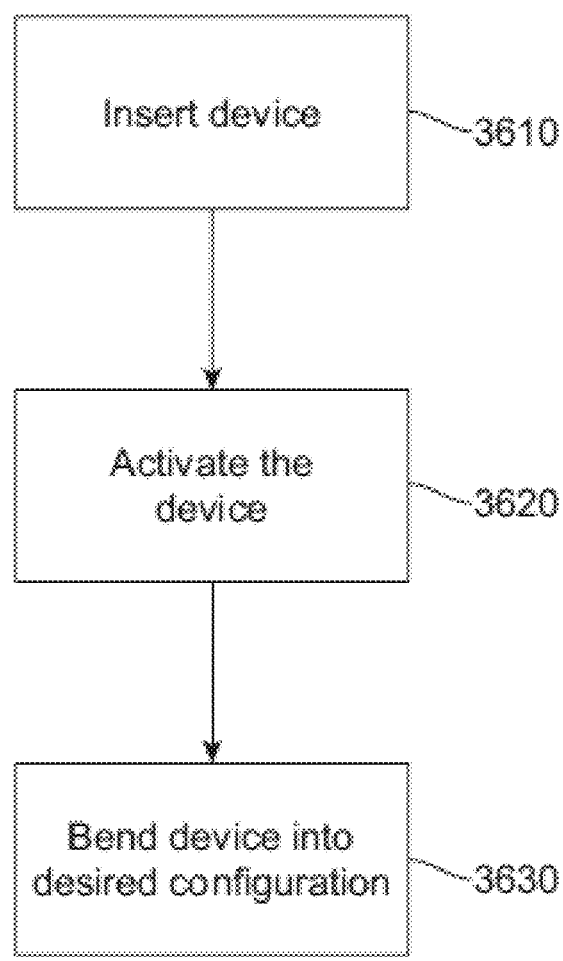
FIG. 33A illustrates a method steps for implanting the device.

A variety of steps for performing a method according to the invention would be appreciated by those skilled in the art upon review of this disclosure. However, for purposes of illustration, FIG. 33A illustrates the steps including, insertion of the device 3610, activating the device 3620, such as by activating an actuator; bending the device into a desired configuration 3630 and locking the device into a deployed condition. As will be appreciated the step of bending the device can be achieved by activating the actuator, as described above, or by the implant being restored into a preconfigured shape.

In one embodiment, the device operation includes the step of inserting a bronchoscope into a patient's lungs and then inserting an intra-bronchial device or lung volume reduction device into the bronchoscope. The intrabronchial device is then allowed to exit the distal end of the bronchoscope where it is pushed into the airway. A variety of methods can then be used to verify the positioning of the device to determine if the device is in the desired location. Suitable methods of verification include, for example, visualization via visualization equipment, such as fluoroscopy, CT scanning, etc. Thereafter the device is activated by pulling the pull wire proximally (i.e., toward the user and toward the exterior of the patient's body). At this point, another visual check can be made to determine whether the device has been positioned and deployed desirably. Thereafter, the device can be fully actuated and the ratchet can be allowed to lock and hold the device in place. Thereafter, the implant is decoupled from the delivery catheter and the delivery catheter is removed.

Figure 33B:
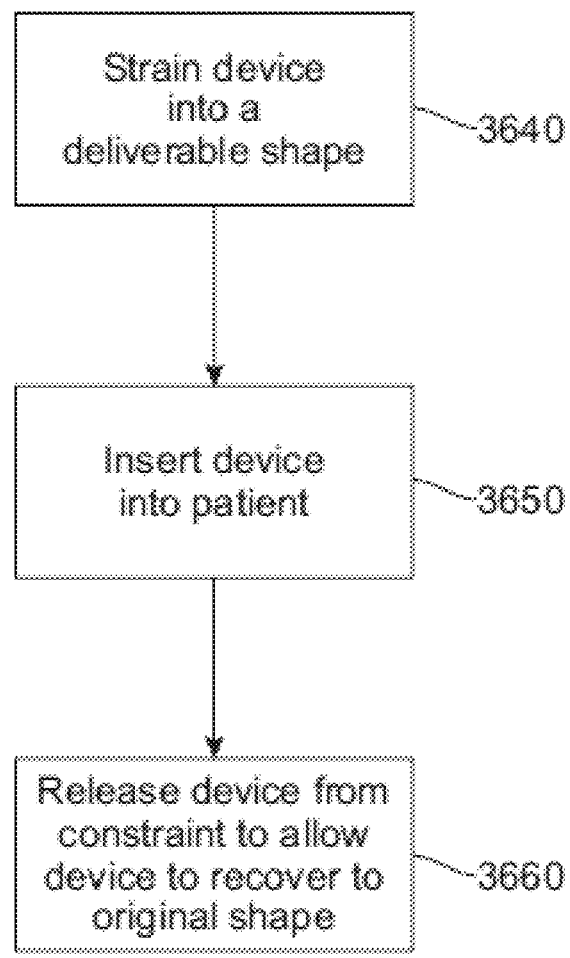
FIG. 33B illustrates a method steps for implanting the device.

Another method of tensioning the lung is shown in FIG. 33B which illustrates steps that include, applying bending loads or force to strain a device from a first shape into a deliverable shape without plastically or permanently bending the device 3640, delivering the device into the patient using the bronchoscope or other delivery system components to hold the device in a deliverable shape while it is being introduced 3650 and then removing the constraint used to hold the device to allow it to recover back to its first shape 3660. Elastic recovery of the device will drive the device to a more bent condition that will apply force to nearby lung tissue. The bending forces locally compress tissue near the implant and apply tension on lung tissue in surrounding regions to restore lung recoil and enhance breathing efficiency. The first shape is adapted to be elastically constrained by a delivery device to a deliverable configuration whereby removal of the delivery device allows the implant to recoil and be reshaped closer to its first shape.

Figure 34:
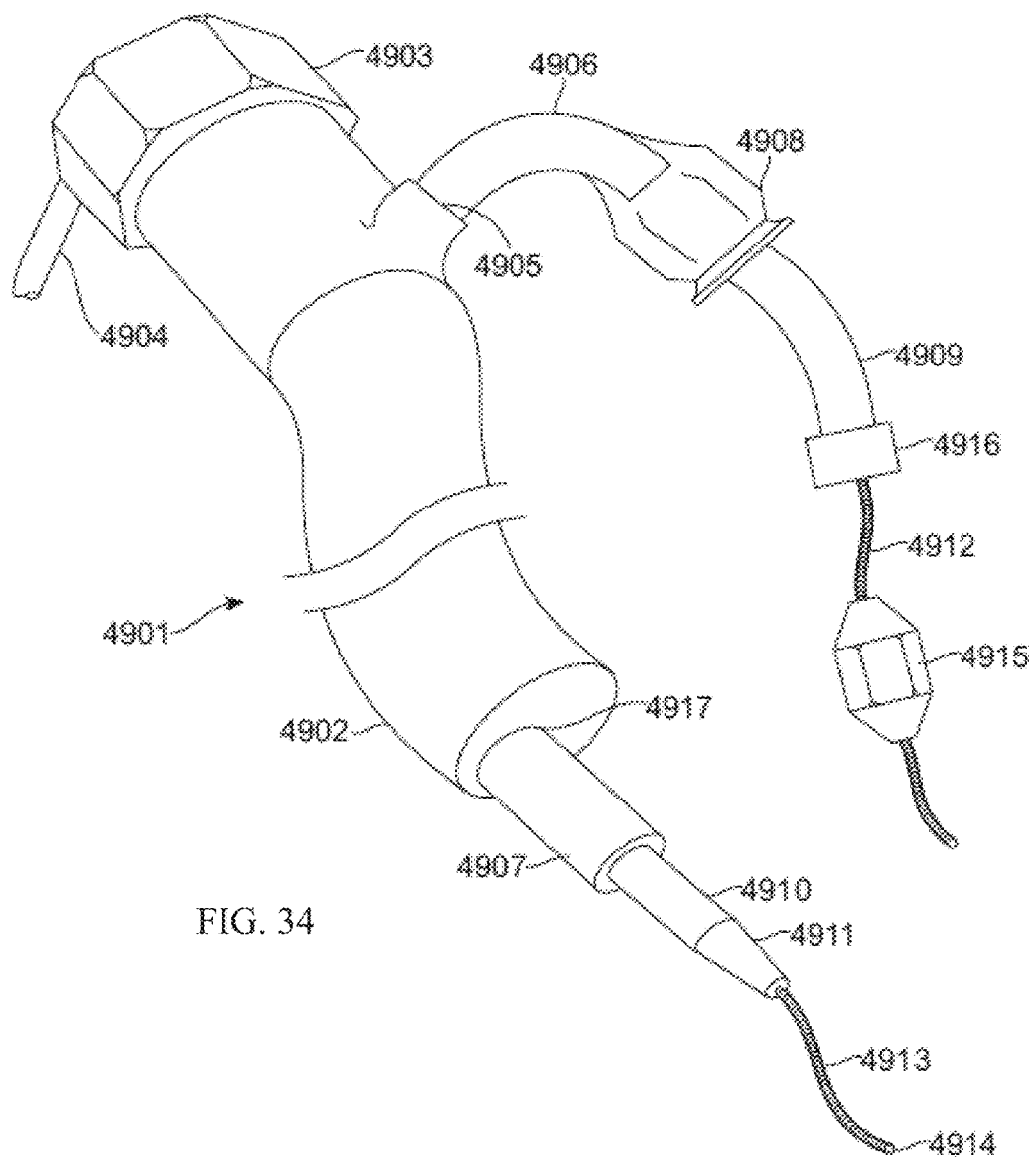
FIG. 34 illustrates a system in an airway with device ready to deliver.

FIG. 34 illustrates a system 4901 that may be used to deliver the implant device. The many components of the system may be needed to guide the bronchoscope 4902 to a site that is appropriate for implant delivery. The airway guide wire has a distal floppy section 4913 that can be steered into any desired airway by rotating the slight curve at the distal tip to the appropriate trajectory at airway bifurcations. To apply torque to the wire, devices such as a locking proximal handle 4915 may be attached to the proximal end of the wire 4912. The wire tip may be blunt such as the ball tip shown 4914. In some embodiments, the wire may be adapted and configured to pass through a dilator catheter 4909 that is shaped to provide a smooth diameter transition from the wire diameter to the delivery catheter 4906 diameter. The distal tip of the dilator 4910 should be tapered 4911 as shown. The dilator prevents the open end of the delivery catheter 4906 to dig into lung tissue in an unintended way. The dilator hub 4916 may be made as a Y-fitting to allow the user to couple a syringe and inject radiopaque dye through the dilator lumen to increase the visibility of the airways, which facilitates the use of an x-ray guidance system, such as fluoroscopy or computed tomography. The delivery catheter may be used without the wire and dilator. The catheter 4906 is designed to constrain the device in a deliverable shape while it is advanced through the system and into the patient. The distal end 4907 may be configured from a floppier polymer or braid than the proximal end 4906 and the distal tip may further include a radiopaque material associated with the tip, either integral or adjacent, to identify the position of the tip relative to other anatomical locations, such as bones. Providing one or more radiopaque markers facilitates using x-ray guidance system to position the distal end of the device in situ relative to a target anatomy. The proximal termination of the delivery catheter 4908 may further be adapted to incorporate a lockable hub to secure the loading cartridge 3801 with a smooth continuous lumen. The delivery catheter 4906 is shown introduced into the bronchoscope side port 4905 and out the distal end of the scope 4917. A camera 4903 is shown attached to the end of the scope with a cable 4904, or other delivery mechanism, to transmit the image signal to a processor and monitor. The loading cartridge, delivery catheter, dilator, guide wire and wire nut may be made from any material identified in this specification or materials well known to be used for similar products used in the human vascular tract by radiologists.

Figure 35:
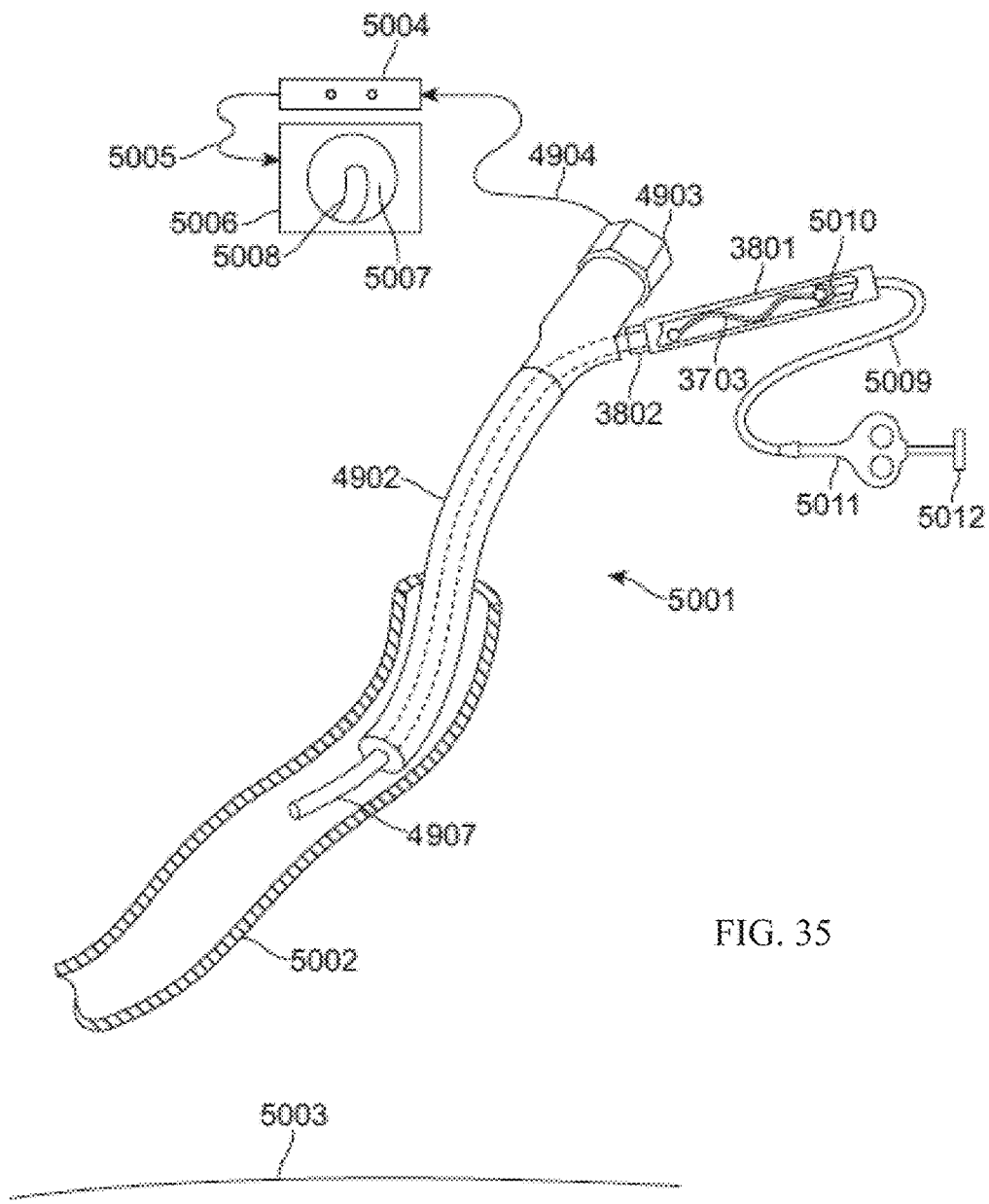
FIG. 35 illustrates a system in an airway delivering the device.

FIG. 35 illustrates a delivery system 5001 that has been placed into a human lung. The bronchoscope 4902 is in an airway 5002. The scope camera 4903 is coupled to a video processor 5004 via a cable 4904. The image is processed and sent through a cable 5005 to a monitor 5006. The monitor shows a typical visual orientation on the screen 5007 of a delivery catheter image 5008 just ahead of the optical element in the scope. The distal end of the delivery catheter 4907 protrudes out of the scope in an airway 5002 where the user will place an implant device 3703. The implant 3703 is loaded into a loading cartridge 3801 that is coupled to the proximal end of the delivery catheter via locking hub connection 3802. A pusher grasper device 5009 is coupled to the proximal end of the implant 3703 with a grasper coupler 5010 that is locked to the implant using an actuation plunger 5012, handle 5011 and pull wire that runs through the central lumen in the pusher catheter. By releasably coupling the pusher to the implant device and advancing pusher/grasper device 5009, the user may advance the implant to a position in the lung in a deployed configuration. The user can survey the implant placement position and still be able to retrieve the implant back into the delivery catheter, with ease, if the delivery position is less than ideal. The device has not been delivered and the bottom surface of the lung 5003 is shown as generally flat and the airway is shown as generally straight. These may both be anatomically correct for a lung with no implant devices. If the delivery position is correct, the user may actuate the plunger 5012 to release the implant into the patient.

Figure 36:
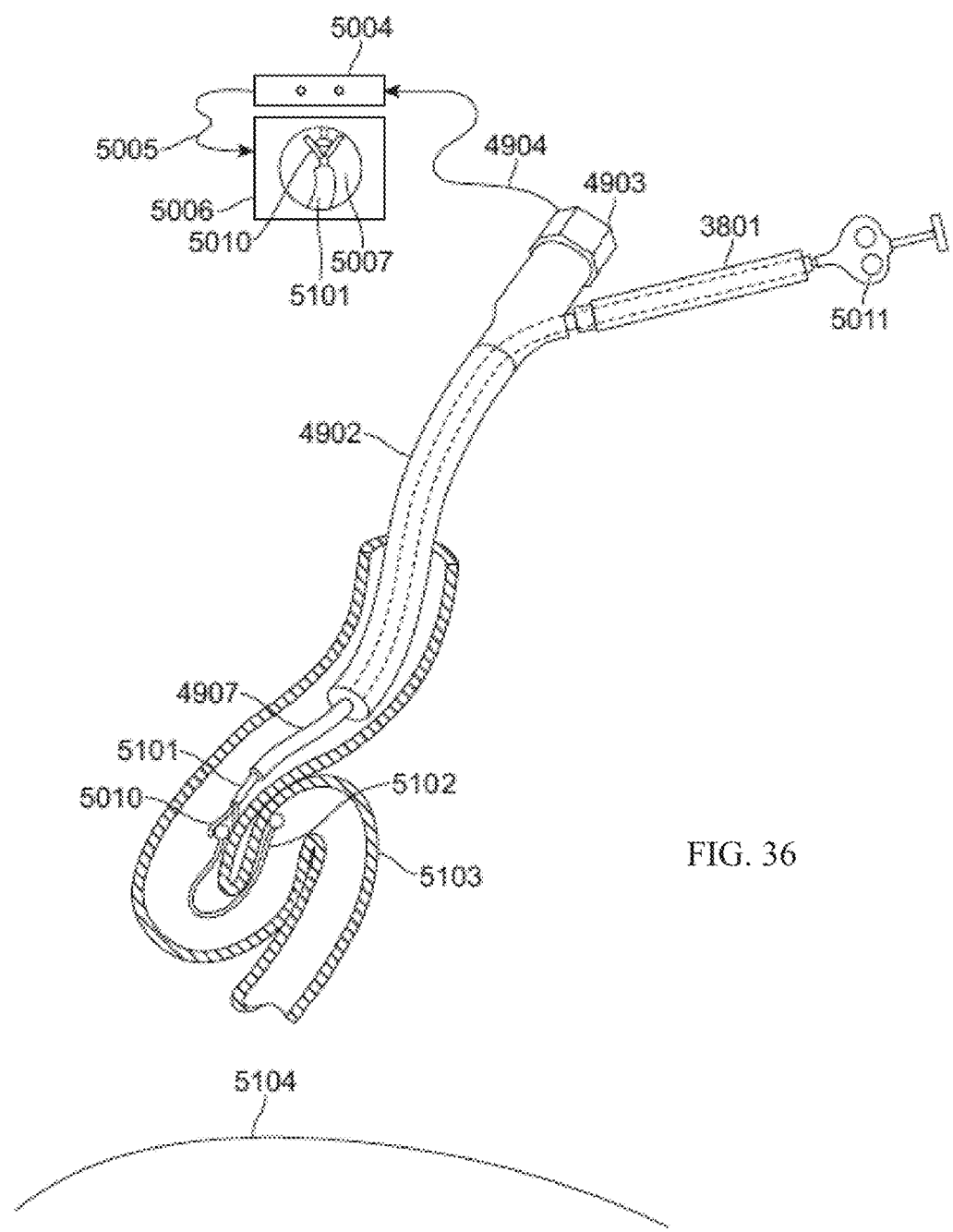
FIG. 36 illustrates a system in an airway with the device delivered.

FIG. 36 illustrates generally the same system after the implant has been deployed into the airway 5103. The implant 5102 and pusher 5101 has been advanced through the delivery catheter 4907 to a location distal to the scope 4902. The pusher grasping jaws 5010 are still locked onto the proximal end of the implant 5102 but the implant has recovered to a pre-programmed shape that has also bent the airway 5103 into a folded configuration. By folding the airway, the airway structure has been effectively shortened within the lung and lung tissue between portions of the implant has been laterally compressed. Since the airways are well anchored into the lung tissue, the airway provides tension on the surrounding lung tissue which is graphically depicted by showing the pulled (curved inward) floor of the lung 5104. The image from the camera 4903 is transmitted through the signal processor 5004 to the monitor 5006 to show the distal tip of the delivery catheter 5101, distal grasper of the pusher 5010 and proximal end of the implant 3703. The grasper may be used to locate, couple to and retrieve devices that have been released in the patient. The implant performs work on the airways and lung tissue without blocking the entire lumen of the airway. This is a benefit in that fluid or air may pass either way through the airway past the implant device.

Figure 37:
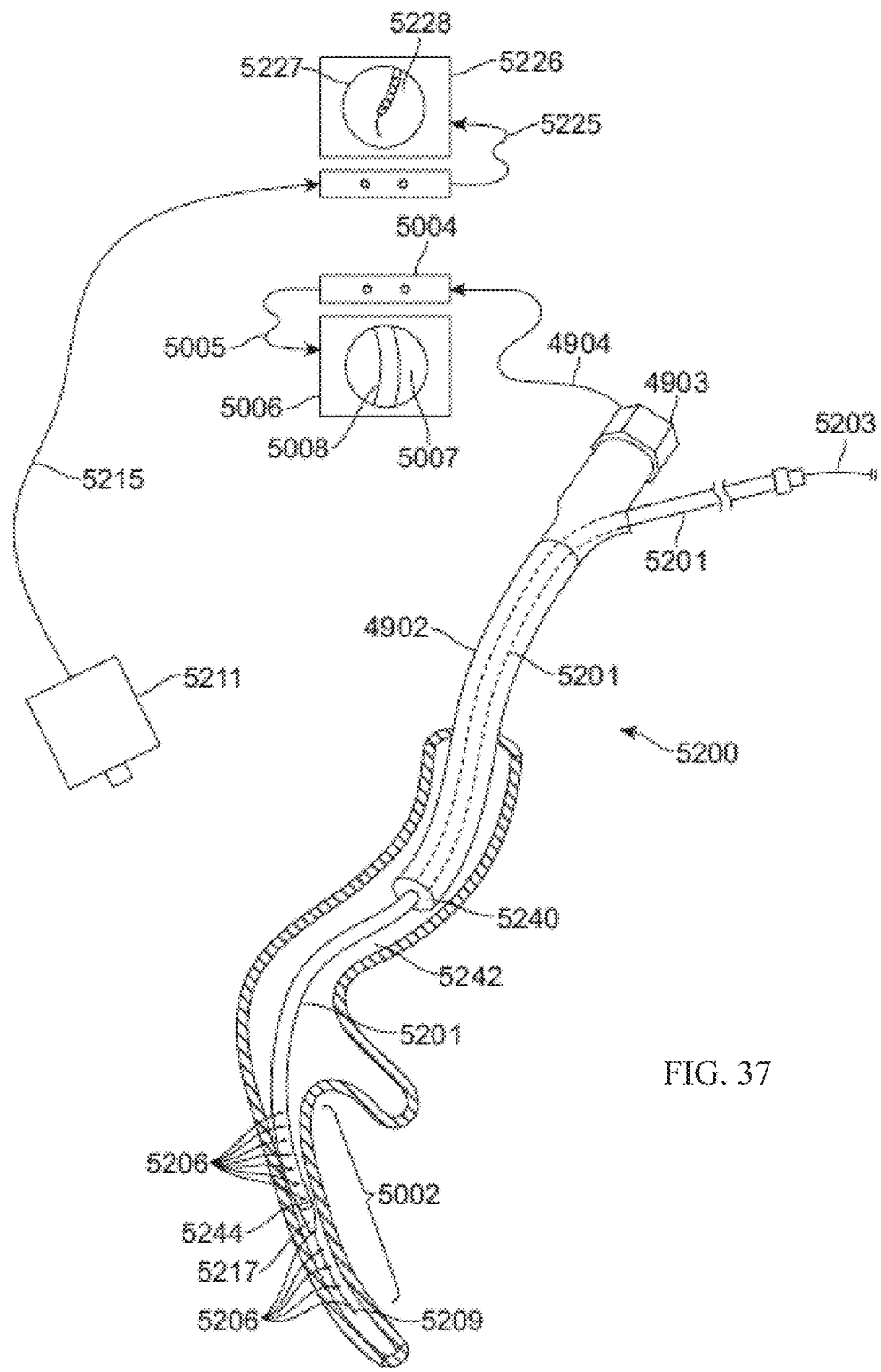
FIG. 37 illustrates a system with a bronchoscope, catheter, dilator, and guidewire.

FIG. 37 illustrates delivery system 5200 as placed into a patient body, and particularly into a human lung. Delivery system 5200 may be generally similar to system 4901 or 5001 described above. The distal end 5240 of bronchoscope 4902 extends into an airway system toward an airway portion or axial region 5002, sometimes referred to as an axial segment. The scope camera 4903 is coupled to a video processor 5004 via a cable 4904. The image is processed and sent through a cable 5005 to a monitor 5006. Monitor 5006 shows on screen 5007 a portion of a delivery catheter image 5008 just ahead of the optical image capture element in the scope. In some embodiments, the scope may be constrained by a relatively large cross-section to advancement only to a "near" region of the lung adjacent the major airways. Hence, the optical image has a viewfield that extends only a limited distance along the airway system, and it will often be desirable to implant some, most, or all of the implant beyond a field of view 5242 of scope 4902.

Guidewire 5203 is threaded through bronchoscope 4902 and through the airway system to (and through) airway 5002. As described above, guidewire 5203 may optionally have a cross-section significantly smaller than that of the scope and/or the delivery catheter. Alternative embodiments may use a relatively large diameter guidewire. For example, rather than relying on a tapering dilator between the guidewire and the delivery catheter, the guidewire may instead be large enough to mostly or substantially fill the lumen of the delivery catheter, while still allowing sliding motion of the guidewire through the lumen. Suitable guidewires may have cross-section in a range from about 5 Fr to about 7 Fr, ideally being about 5½ Fr, while the delivery catheter may be between about 5 Fr and 9 Fr, ideally being about 7 Fr. A distal end 5209 of the guidewire 5203 may be angled as described above to facilitate steering. Still further variations are also possible, including delivery of the implant directly thru a working lumen of an endoscope (with use of a separate delivery catheter). In particular, where a cross-sectional size of a bronchoscope allows the scope to be advanced to a distal end of the target airway region, the bronchoscope itself may then be used as a delivery catheter, optionally without remote imaging.

A fluoroscopic system, an ultrasound imaging system, an MRI system, a computed tomography (CT) system, or some other remote imaging modality having a remote image capture device 5211 allows guidance of the guidewire so that the guidewire and/or delivery catheter 5201 can be advanced beyond the viewing field of bronchoscope 4902. In some embodiments, the guidewire may be advanced under remote image guidance without the use of a scope. Regardless, the guidewire can generally be advanced well beyond the near lung, with the distal end of the guidewire often being advanced to and/or through the mid-lung, optionally toward or to the small airways of the far lung. When a relatively large guidewire is used (typically being over 5 Fr., such as a 5½ Fr guidewire), the cross-section of the guidewire may limit advancement to a region of the airway having a lumen size appropriate for receiving the implants described above. The guidewire may have an atraumatic end, with exemplary embodiments having a guidewire structure which includes a corewire affixed to a surrounding coil with a resilient or low-column strength bumper extending from the coil, the bumper ideally formed by additional loops of the coil with separation between adjacent loops so as to allow the bumper to flex axially and inhibit tissue damage. A rounded surface or ball at the distal end of the bumper also inhibits tissue injury. A distal end 5244 of laterally flexible delivery catheter 5201 can then be advanced through the lumen within bronchoscope 4902 and over guidewire 5203 under guidance of the imaging system, ideally till the distal end of the delivery catheter is substantially aligned with the distal end of the guidewire.

The distal portion of guidewire 5203 is provided with indicia of length 5206, the indicia indicating distances along the guidewire from distal end 5209. The indicia may comprise scale numbers or simple scale markings, and distal end 5244 of catheter 5201 may have one or more corresponding high contrast markers, with the indicia of the guidewire and the marker of the catheter typically visible using the remote imaging system. Hence, remote imaging camera 5211 can identify, track or image indicia 5206 and thus provide the length of the guidewire portion extending between (and the relative position of) the distal end of the bronchoscope and the distal end 5209 of guidewire 5203. Indicia of length 5206 may, for example, comprise radiopaque or sonographic markers and the remote imaging modality may comprise, for example, an x-ray or fluoroscopic guidance system, a computed tomography (CT) system, an MRI system, or the like. Exemplary indicia comprise markers in the form of bands of high-contrast metal crimped at regular axial intervals to the corewire with the coil disposed over the bands, the metal typically comprising gold, platinum, tantalum, iridium, tungsten, and/or the like. Note that some of the indicia of the guidewire are schematically shown through the distal portion of the catheter in FIG. 37. Indicia of length 5206 thus facilitate using a guidance system to measure a length of airway 5002 or other portion of the airway system beyond the field of view of the scope, thereby allowing an implant of appropriate length to be selected.

Remote imaging modality 5221 is coupled to imaging processor 5224 via cable 5215. Imaging processor 5224 is coupled to a monitor 5226 which displays an image 5228 on screen 5227. Image 5228 shows the indicia of lengths 5205 and 5206 of delivery catheter 5201 and guidewire 5203, respectively. As described above, when a small-diameter guidewire is used a dilator 5217 may be advanced through the lumen of the catheter so that the distal end of the dilator extends from the distal end of delivery catheter 5201 when the catheter is being advanced. Dilator 5217 atraumatically expands openings of the airway system as delivery catheter 5201 advances distally. Dilator 5217 tapers radially outwardly proximal of the distal tip of guidewire 5203, facilitating advancement of the catheter distally to or through the mid-lung toward the far lung. Once the catheter has been advanced to the distal end of airway portion 5002 targeted for delivery (optionally being advanced over the guidewire to the distal end of the guidewire when a large diameter guidewire is used to identify a distal end of a target region for an implant, or as far as the cross-section of the catheter allows the catheter to be safely extended over a smaller diameter guidewire), the length of the airway (optionally between the distal end of the guidewire and the distal end of the bronchoscope) is measured. The dilator 5217 (if used) and guidewire 5203 are typically withdrawn proximally from deliver catheter 5201 so as to provide an open lumen of the delivery catheter from which a lung volume reduction device or implant can be deployed.

Figure 38A:
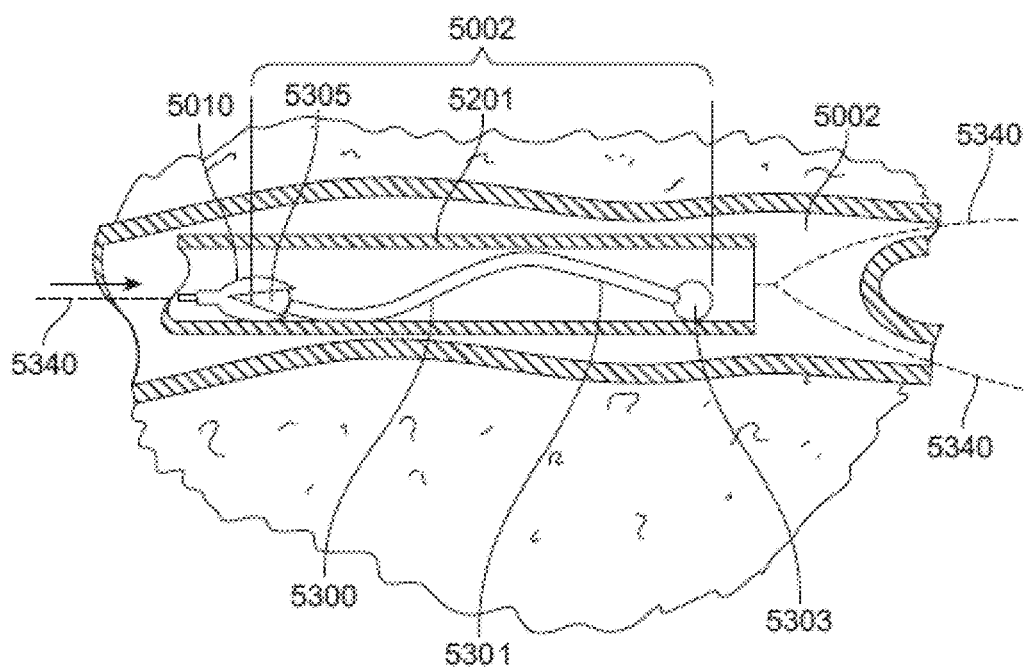
FIGS. 38A-38B illustrate the delivery of the device.
Figure 38B:
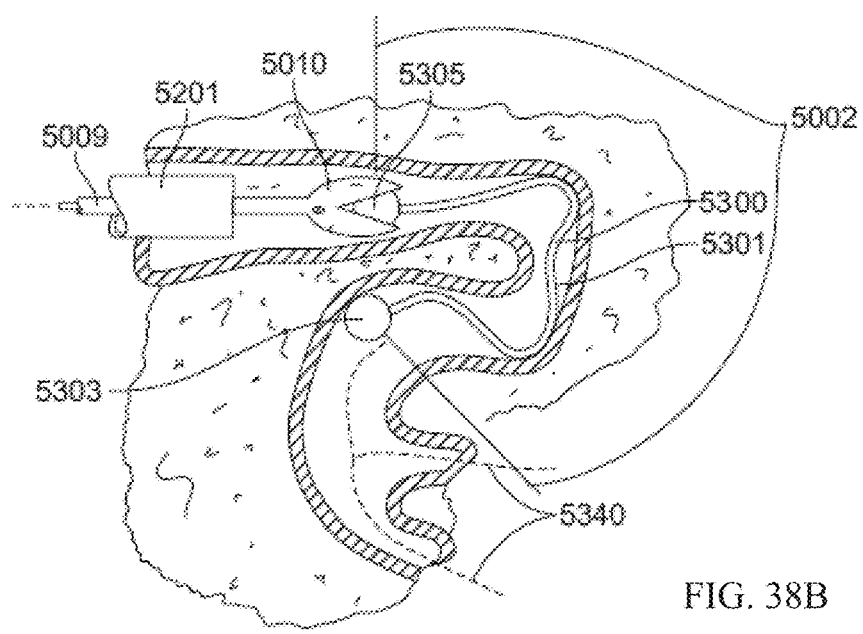

FIGS. 38A and 38B show an implant 5300 for treating airway 5002 of a lung. As described above, airway 5002 comprises a portion of a branching airway system, and the airway targeted for deployment will typically define an airway axis 5340. Implant 5300 comprises an elongate body 5301, a distal end 5303, and a proximal end 5305. Elongate body 5301 is biased to bend to a bent deployed configuration as described above and as shown in FIG. 38B. A pusher grasper device 5009 is coupled to the proximal end 5305 with a grasper coupler 5010 that is locked to implant 5300 using an actuation plunder 5012, handle 5011, and pull wire that runs through the central lumen in the pusher catheter. Prior to deployment, implant 5300 may be loaded into a tubular loading cartridge, for example, cartridge 3801, and advanced from the loading cartridge into the lumen of catheter 5301. Pusher grasper device 5009 can advance implant 5300 through delivery catheter 5201. As shown in FIG. 38A, when restrained within delivery catheter 5201, elongate body 5301 is maintained in a straightened configuration which defines a long axis between the distal end 5303 and proximal end 5305. As shown in FIG. 38B, when pusher grasper device 5009 axially restrains implant 5300 and catheter 5201 is pulled proximally from airway axial region 5002, implant 5300 resiliently returns to a bent deployed configuration to bend the airway 5002. More specifically, the airway axis 5340 goes from a relatively straight configuration to a highly bent configuration, with lateral movement of the elongate body and surrounding airway structure thereby compressing adjacent tissue. Once catheter 5201 has been withdrawn from over elongate body 5301, the deployment can be evaluated. The user may axially restrain the implant 5300 while catheter 5201 is advanced axially so as to recapture the implant if the deployment does not appear satisfactory, or the user may actuate plunger 5012 to release implant 5300. Implant 5300 may be loaded into a tubular loading cartridge, for example, cartridge 3801, and advanced from the loading cartridge into the lumen of catheter 5301.

Figure 39:
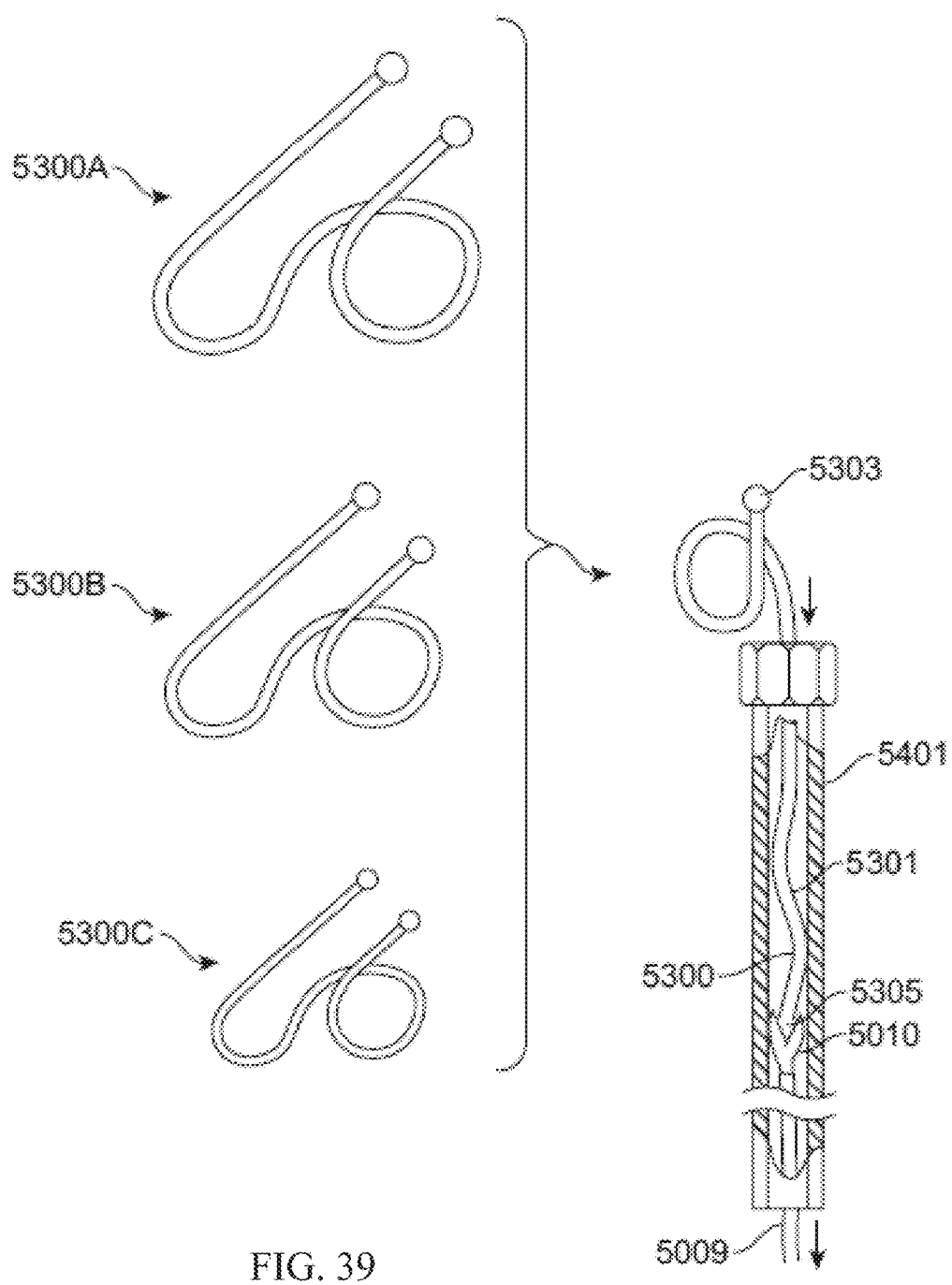
FIG. 39 schematically illustrates selection from among a plurality of alternative devices with different lengths, and loading of a device into a cartridge so that the device can be advanced into a delivery catheter.

FIG. 39 shows a plurality of implants including implant 5300A, 5300B, and 5300C. Each of these implants may have different sizes, lengths, and shapes from each other. When using delivery system 5200, guidewire 5203 may be advanced to a target region near the distal end of the airway system. Guidewire 5203 may be advanced distally until further distal advancement is limited by the distal end of the guidewire being sufficiently engaged by the surrounding lumen of the airway system. Delivery catheter 5201 can then be advanced so that a distal end of catheter 5201 is adjacent a distal end of the guidewire. The distance along the indicia of length 5205 from the bronchoscope to the distal end of guidewire 5203 may be used to select an implant having an elongate body 5301 with a desired length. The desired length may be lesser, greater or about the same as the distance between the distal end of delivery catheter 5201 and distal end of the bronchoscope as indicated by the indicia 5206. The elongate body 5301 having the selected length may be advanced and deployed into the lung via the airway system and using pusher grasper 5009 as described above. To provide a desirable implant shelf life and/or a desirable deployment force for compressing tissues using self-deploying elongate bodies (including those using resilient materials and/or using superelastic materials such as Nitinol™ or the like), it may be advantageous to store the various implants of various sizes in a relaxed state. Once the desired implant geometry or other characteristics have been identified, the selected implant 5300 may be loaded into a loading cartridge 5401 (and subsequently into the lumen of delivery catheter 5201) using pusher grasper device 5009. Pusher grasper device 5009 may be tensioned proximally and/or loading cartridge 5401 may be pushed distally so that elongate body 5301 straightens axially. The loading cartridge 5401 and implant 5300 can then be coupled to the other components of the delivery system, and the implant advanced into the airway as described above.

In exemplary embodiments, the pusher grasper 5009 moves distally while the catheter 5201 is retracted proximally from over the implant during deployment. The selected implant may have a length greater than the measured distance between the distal end of the guidewire (and hence the end of the delivery catheter) and the distal end of the scope. This can help accommodate recoil or movement of the ends of the implant toward each during delivery so as to avoid imposing excessive axial loads between the implant and tissue. Distal movement of the pusher grasper 5009 and proximal end of the implant during deployment also helps keep the proximal end of the implant within the field of view of the bronchoscope, and enhances the volume of tissue compressed by the implant. Exemplary implants may be more than 10% longer than the measured target airway axial region length, typically being from 10% to about 30% longer, and ideally being about 20% longer. Suitable implants may, for example, have total arc lengths of 125, 150, 175, and 200 mm.

Related U.S. patent application Ser. No. 12/558,206 describes exemplary methods for treating a patient and evaluating the treatment, each of which may be used with aspects of the present invention. For example, the treatment method may comprise delivering an implant within the lung and then evaluating the patient's breathing thereafter to determine whether more implants are needed. Alternatively, a plurality of implants may be delivered within the patient's lungs before an evaluation. The patient's lungs may be evaluated by measuring a forced expiratory volume (FEV) of the patient, measuring/visualizing a change in tissue density at the implantation region, measuring/visualizing displacement of the diaphragm or of the lung fissures, etc.

In some embodiments, an implant is deployed in a straight configuration with the use of a catheter, e.g., catheter 5201, to contain it in a generally straight shape. Alternative embodiments may use the working lumen of the bronchoscope directly so that the bronchoscope is used as a delivery catheter. Upon removal of the constraining catheter, the implant recoils to a deployed shape that can be easily identified by the fact that the distance from one end to the second is reduced. The proximal end of the implant may be grasped, e.g., with pusher grasper device 5009, and held so that the distal end of the implant remains engaged against the desired airway tissue as the length of the implant is progressively unsheathed (by withdrawing the catheter proximally). High tensile forces might be generated between the distal portion of the implant and the airway tissue if the proximal end of the implant is held at a fixed location throughout deployment, as the implant is biased to recoil or bring the ends together when released. Hence, it can be advantageous to allow the proximal end of the implant to advance distally during release, rather than holding the implant from recoiling, as these forces may be deleterious. For example, the distance and tissue thickness between the distal end of the implant and the lung surface is short, there may be little strain relief on the tissue and the risk of rupture may be excessive. Additionally, the implant might otherwise tend to foreshortened after it is released by the grasper. When foreshortening occurs, the proximal end of the implant may travel distally beyond the viewing field of the bronchoscope and the user can have difficulty retrieving the implant reliably.

Figure 40A:
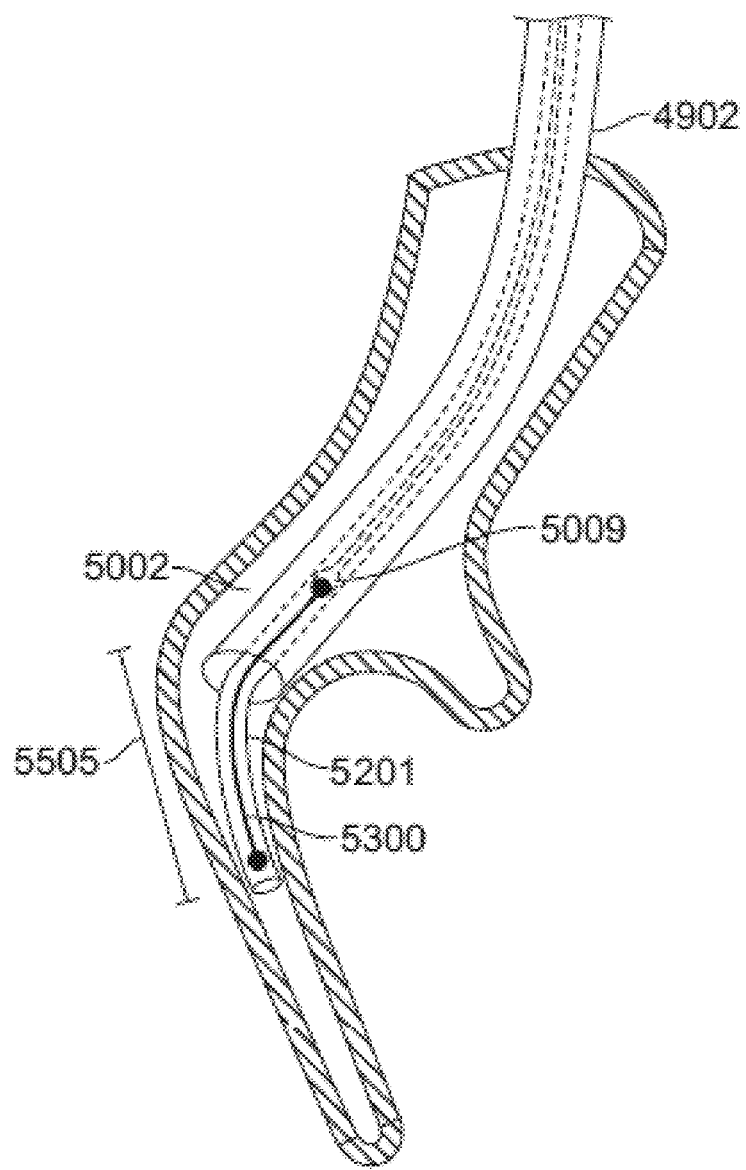
FIGS. 40A-40C illustrate the delivery of a lung volume reduction device according to embodiments of the invention.
Figure 40B:
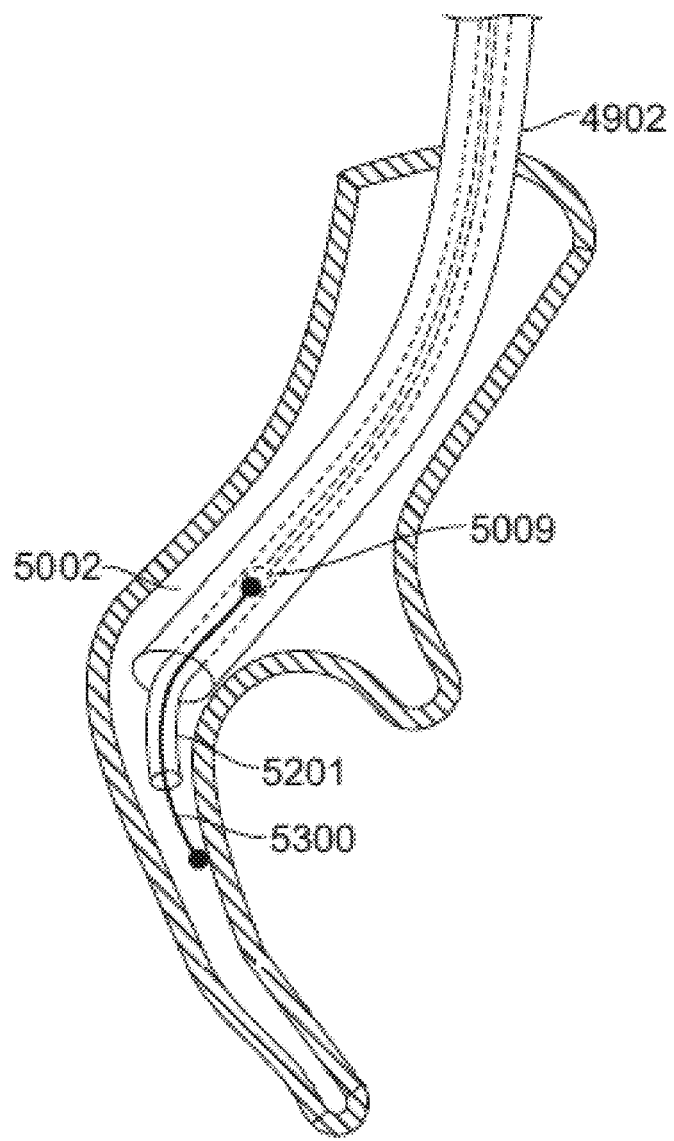
Figure 40C:
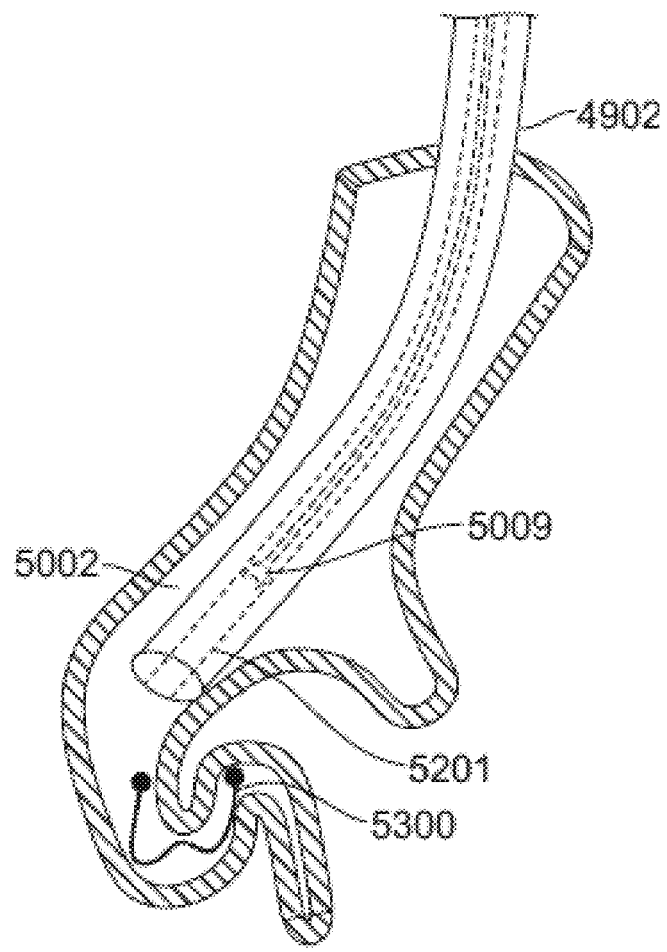

Thus, as schematically shown in FIGS. 40A-40C, an implant 5300 having a length longer than that of the target axial region 5505 may be selected to be deployed in some cases. As described above, a guidewire may be advanced distally from the bronchoscope until the guidewire advancement is inhibited by engagement with the surrounding airway, with the guidewire optionally being relatively large in cross-section (such having a size of between about 5 F and 7 F, ideally having a size of about 5½ F). This allows the guidewire to be advanced to (but not excessively beyond) a target site for the distal end of the implant (which may have an atraumatic ball surface with a diameter from about 1 to about 3 mm, ideally being about 1.5 mm). As shown in FIG. 40A, catheter 5201 is advanced distally from the distal end of bronchoscope 4902 over the guidewire until the distal end of catheter 5201 is aligned with the distal end of the guidewire or till the distal end of the catheter limits further distal advancement due to the distal end of catheter 5201 being similarly sufficiently engaged by the surrounding lumen of the airway system 5002. A length 5505 of the target axial region of the airway is measured. Length 5505 may be the distance between the distal end of the advanced catheter 5201 and the distal end of the bronchoscope 4902, and the guidewire can be withdrawn proximally after the measurement. An implant 5300 having a length greater than the measured length 5505 is selected and distally advanced through catheter 5201 using pusher grasper 5009 as previously described. Implants having a length of at least 10% more, preferably about 20% more, than the measured target axial region may be selected.

FIG. 40B shows the deployment of implant 5300. Implant 5300 is advanced through the lumen of catheter 5201 to adjacent its distal end and the catheter 5201, the distal end of the implant is (at least initially) held axially in place, and the catheter is withdrawn proximally from over a distal portion of the implant. As catheter 5201 is withdrawn, implant 5300 bends laterally and compresses a portion of airway 5002. As shown in FIG. 40B, a larger portion airway 5002 can be compressed by implant 5300 once catheter 5201 is fully withdrawn such that it no longer restrains implant 5300. As the catheter is progressively withdrawn, the proximal end of the implant moves distally relative to the surrounding bronchoscope and airway tissue. The proximal end of implant 5300 may also be released by pusher grasper 5009 after implant 5300 has foreshortened (when measured along the axial center of the airway) gradually throughout its release.

By using a longer implant 5300, the proximal end of implant 5300 can also be fed into the airway while the potential energy of the implant is being freed to apply work on the lung tissue (while the catheter is being pulled off of the implant). The lung airways can be distorted so the airway cross section is pushed to a more oval shape. Longer implants can tend to zigzag back and forth across the airway lumen so that implants that are significantly longer than the measured airway length can be introduced. For example, a 150 mm long (arc length) implant can be deployed into a 100 mm long airway. The greater length of the implant may minimize the uncontrolled recoil that may cause the proximal end to be lost in the patient upon release. Greater implant length can also allow the user to feed the implant into the patient while the catheter is removed without over stressing the lung tissue. Additionally, should foreshortening of the longer implant occur, the proximal end of the implant can still remain within the viewing field of the bronchoscope and the user can thus retain the ability to retrieve the implant reliably. It should be understood that the length of the implant relative to the diameter of the airway may be much greater than the schematic illustration of FIGS. 40A-40C, that the implant may have more complex three dimensional curvature to effect volumetric compression of the lung tissue, and the like.

As will be appreciated by those skilled in the art, the device can be manufactured and deployed such that it is deliverable through a bronchoscope. When actuated, the device can be adapted and configured to bend or curl which then distorts lung tissue with which the device comes in contact. Lung tissues that may be beneficially distorted by the device are airways, blood vessels, faces of tissue that have been dissected for introduction of the device or a combination of any of these. By compressing the lung tissue, the device can result in an increase in elastic recoil and tension in the lung in at least some cases. Additionally, in some instances, lung function can be at least partially restored regardless of the amount of collateral ventilation. Further, the diaphragm may, in some instances, move up once greater tension is created which enables the lung cavity to operate more effectively.

Devices according to the invention have a small cross-section, typically less than 10 F. The flexibility of the device prior to deployment facilitates advancement of the device through the tortuous lung anatomy. Once deployed, the device can remain rigid to hold and maintain a tissue deforming effect. Further, the device design facilitates recapture, de-activation and removal as well as adjustment in place.

Candidate materials for the devices and components described herein would be known by persons skilled in the art and include, for example, suitable biocompatible materials such as metals (e.g. stainless steel, shape memory alloys, such a nickel titanium alloy (nitinol), titanium, and cobalt) and engineering plastics (e.g. polycarbonate). See, for example U.S. Pat. No. 5,190,546 to Jervis for Medical Devices Incorporating SIM Memory Alloy Elements and U.S. Pat. No. 5,964,770 to Flomenblit for High Strength Medical Devices of Shape Memory Alloy. In some embodiments, other materials may be appropriate for some or all of the components, such as biocompatible polymers, including polyetheretherketone (PEEK), polyarylamide, polyethylene, and polysulphone.

Polymers and metals used to make the implant and delivery system may be coated with materials to prevent the formation and growth of granular tissue, scar tissue and mucus. Many of the drugs used with stent products to arrest hyperplasia of smooth muscle cells in blood vessels after deploying metallic stents will work very well for these devices. Slow release drug eluting polymers or solvents may be used to regulate the release of drugs that include any substance capable of exerting a therapeutic or prophylactic effect for a patient. For example, the drug could be designed to inhibit the activity of smooth muscle cells. It can be directed at inhibiting abnormal or inappropriate migration and/or proliferation of smooth muscle cells to inhibit tissue mass buildup. The drug may include small molecule drugs, peptides or proteins. Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin$_1$, actinomycin X$_1$, and actinomycin C$_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co. of Stamford, Conn.), docetaxel (e.g. Taxotere®, from Aventis S. A. of Frankfurt, Germany) methotrexate, azathioprine, vincristine, vinblastine, fluorouracil, doxorubicin hydrochloride (e.g. Adriamycin® from Pharmacia & Upjohn of Peapack N.J.), and mitomycin (e.g. Mutamycin® from Bristol-Myers Squibb). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hh/IIIa platelet membrane receptor antagonist antibody, recombinant hirudin, and thrombin inhibitors such as Angiomax™ (Biogen, Inc. of Cambridge, Mass.). Examples of such cytostatic or antiproliferative agents include angiopeptin, angiotensin converting enzyme inhibitors such as captopril (e.g. Capoten® and Capozide® from Bristol-Myers Squibb), cilazapril or Hsinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which jtnay be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis of New York, N.Y.), 40-O-(3-hydroxy)propyl-rapamycin, 40-O-[2-(2-hydroxy)ethoxy]ethyl-rapamycin, and 40-O-tetrazole-rapamycin.

Other polymers that may be suitable for use in some embodiments, for example other grades of PEEK, such as 30% glass-filled or 30% carbon filled, provided such materials are cleared for use in implantable devices by the FDA, or other regulatory body. The use of glass filled PEEK would be desirable where there was a need to reduce the expansion rate and increase the flexural modulus of PEEK for the instrument Glass-filled PEEK is known to be ideal for improved strength, stiffness, or stability while carbon filled PEEK is known to enhance the compressive strength and stiffness of PEEK and lower its expansion rate. Still other suitable biocompatible thermoplastic or thermoplastic polycondensate materials may be suitable, including materials that have good memory, are flexible, and/or deflectable have very low moisture absorption, and good wear and/or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK), and generally a polyaryletheretherketone. Further other polyketones can be used as well as other thermoplastics. Reference to appropriate polymers that can be used in the tools or tool components can be made to the following documents, all of which are incorporated herein by reference. These documents include: PCT Publication WO 02/02158 A1, to Victrex Manufacturing Ltd. entitled Bio-Compatible Polymeric Materials; PCT Publication WO 02/00275 A1, to Victrex Manufacturing Ltd. entitled Bio-Compatible Polymeric Materials; and PCT Publication WO 02/00270 A1, to Victrex Manufacturing Ltd. entitled Bio-Compatible Polymeric Materials. Still other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used as well for portions of the instrument that are desired to be radiolucent.

The implant described herein can be made of a metallic material or an alloy such as, but not limited to, cobalt-chromium alloys (e.g., ELGILOY), stainless steel (316L), "MP3SN," "MP2ON," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP2ON" are trade names for alloys of cobalt, nickel, chromium and molybdenum available from Standard Press Steel Co. of Tenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims presented will define the scope of the invention and that methods and structures within the scope of these claims and their equivalents be covered thereby.

What is claimed is:

1. A lung volume reduction system for enhancing a breathing efficiency of a patient with an airway, the system comprising:
   an implantable device having an elongate body including a proximal end and a distal end, the implantable device further having a first configuration and a second configuration, the second configuration of the implantable device corresponding to a configuration of the implantable device pre-implantation or post-implantation, the second configuration comprising at least one helical section;
   wherein the at least one helical section includes a proximal portion, a distal portion, and a helical axis, the proximal portion and the distal portion of the at least one helical section configured to compress lung tissue disposed between the proximal portion and the distal portion;
   wherein the elongate body transitions from the at least one helical section to a stand-off proximal tail at the proximal end of the elongate body, the stand-off proximal tail comprising a distal portion adjacent to and bending from the at least one helical section, a proximal portion, and a bend disposed between the distal portion and the proximal portion.

2. The lung volume reduction system of claim 1, wherein the distal portion of the stand-off proximal tail is straight.

3. The lung volume reduction system of claim 2, wherein the proximal portion of the stand-off proximal tail is straight.

4. The lung volume reduction system of claim 1, wherein the second configuration comprises at least two helical sections, each of the at least two helical sections including a proximal portion, a distal portion, and a helical axis.

5. The lung volume reduction system of claim 4, wherein the respective helical axes are different when the implantable device is in the second configuration.

6. The lung volume reduction system of claim 4, wherein an angle between the respective helical axes is between about 190 degrees and 230 degrees when the implantable device is in the second configuration.

7. The lung volume reduction system of claim 4, wherein the respective helical axes are the same when the implantable device is in the second configuration.

8. The lung volume reduction system of claim 4, wherein the implantable device is configured to impart a compression force on lung tissue of the patient.

9. The lung volume reduction system of claim 8, wherein the proximal portion and the distal portion of each of the at least two helical sections are configured to compress lung tissue disposed between the proximal portion and the distal portion of each respective helical section.

10. The lung volume reduction system of claim 4, wherein the stand-off proximal tail extends away from the proximal portion of the respective helical axis of the at least two helical sections when the implantable device is in the second configuration.

11. The lung volume reduction system of claim 4, wherein a transition section disposed between the at least two helical sections transitions between oppositely handed helical configurations.

12. The lung volume reduction system of claim 11, wherein the transition section is configured to reduce recoil forces during implantation of the implantable device.

13. The lung volume reduction system of claim 11, wherein the transition section is configured to reduce migration of the implantable device post-implantation.

14. The lung volume reduction system of claim 13, wherein the transition section is configured to maintain compression force on lung tissue of the patient.

15. The lung volume reduction system of claim 4, wherein the at least two helical sections each include at least one complete helix turn.

16. The lung volume reduction system of claim 4, wherein the at least two helical sections include the same number of complete helix turns.

17. The lung volume reduction system of claim 4, wherein the at least two helical sections include a different number of complete helix turns.

18. The lung volume reduction system of claim 1, wherein the at least one helical section comprises a circular, conical, or spherical helical section in the second configuration.

19. The lung volume reduction system of claim 1, wherein at least a portion of the implantable device is covered by a jacket, the jacket configured to increase the diameter of the implantable device and provide more area per unit force post-implantation.

20. A method of enhancing breathing efficiency of a patient with a lung having an airway, the method comprising:
   providing an implant, the implant having an elongate body including a proximal end and a distal end;
   advancing the implant distally through the airway toward a target site of the lung of the patient while the implant is in a delivery configuration;
   deploying the implant at the target site of the lung by transitioning the implant from the delivery configuration to a deployed configuration, the deployed configuration of the implant comprising at least one helical section;
   wherein the at least one helical section includes a proximal portion, a distal portion and a helical axis; and wherein the proximal portion and the distal portion of the at least one helical section are configured to compress lung tissue disposed between the proximal portion and the distal portion at the target site; and
   wherein the elongate body transitions from the at least one helical section to a stand-off proximal tail at the proximal end of the elongate body, the stand-off proximal tail comprising a distal portion adjacent to and bending from the at least one helical section, a proximal portion, and a bend disposed between the distal portion and the proximal portion.

* * * * *

UNITED STATES PATENT AND TRADEMARK OFFICE
CERTIFICATE OF CORRECTION

PATENT NO. : 10,188,397 B2
APPLICATION NO. : 15/192085
DATED : January 29, 2019
INVENTOR(S) : Jaime Vasquez et al.

Page 1 of 1

It is certified that error appears in the above-identified patent and that said Letters Patent is hereby corrected as shown below:

In the Specification

In Column 2, Lines 36-37: "(Redwood City Calif.)" and "(Redmond Wash.)" should read -- (Redwood City, Calif.) -- and -- (Redmond, Wash.) --, respectively.

In Column 3, Line 10: delete "catherter" and insert -- catheter --.

In Column 3, Line 20: delete "deamed" and insert -- deemed --.

In Column 13, Line 53: delete "Ar temperature" and insert -- Af temperature --.

In Column 27, Line 54: delete "Hsinopril" and insert -- Lisinopril --.

In Column 27, Line 66: delete "permirolast" and insert -- pemirolast --.

In Column 27, Line 67: delete "jtnay" and insert -- may --.

In Column 28, Line 16: after "instrument" and before "Glass-filled" insert -- . --.

In Column 28, Line 59: delete "Tenkintown" and please insert -- Jenkintown --.

Signed and Sealed this
Seventh Day of May, 2019

Andrei Iancu
*Director of the United States Patent and Trademark Office*